US008871437B2

(12) United States Patent
Inoue et al.

(10) Patent No.: US 8,871,437 B2
(45) Date of Patent: Oct. 28, 2014

(54) CONSTRUCTION OF PROTEIN-RESPONSIVE SHRNA/RNAI CONTROL SYSTEM USING RNP MOTIF

(75) Inventors: Tan Inoue, Kyoto (JP); Hirohide Saito, Kyoto (JP); Shunichi Kashida, Kyoto (JP); Karin Hayashi, Kyoto (JP)

(73) Assignee: Japan Science and Technology Agency, Saitama (JP)

( * ) Notice: Subject to any disclaimer, the term of this patent is extended or adjusted under 35 U.S.C. 154(b) by 537 days.

(21) Appl. No.: 13/133,709

(22) PCT Filed: Dec. 9, 2009

(86) PCT No.: PCT/JP2009/070580
§ 371 (c)(1),
(2), (4) Date: Jul. 13, 2011

(87) PCT Pub. No.: WO2010/067811
PCT Pub. Date: Jun. 17, 2010

(65) Prior Publication Data
US 2011/0263026 A1    Oct. 27, 2011

(30) Foreign Application Priority Data
Dec. 9, 2008   (JP) ................................. 2008-312951

(51) Int. Cl.
*C12Q 1/68*      (2006.01)
*C12P 19/34*     (2006.01)
*C12N 15/63*     (2006.01)
*C07H 21/02*     (2006.01)
*C07H 21/04*     (2006.01)

(52) U.S. Cl.
USPC ........ 435/6; 435/91.1; 435/91.31; 435/320.1; 435/375; 435/455; 530/350; 536/23.1; 536/24.5

(58) Field of Classification Search
USPC ............ 435/6, 91.1, 91.31, 320.1, 455, 3, 75, 435/375; 514/44; 536/23.1, 24.5; 530/350
See application file for complete search history.

(56) References Cited

U.S. PATENT DOCUMENTS

2008/0194027 A1*  8/2008  Dreyfuss et al. ............. 435/440

OTHER PUBLICATIONS

Beisel et al., Molecular Systems Biology, vol. 4, Article No. 224, pp. 1-14 (2008).*
Deans et al, Cell, vol. 130, pp. 363-372 (2007).*
Turner et al, RNA, vol. 11, pp. 1192-1200 (2005).*
Beisel et al., Model-guided design of ligand-regulated RNAi for programmable control of gene expression, Molecular Systems Biology, 2008, vol. 4, pp. 1-14.
Deans et al., A tunable genetic switch based on RNAi and repressor proteins for regulating gene expression in mammalian cells, Cell, 2007, vol. 130, No. 2, pp. 363-372.
Saito et al., Synthetic human cell fate regulation by protein-driven RNA switches, Nature Communications, 2011, vol. 2., No. 160, pp. 1-8.
International Supplementary European Search Report issued Aug. 29, 2012 in European Patent Application No. EP09831915.5, PCT/JP2009070580.
Osamu Nagae et al. , "Jinko RNAi/RNP o Mochiita Hito Gan Saibo deno Hon'yaku Seigyo System no Kochiku", Dai 80 Kai The Japanese Biochemical Society Taikai Dai 30 Kai Annual Meeting of the Molecular Biology Society of Japan Godo Taikai Koen Yoshishu, 2007, 4P-1321.
An, C. -I. et al., Artificial control of gene expression in mammalian cells by modulating RNA interference through aptamer-small molecule interaction, RNA, 2006, vol. 12, No. 5, pp. 710-716.
Hirohisa Ono et al., "RNA—Tanpakushitsu Sogo Sayo Motif L7Ae-BoxC/D o Mochiita Nanoscale Kozotai no Sekkei Oyobi Kochiku", RNA Meeting, Jul. 23, 2008, vol. 10th, p. 144.
Shun'ichi Kashida et al., "RNP Sogo Sayo o Mochiita Tanpakushitsu Otogata shRNA System no Kochiku to Apoptosis Keiro no Seigyo", Dai 82 Kai The Japanese Biochemical Society Taikai Program•Koen Yoshishu, Sep. 25, 2009, 4T15a-10.
Turner, B. et al., Induced fit of RNA on binding the L7Ae protein to the kink-turn motif, RNA, 2005, vol. 11, No. 8, p. 1192-1200.
International Search Report issued Mar. 9, 2010 in corresponding International Application No. PCT/JP2009/070580, 2 pages.

* cited by examiner

*Primary Examiner* — Jane Zara
(74) *Attorney, Agent, or Firm* — Meunier Carlin & Curfman, LLC

(57) ABSTRACT

An object of the present invention is to provide an RNAi control system using an RNA-protein interaction motif. The present invention provides an shRNA comprising: a guide strand having a sequence complementary to a target sequence; a passenger strand which forms a duplex with the guide strand; and a linker strand which links the guide strand and the passenger strand, wherein the linker strand comprises an RNP-derived protein-binding motif sequence. The present invention also provides an RNAi control system comprising: the shRNA; and an RNP-derived protein which specifically binds to a protein-binding motif sequence in the shRNA.

9 Claims, 17 Drawing Sheets

<shRNA-GFP (59mer), GFP RNAi Positive Control>

<shRNA-GFP mut (59mer), GFP RNAi Negative Control>

<shRNA-BoxC/D-GFP (63mer)>

<shRNA-BoxC/D-mut-GFP (62mer)>

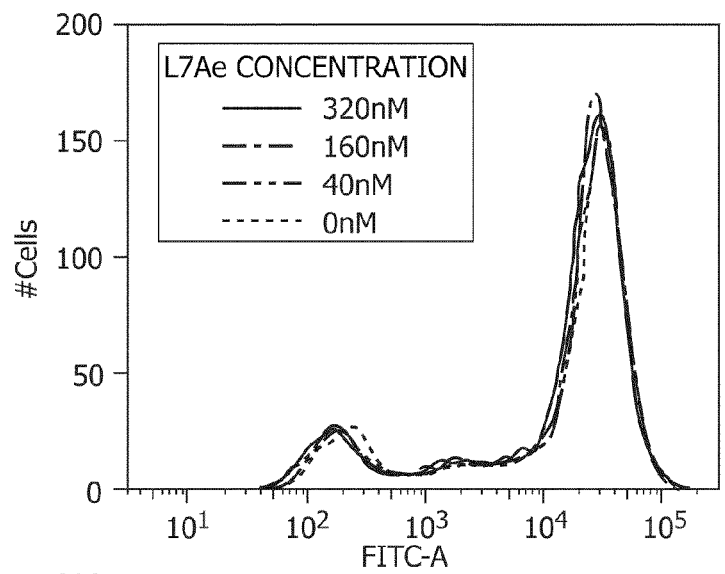
FIG.11(A) Mock
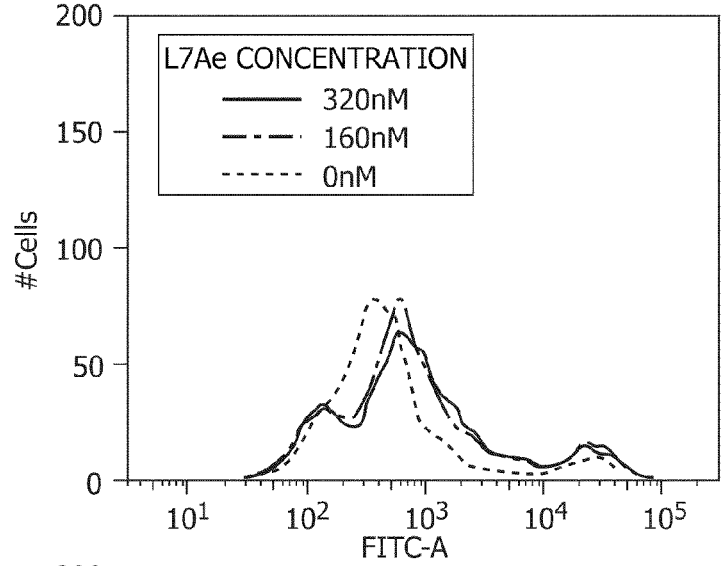
FIG.11(B) shRNA-U1A-4
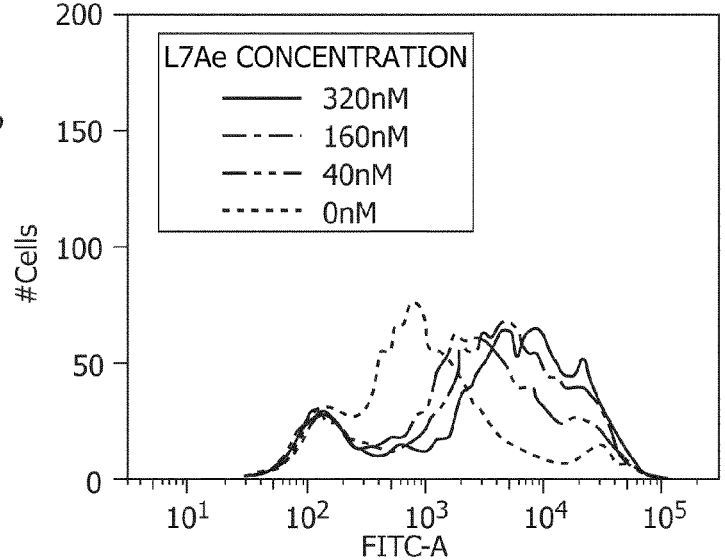
FIG.11(C) shRNA-BoxC/D-GFP

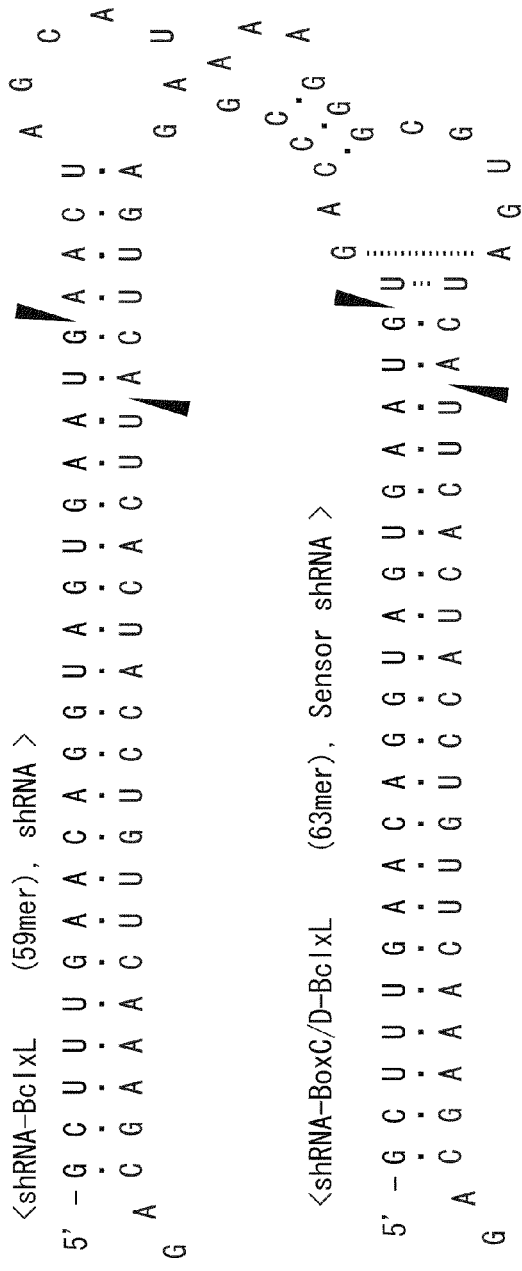
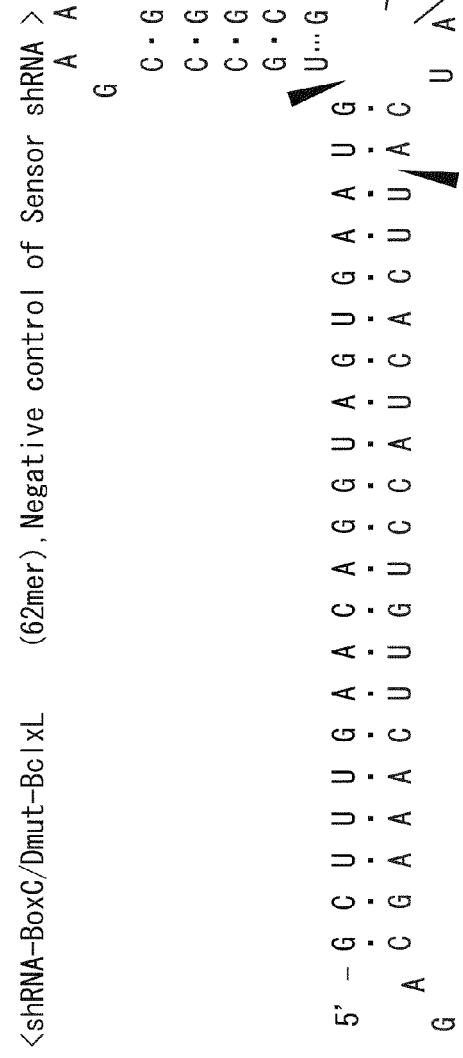
FIG.13(A)
FIG.13(B)
FIG.13(C)

SEQUENCE LISTING

<160> NUMBER OF SEQ ID NOS: 58

<210> SEQ ID NO 1
<211> LENGTH: 139
<212> TYPE: PRT
<213> ORGANISM: homo sapiens

<400> SEQUENCE: 1

```
Met Gly Ser Ser His His His His His His Ser Ser Gly Leu Val Pro
1               5                   10                  15

Arg Gly Ser His Met Tyr Val Arg Phe Glu Val Pro Glu Asp Met Gln
            20                  25                  30

Asn Glu Ala Leu Ser Leu Leu Glu Lys Val Arg Glu Ser Gly Lys Val
        35                  40                  45

Lys Lys Gly Thr Asn Glu Thr Thr Lys Ala Val Glu Arg Gly Leu Ala
    50                  55                  60

Lys Leu Val Tyr Ile Ala Glu Asp Val Asp Pro Pro Glu Ile Val Ala
65                  70                  75                  80

His Leu Pro Leu Leu Cys Glu Glu Lys Asn Val Pro Tyr Ile Tyr Val
                85                  90                  95

Lys Ser Lys Asn Asp Leu Gly Arg Ala Val Gly Ile Glu Val Pro Cys
            100                 105                 110

Ala Ser Ala Ala Ile Ile Asn Glu Gly Glu Leu Arg Lys Glu Leu Gly
        115                 120                 125

Ser Leu Val Glu Lys Ile Lys Gly Leu Gln Lys
    130                 135
```

```
<210> SEQ ID NO 2
<211> LENGTH: 23
<212> TYPE: RNA
<213> ORGANISM: homo sapiens

<400> SEQUENCE: 2
gggcgugaug cgaaagcuga ccc                                           23

<210> SEQ ID NO 3
<211> LENGTH: 19
<212> TYPE: DNA
<213> ORGANISM: Artificial
<220> FEATURE:
<223> OTHER INFORMATION: T7 promoter primer antisense

<400> SEQUENCE: 3
tatagtgagt cgtattagc                                                19

<210> SEQ ID NO 4
<211> LENGTH: 19
<212> TYPE: DNA
<213> ORGANISM: Artificial
<220> FEATURE:
<223> OTHER INFORMATION: T7 sense primer

<400> SEQUENCE: 4
gctaatacga ctcactata                                                19

<210> SEQ ID NO 5
<211> LENGTH: 5653
<212> TYPE: DNA
<213> ORGANISM: Artificial
<220> FEATURE:
<223> OTHER INFORMATION: pET-28b+L7Ae

<400> SEQUENCE: 5
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tccctttagg    180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggatttt gccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
```

```
tggtgagtaa ccatgcatca tcaggagtac ggataaaatg cttgatggtc ggaagaggca      1140
taaattccgt cagccagttt agtctgacca tctcatctgt aacatcattg caacgctac       1200 ctttgccatg tttcagaaac aactctggcg catcgggctt cccatacaat cgatagattg      1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actcttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata gtcgtgtct taccggggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggagaa     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg ccttttgctc acatgttctt cctgcgtta      2160 tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280 tatttctcc ttacgcatct gtgcggtatt tcacaccgca tatatggtgc actctcagta      2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt ttcctgtttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg     2820
ttgtgagggt aaacaactgg cggtatggat gcggcgggac cagagaaaaa tcactcaggg     2880
tcaatgccag cgcttcgtta atacagatgt aggtgttcca cagggtagcc agcagcatcc     2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
```

```
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg     3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatatacc atgggcagca gccatcatca tcatcatcac    5100
agcagcggcc tggtgccgcg cggcagccat atgtacgtga gatttgaggt tcctgaggac    5160
atgcagaacg aagctctgag tctgctggag aaggttaggg agagcggtaa ggtaaagaaa    5220
ggtaccaacg agacgacaaa ggctgtggag aggggactgg caaagctcgt ttacatcgca    5280
gaggatgttg acccgcctga gatcgttgct catctgcccc tcctctgcga ggagaagaat    5340
gtgccgtaca tttacgttaa agcaagaac gaccttggaa gggctgtggg cattgaggtg     5400
ccatgcgctt cggcagcgat aatcaacgag ggagagctga gaaggagct tggaagcctt    5460 gtggagaaga ttaaaggcct tcagaagtaa ctcgagcacc accaccacca ccactgagat    5520
ccggctgcta acaaagcccg aaaggaagct gagttggctg ctgccaccgc tgagcaataa    5580
ctagcataac cccttggggc ctctaaacgg gtcttgaggg gttttttgct gaaaggagga    5640
actatatccg gat                                                       5653
```

<210> SEQ ID NO 6
<211> LENGTH: 5826
<212> TYPE: DNA

<213> ORGANISM: Artificial
<220> FEATURE:
<223> OTHER INFORMATION: pcDNA3_1_L7Ae_myc_His6

<400> SEQUENCE: 6

```
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagt   900
taagcttggt accgagctcg gatccatcat atgcggccgc ttatgtacgt gagatttgag   960
gttcctgagg acatgcagaa cgaagctctg agtctgctgg agaaggttag ggagagcgt   1020
aaggtaaaga aaggtaccaa cgagacgaca aaggctgtgg agaggggact ggcaaagctc  1080
gtttacatcg cagaggatgt tgacccgcct gagatcgttg ctcatctgcc cctcctctgc  1140
gaggagaaga atgtgccgta catttacgtt aaaagcaaga acgacctttgg aagggctgtg  1200
ggcattgagg tgccatgcgc ttcggcagcg ataatcaacg agggagagct gagaaaggag  1260
cttggaagcc ttgtggagaa gattaaaggc cttcagaaga gaattcaact cgagtctaga  1320
gggcccttcg aacaaaaact catctcagaa gaggatctga atatgcatac cggtcatcat  1380
caccatcacc attgagttta aacccgctga tcagcctcga ctgtgccttc tagttgccag  1440
ccatctgttg tttgcccctc cccgtgcctt ccttgaccc tggaaggtgc cactcccact  1500
gtccttttcct aataaaatga ggaaattgca tcgcattgtc tgagtaggtg tcattctatt  1560
ctggggggtg gggtggggca ggacagcaag ggggaggatt gggaagacaa tagcaggcat  1620
gctggggatg cggtgggctc tatggcttct gaggcggaaa gaaccagctg gggctctagg  1680
gggtatcccc acgcgccctg tagcggcgca ttaagcgcgg cgggtgtggt ggttacgcgc  1740
agcgtgaccg ctacacttgc cagcgcccta gcgcccgctc ctttcgcttt cttcccttcc  1800
tttctcgcca cgttcgccgg ctttccccgt caagctctaa atcgggggct ccctttaggg  1860
ttccgattta gtgctttacg gcacctcgac cccaaaaaac ttgattaggg tgatggttca  1920
cgtagtgggc catcgccctg atagacggtt tttcgccctt tgacgttgga gtccacgttc  1980
tttaatagtg gactcttgtt ccaaactgga acaacactca accctatctc ggtctattct  2040
tttgatttat aagggatttt gccgatttcg gcctattggt taaaaaatga gctgatttaa  2100
caaaaattta acgcgaatta attctgtgga atgtgtgtca gttagggtgt ggaaagtccc  2160
caggctcccc agcaggcaga agtatgcaaa gcatgcatct caattagtca gcaaccaggt  2220
```

```
gtggaaagtc cccaggctcc ccagcaggca gaagtatgca aagcatgcat ctcaattagt    2280
cagcaaccat agtcccgccc ctaactccgc ccatcccgcc cctaactccg cccagttccg    2340
cccattctcc gccccatggc tgactaattt tttttattta tgcagaggcc gaggccgcct    2400
ctgcctctga gctattccag aagtagtgag gaggcttttt tggaggccta ggcttttgca    2460
aaaagctccc gggagcttgt atatccattt tcggatctga tcaagagaca ggatgaggat    2520
cgtttcgcat gattgaacaa gatggattgc acgcaggttc tccggccgct tgggtggaga    2580
ggctattcgg ctatgactgg gcacaacaga caatcggctg ctctgatgcc gccgtgttcc    2640
ggctgtcagc gcaggggcgc ccggttcttt ttgtcaagac cgacctgtcc ggtgccctga    2700
atgaactgca ggacgaggca gcgcggctat cgtggctggc cacgacgggc gttccttgcg    2760
cagctgtgct cgacgttgtc actgaagcgg aagggactg gctgctattg ggcgaagtgc    2820
cggggcagga tctcctgtca tctcaccttg ctcctgccga aaagtatcc atcatggctg    2880 atgcaatgcg gcggctgcat acgcttgatc cggctacctg cccattcgac caccaagcga    2940
aacatcgcat cgagcgagca cgtactcgga tggaagccgg tcttgtcgat caggatgatc    3000
tggacgaaga gcatcagggg ctcgcgccag ccgaactgtt cgccaggctc aaggcgcgca    3060
tgcccgacgg cgaggatctc gtcgtgaccc atggcgatgc ctgcttgccg aatatcatgg    3120
tggaaaatgg ccgcttttct ggattcatcg actgtggccg ctgggtgtg gcggaccgct    3180 atcaggacat agcgttggct acccgtgata ttgctgaaga gcttggcggc gaatgggctg    3240
accgcttcct cgtgctttac ggtatcgccg ctcccgattc gcagcgcatc gccttctatc    3300
gccttcttga cgagttcttc tgagcgggac tctggggttc gcgaaatgac cgaccaagcg    3360
acgcccaacc tgccatcacg agatttcgat tccaccgccg ccttctatga aaggttgggc    3420
ttcggaatcg ttttccggga cgccggctgg atgatcctcc agcgcgggga tctcatgctg    3480
gagttcttcg cccacccca cttgtttatt gcagcttata atggttacaa ataaagcaat    3540
agcatcacaa atttcacaaa taaagcattt ttttcactgc attctagttg tggtttgtcc    3600
aaactcatca atgtatctta tcatgtctgt ataccgtcga cctctagcta gagcttggcg    3660
taatcatggt catagctgtt tcctgtgtga aattgttatc cgctcacaat tccacacaac    3720
atacgagccg gaagcataaa gtgtaaagcc tggggtgcct aatgagtgag ctaactcaca    3780
ttaattgcgt tgcgctcact gcccgctttc cagtcgggaa acctgtcgtg ccagctgcat    3840
taatgaatcg gccaacgcgc ggggagaggc ggtttgcgta ttgggcgctc ttccgcttcc    3900
tcgctcactg actcgctgcg ctcggtcgtt cggctgcggc gagcggtatc agctcactca    3960
aaggcggtaa tacggttatc cacagaatca ggggataacg caggaaagaa catgtgagca    4020
aaaggccagc aaaaggccag gaaccgtaaa aaggccgcgt tgctggcgtt tttccatagg    4080
ctccgccccc ctgacgagca tcacaaaaat cgacgctcaa gtcagaggtg gcgaaacccg    4140
acaggactat aaagatacca ggcgtttccc cctggaagct ccctcgtgcg ctctcctgtt    4200
ccgaccctgc cgcttaccgg atacctgtcc gcctttctcc cttcgggaag cgtggcgctt    4260
tctcatagct cacgctgtag gtatctcagt tcggtgtagg tcgttcgctc caagctgggc    4320
tgtgtgcacg aaccccccgt tcagcccgac cgctgcgcct tatccggtaa ctatcgtctt    4380
gagtccaacc cggtaagaca cgacttatcg ccactggcag cagccactgg taacaggatt    4440
agcagagcga ggtatgtagg cggtgctaca gagttcttga agtggtggcc taactacggc    4500
tacactagaa gaacagtatt tggtatctgc gctctgctga agccagttac cttcggaaaa    4560
```

```
agagttggta gctcttgatc cggcaaacaa accaccgctg gtagcggtgg ttttttttgtt    4620 tgcaagcagc agattacgcg cagaaaaaaa ggatctcaag aagatccttt gatcttttct    4680
acggggtctg acgctcagtg gaacgaaaac tcacgttaag ggattttggt catgagatta    4740
tcaaaaagga tcttcaccta gatccttta aattaaaaat gaagttttaa atcaatctaa    4800
agtatatatg agtaaacttg gtctgacagt taccaatgct taatcagtga ggcacctatc    4860
tcagcgatct gtctatttcg ttcatccata gttgcctgac tccccgtcgt gtagataact    4920
acgatacggg agggcttacc atctggcccc agtgctgcaa tgataccgcg agacccacgc    4980
tcaccggctc cagatttatc agcaataaac cagccagccg aagggccgag cgcagaagt    5040 ggtcctgcaa ctttatccgc ctccatccag tctattaatt gttgccggga agctagagta    5100
agtagttcgc cagttaatag tttgcgcaac gttgttgcca ttgctacagg catcgtggtg    5160
tcacgctcgt cgtttggtat ggcttcattc agctccggtt cccaacgatc aaggcgagtt    5220
acatgatccc ccatgttgtg caaaaaagcg gttagctcct tcggtcctcc gatcgttgtc    5280
agaagtaagt tggccgcagt gttatcactc atggttatgg cagcactgca taattctctt    5340
actgtcatgc catccgtaag atgcttttct gtgactggtg agtactcaac caagtcattc    5400
tgagaatagt gtatgcggcg accgagttgc tcttgcccgg cgtcaatacg ggataatacc    5460
gcgccacata gcagaacttt aaaagtgctc atcattggaa aacgttcttc ggggcgaaaa    5520
ctctcaagga tcttaccgct gttgagatcc agttcgatgt aacccactcg tgcacccaac    5580
tgatcttcag catcttttac tttcaccagc gtttctgggt gagcaaaaac aggaaggcaa    5640
aatgccgcaa aaaagggaat aagggcgaca cggaaatgtt gaatactcat actcttcctt    5700
tttcaatatt attgaagcat ttatcagggt tattgtctca tgagcggata catatttgaa    5760
tgtatttaga aaaataaaca aatagggggtt ccgcgcacat ttccccgaaa agtgccacct    5820
gacgtc                                                             5826
```

<210> SEQ ID NO 7
<211> LENGTH: 5493
<212> TYPE: DNA
<213> ORGANISM: Artificial
<220> FEATURE:
<223> OTHER INFORMATION: pcDNA3.1(+)myc His A vector

<400> SEQUENCE: 7

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
```

```
gtaggcgtgt acggtgggag gtctatataa gcagagctct ctggctaact agagaaccca    840
ctgcttactg gcttatcgaa attaatacga ctcactatag ggagacccaa gctggctagt    900
taagcttggt accgagctcg gatccactag tccagtgtgg tggaattctg cagatatcca    960
gcacagtggc ggccgctcga gtctagaggg cccttcgaac aaaaactcat ctcagaagag   1020
gatctgaata tgcataccgg tcatcatcac catcaccatt gagtttaaac ccgctgatca   1080
gcctcgactg tgccttctag ttgccagcca tctgttgttt gcccctcccc cgtgccttcc   1140
ttgaccctgg aaggtgccac tcccactgtc ctttcctaat aaaatgagga aattgcatcg   1200
cattgtctga gtaggtgtca ttctattctg ggggtgggg tggggcagga cagcaagggg   1260
gaggattggg aagacaatag caggcatgct ggggatgcgg tgggctctat ggcttctgag   1320
gcggaaagaa ccagctgggg ctctaggggg tatccccacg cgccctgtag cggcgcatta   1380
agcgcggcgg gtgtggtggt tacgcgcagc gtgaccgcta cacttgccag cgccctagcg   1440
cccgctcctt tcgctttctt cccttccttt ctcgccacgt tcgccggctt tccccgtcaa   1500
gctctaaatc gggggctccc tttagggttc cgatttagtg ctttacggca cctcgacccc   1560
aaaaaacttg attagggtga tggttcacgt agtgggccat cgccctgata cggttttt    1620
cgcccttga cgttggagtc cacgttcttt aatagtggac tcttgttcca aactggaaca   1680
acactcaacc ctatctcggt ctattctttt gatttataag gattttgcc gatttcggcc   1740
tattggttaa aaaatgagct gatttaacaa aaatttaacg cgaattaatt ctgtggaatg   1800
tgtgtcagtt agggtgtgga agtccccag gctccccagc aggcagaagt atgcaaagca   1860
tgcatctcaa ttagtcagca accaggtgtg gaaagtcccc aggctcccca gcaggcagaa   1920
gtatgcaaag catgcatctc aattagtcag caaccatagt cccgccccta actccgccca   1980
tcccgcccct aactccgccc agttccgccc attctccgcc ccatggctga ctaattttt   2040
ttatttatgc agaggccgag gccgcctctg cctctgagct attccagaag tagtgaggag   2100
gcttttttgg aggcctaggc ttttgcaaaa agctcccggg agcttgtata tccattttcg   2160
gatctgatca agagacagga tgaggatcgt ttcgcatgat tgaacaagat ggattgcacg   2220
caggttctcc ggccgcttgg gtggagaggc tattcggcta tgactgggca acagacaa    2280
tcggctgctc tgatgccgcc gtgttccggc tgtcagcgca ggggcgcccg gttctttttg   2340
tcaagaccga cctgtccggt gccctgaatg aactgcagga cgaggcagcg cggctatcgt   2400
ggctggccac gacgggcgtt ccttgcgcag ctgtgctcga cgttgtcact gaagcgggaa   2460
gggactggct gctattgggc gaagtgccgg gcaggatct cctgtcatct caccttgctc   2520
ctgccgagaa agtatccatc atggctgatg caatgcggcg gctgcatacg cttgatccgg   2580
ctacctgccc attcgaccac caagcgaaac atcgcatcga gcgagcacgt actcggatgg   2640
aagccggtct tgtcgatcag gatgatctgg acgaagagca tcaggggctc gcgccagccg   2700
aactgttcgc caggctcaag gcgcgcatgc ccgacggcga ggatctcgtc gtgacccatg   2760
gcgatgcctg cttgccgaat atcatggtgg aaaatggccg cttttctgga ttcatcgact   2820
gtggccggct gggtgtggcg gaccgctatc aggacatagc gttggctacc cgtgatattg   2880
ctgaagagct tggcggcgaa tgggctgacc gcttcctcgt gctttacggt atcgccgctc   2940
ccgattcgca gcgcatcgcc ttctatcgcc ttcttgacga gttcttctga gcgggactct   3000
ggggttcgcg aaatgaccga ccaagcgacg cccaacctgc catcacgaga tttcgattcc   3060
accgccgcct tctatgaaag gttgggcttc ggaatcgttt tccgggacgc cggctggatg   3120
```

```
atcctccagc gcggggatct catgctggag ttcttcgccc accccaactt gtttattgca    3180
gcttataatg gttacaaata aagcaatagc atcacaaatt tcacaaataa agcattttt     3240
tcactgcatt ctagttgtgg tttgtccaaa ctcatcaatg tatcttatca tgtctgtata    3300
ccgtcgacct ctagctagag cttggcgtaa tcatggtcat agctgtttcc tgtgtgaaat    3360
tgttatccgc tcacaattcc acacaacata cgagccggaa gcataaagtg taaagcctgg    3420
ggtgcctaat gagtgagcta actcacatta attgcgttgc gctcactgcc cgctttccag    3480
tcgggaaacc tgtcgtgcca gctgcattaa tgaatcggcc aacgcgcggg gagaggcggt    3540
ttgcgtattg ggcgctcttc cgcttcctcg ctcactgact cgctgcgctc ggtcgttcgg    3600
ctgcggcgag cggtatcagc tcactcaaag gcggtaatac ggttatccac agaatcaggg    3660
gataacgcag gaaagaacat gtgagcaaaa ggccagcaaa aggccaggaa ccgtaaaaag    3720
gccgcgttgc tggcgttttt ccataggctc cgcccccctg acgagcatca caaaaatcga    3780
cgctcaagtc agaggtggcg aaacccgaca ggactataaa gataccaggc gtttccccct    3840
ggaagctccc tcgtgcgctc tcctgttccg accctgccgc ttaccggata cctgtccgcc    3900
tttctccctt cgggaagcgt ggcgctttct catagctcac gctgtaggta tctcagttcg    3960
gtgtaggtcg ttcgctccaa gctgggctgt gtgcacgaac cccccgttca gcccgaccgc    4020
tgcgccttat ccggtaacta tcgtcttgag tccaacccgg taagacacga cttatcgcca    4080
ctggcagcag ccactggtaa caggattagc agagcgaggt atgtaggcgg tgctacagag    4140
ttcttgaagt ggtggcctaa ctacggctac actagaagaa cagtatttgg tatctgcgct    4200
ctgctgaagc cagttacctt cggaaaaaga gttggtagct cttgatccgg caaacaaacc    4260
accgctggta gcggtggttt ttttgtttgc aagcagcaga ttacgcgcag aaaaaaagga    4320
tctcaagaag atcctttgat cttttctacg gggtctgacg ctcagtggaa cgaaaactca    4380
cgttaaggga ttttggtcat gagattatca aaaaggatct tcacctagat ccttttaaat    4440
taaaaatgaa gttttaaatc aatctaaagt atatatgagt aaacttggtc tgacagttac    4500
caatgcttaa tcagtgaggc acctatctca gcgatctgtc tatttcgttc atccatagtt    4560
gcctgactcc ccgtcgtgta gataactacg atacgggagg gcttaccatc tggccccagt    4620
gctgcaatga taccgcgaga cccacgctca ccggctccag atttatcagc aataaaccag    4680
ccagccggaa gggccgagcg cagaagtggt cctgcaactt tatccgcctc catccagtct    4740
attaattgtt gccgggaagc tagagtaagt agttcgccag ttaatagttt gcgcaacgtt    4800
gttgccattg ctacaggcat cgtggtgtca cgctcgtcgt ttggtatggc ttcattcagc    4860
tccggttccc aacgatcaag gcgagttaca tgatccccca tgttgtgcaa aaaagcggtt    4920
agctccttcg gtcctccgat cgttgtcaga agtaagttgg ccgcagtgtt atcactcatg    4980
gttatggcag cactgcataa ttctcttact gtcatgccat ccgtaagatg cttttctgtg    5040
actggtgagt actcaaccaa gtcattctga atagtgta tgcggcgacc gagttgctct    5100
tgcccggcgt caatacggga taataccgcg ccacatagca gaactttaaa agtgctcatc    5160
attggaaaac gttcttcggg gcgaaaactc tcaaggatct taccgctgtt gagatccagt    5220
tcgatgtaac ccactcgtgc acccaactga tcttcagcat cttttacttt caccagcgtt    5280
tctgggtgag caaaaacagg aaggcaaaat gccgcaaaaa agggaataag ggcgacacgg    5340
aaatgttgaa tactcatact cttcctttt caatattatt gaagcattta tcagggttat    5400
tgtctcatga gcggatacat atttgaatgt atttagaaaa ataaacaaat aggggttccg    5460
cgcacatttc cccgaaaagt gccacctgac gtc                                 5493
```

<210> SEQ ID NO 8
<211> LENGTH: 3869
<212> TYPE: DNA
<213> ORGANISM: Artificial
<220> FEATURE:
<223> OTHER INFORMATION: pENTR(TM)/H1/TO vector

<400> SEQUENCE: 8

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca atccgctcc cggcggattt gtcctactca ggagagcgtt caccgacaaa     420
caacagataa acgaaaggc ccagtcttcc gactgagcct ttcgttttat ttgatgcctg     480
gcagttccct actctcgcgt taattcgccc ttagacatga taagatacat tgatgagttt     540
ggacaaacca caactagaat gcagtgaaaa aaatgcttta tttgtgaaat ttgtgatgct     600
attgctttat ttgtaaccat tataagctgc aataaacaag ttggggtggg cgaagaactc     660
cagcatgaga tccccgcgct ggaggatcat ccagccggcg tcccggaaaa cgattccgaa     720
gcccaacctt tcatagaagg cggcggtgga atcgaaatct cgtagcacgt gtcagtcctg     780
ctcctcggcc acgaagtgca cgcagttgcc ggccgggtcg cgcagggcga actcccgccc     840
ccacggctgc tcgccgatct cggtcatggc cggcccggag gcgtcccgga agttcgtgga     900
cacgacctcc gaccactcgg cgtacagctc gtccaggccg cgcacccaca cccaggccag     960
ggtgttgtcc ggcaccatct ggtcctggac cgcgctgatg aacagggtca cgtcgtcccg    1020
gaccacaccg gcgaagtcgt cctccacgaa gtcccggag aacccgagcc ggtcggtcca    1080
gaactcgacc gctccggcga cgtcgcgcgc ggtgagcacc ggaacggcac tggtcaactt    1140
ggccatggtt agttcctca ccttgtcgta ttatactatg ccgatatact atgccgatga    1200
ttaattgtca acacgtgctg atcagatccg aaaatggata tacaagctcc cgggagcttt    1260
ttgcaaaagc ctaggcctcc aaaaaagcct cctcactact tctggaatag ctcagaggca    1320
gaggcggcct cggcctctgc ataaataaaa aaaattagtc agccatgggg cggagaatgg    1380
gcggaactgg gcggagttag gggcgggatg ggcggagtta ggggcgggac tatggttgct    1440
gactaattga gatgcatgct ttgcatactt ctgcctgctg gggagcctgg ggactttcca    1500
cacctggttg ctgactaatt gagatgcatg ctttgcatac ttctgcctgc tggggagcct    1560
ggggactttc cacaccctaa ctgacacaca ttccacagcc gaagggcgaa ttaacgctag    1620
catggatgtt tcccagtca cgacgttgta aaacgacggc cagtcttaag ctcgggcccc    1680
aaataatgat tttattttga ctgatagtga cctgttcgtt gcaacaaatt gatgagcaat    1740
gcttttttat aatgccaact tgtacaaaa aagcaggctt taaaggaacc aattcagtcg    1800
actggatccg gtaccggggc ccccctcgaa gatctaatat ttgcatgtcg ctatgtgttc    1860
tgggaaatca ccataaacgt gaaatccta tcagtgatag agacttataa gttccctatc    1920
agtgatagag acacctttt tgtcgagctt ccttcgggaa gctctccata ttttttggat    1980
ccactagttc tagacccagc tttcttgtac aaagttggca ttataagaaa gcattgctta    2040
```

```
tcaatttgtt gcaacgaaca ggtcactatc agtcaaaata aaatcattat ttgccatcca    2100
gctgatatcc cctatagtga gtcgtattac atggtcatag ctgtttcctg gcagctctgg    2160
cccgtgtctc aaaatctctg atgttacatt gcacaagata aaaatatatc atcatgaaca    2220
ataaaactgt ctgcttacat aaacagtaat acaaggggtg ttatgagcca tattcaacgg    2280
gaaacgtcga ggccgcgatt aaattccaac atggatgctg atttatatgg gtataaatgg    2340
gctcgcgata atgtcgggca atcaggtgcg acaatctatc gcttgtatgg gaagcccgat    2400
gcgccagagt tgtttctgaa acatggcaaa ggtagcgttg ccaatgatgt tacagatgag    2460
atggtcagac taaactggct gacggaattt atgcctcttc cgaccatcaa gcattttatc    2520
cgtactcctg atgatgcatg gttactcacc actgcgatcc ccggaaaaac agcattccag    2580
gtattagaag aatatcctga ttcaggtgaa aatattgttg atgcgctggc agtgttcctg    2640
cgccggttgc attcgattcc tgtttgtaat tgtccttta acagcgatcg cgtatttcgt    2700
ctcgctcagg cgcaatcacg aatgaataac ggtttggttg atgcgagtga ttttgatgac    2760
gagcgtaatg gctggcctgt tgaacaagtc tggaaagaaa tgcataaact tttgccattc    2820
tcaccggatt cagtcgtcac tcatggtgat ttctcacttg ataaccttat ttttgacgag    2880
gggaaattaa taggttgtat tgatgttgga cgagtcggaa tcgcagaccg ataccaggat    2940
cttgccatcc tatggaactg cctcggtgag ttttctcctt cattacagaa acggcttttt    3000
caaaaatatg gtattgataa tcctgatatg aataaattgc agtttcattt gatgctcgat    3060
gagttttctc aatcagaatt ggttaattgg ttgtaacact ggcagagcat tacgctgact    3120
tgacgggacg cgcaagctc atgaccaaaa tcccttaacg tgagttacgc gtcgttccac    3180
tgagcgtcag accccgtaga aaagatcaaa ggatcttctt gagatccttt ttttctgcgc    3240
gtaatctgct gcttgcaaac aaaaaaacca ccgctaccag cggtggtttg tttgccggat    3300
caagagctac caactctttt tccgaaggta actggcttca gcagagcgca gataccaaat    3360
actgttcttc tagtgtagcc gtagttaggc caccacttca agaactctgt agcaccgcct    3420
acatacctcg ctctgctaat cctgttacca gtggctgctg ccagtggcga taagtcgtgt    3480
cttaccgggt tggactcaag acgatagtta ccggataagg cgcagcggtc gggctgaacg    3540
gggggttcgt gcacacagcc cagcttggag cgaacgacct acaccgaact gagataccta    3600
cagcgtgagc tatgagaaag cgccacgctt cccgaaggga gaaaggcgga caggtatccg    3660
gtaagcggca gggtcggaac aggagagcgc acgagggagc ttccaggggg aaacgcctgg    3720
tatctttata gtcctgtcgg gtttcgccac ctctgacttg agcgtcgatt tttgtgatgc    3780
tcgtcagggg ggcggagcct atggaaaaac gccagcaacg cggcctttt acggttcctg    3840
gccttttgct ggccttttgc tcacatgtt                                     3869
```

<210> SEQ ID NO 9
<211> LENGTH: 63
<212> TYPE: RNA
<213> ORGANISM: Artificial
<220> FEATURE:
<223> OTHER INFORMATION: shRNA-BoxC/D-GFP

<400> SEQUENCE: 9

```
ggcaucaagg ugaacuucag cugacccgaa agggcgugau gcugaaguuc accuugaugc    60
cag                                                                 63
```

<210> SEQ ID NO 10
<211> LENGTH: 59

```
<212> TYPE: RNA
<213> ORGANISM: Artificial
<220> FEATURE:
<223> OTHER INFORMATION: shRNA-GFP

<400> SEQUENCE: 10
ggcaucaagg ugaacuucaa gauccagcau agggaucuug aaguucaccu ugaugccag     59

<210> SEQ ID NO 11
<211> LENGTH: 62
<212> TYPE: RNA
<213> ORGANISM: Artificial
<220> FEATURE:
<223> OTHER INFORMATION: shRNA-BoxC/D-mut-GFP

<400> SEQUENCE: 11
ggcaucaagg ugaacuucag cugcccgaaa gggcgucaug cugaaguuca ccuugaugcc     60
ag                                                                   62

<210> SEQ ID NO 12
<211> LENGTH: 59
<212> TYPE: RNA
<213> ORGANISM: Artificial
<220> FEATURE:
<223> OTHER INFORMATION: shRNA-GFP-mut

<400> SEQUENCE: 12
gcacuagcgu augaaugaaa gauccagcau agggaucuuu cauucauacg cuagugcag     59

<210> SEQ ID NO 13
<211> LENGTH: 82
<212> TYPE: DNA
<213> ORGANISM: Artificial
<220> FEATURE:
<223> OTHER INFORMATION: L7Aer template

<400> SEQUENCE: 13
ctggcatcaa ggtgaacttc agcatcacgc cctttcgggt cagctgaagt tcaccttgat     60
gcctatagtg agtcgtatta gc                                             82

<210> SEQ ID NO 14
<211> LENGTH: 52
<212> TYPE: RNA
<213> ORGANISM: Artificial
<220> FEATURE:
<223> OTHER INFORMATION: shRNA-U1A-4

<400> SEQUENCE: 14
ggcaucaagg ugaacuucag ggcgaaagcc cugaaguuca ccuugaugcc ag             52

<210> SEQ ID NO 15
<211> LENGTH: 81
<212> TYPE: DNA
<213> ORGANISM: Artificial
<220> FEATURE:
<223> OTHER INFORMATION: L7AerN template

<400> SEQUENCE: 15
ctggcatcaa ggtgaacttc agcatgacgc cctttcgggc agctgaagtt caccttgatg     60
cctatagtga gtcgtattag c                                              81

<210> SEQ ID NO 16
<211> LENGTH: 78
<212> TYPE: DNA
```

<213> ORGANISM: Artificial
<220> FEATURE:
<223> OTHER INFORMATION: 481P template

<400> SEQUENCE: 16

```
ctggcatcaa ggtgaacttc aagatcccta tgctggatct tgaagttcac cttgatgcct    60
atagtgagtc gtattagc                                                   78
```

<210> SEQ ID NO 17
<211> LENGTH: 3930
<212> TYPE: DNA
<213> ORGANISM: Artificial
<220> FEATURE:
<223> OTHER INFORMATION: pENTR/H1/TO-shRNA-BoxC/D-GFP

<400> SEQUENCE: 17

```
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagtttta tggcgggcgt cctgcccgcc accctccggg ccgttgcttc   360
acaacgttca aatccgctcc cggcggattt gtcctactca ggagagcgtt caccgacaaa   420
caacagataa aacgaaaggc ccagtcttcc gactgagcct ttcgttttat ttgatgcctg   480
gcagttccct actctcgcgt taattcgccc ttagacatga taagatacat tgatgagttt   540
ggacaaacca caactagaat gcagtgaaaa aatgctttta tttgtgaaat ttgtgatgct   600
attgctttat ttgtaaccat tataagctgc aataaacaag ttggggtggg cgaagaactc   660
cagcatgaga tccccgcgct ggaggatcat ccagccggcg tcccggaaaa cgattccgaa   720
gcccaacctt tcatagaagg cggcggtgga atcgaaatct cgtagcacgt gtcagtcctg   780
ctcctcggcc acgaagtgca cgcagttgcc ggccgggtcg cgcagggcga actcccgccc   840
ccacggctgc tcgccgatct cggtcatggc cggcccggag gcgtcccgga agttcgtgga   900
cacgacctcc gaccactcgg cgtacagctc gtccaggccg cgcacccaca cccaggccag   960
ggtgttgtcc ggcaccatct ggtcctggac gcgctgatg aacagggtca cgtcgtcccg   1020
gaccacaccg gcgaagtcgt cctccacgaa gtcccgggag aacccgagcc ggtcggtcca   1080
gaactcgacc gctccggcga cgtcgcgcgc ggtgagcacc ggaacggcac tggtcaactt   1140
ggccatggtt tagttcctca ccttgtcgta ttatactatg ccgatatact atgccgatga   1200
ttaattgtca acacgtgctg atcagatccg aaaatggata tacaagctcc cgggagcttt   1260
ttgcaaaagc ctaggcctcc aaaaaagcct cctcactact tctggaatag ctcagaggca   1320
gaggcggcct cggcctctgc ataaataaaa aaaattagtc agccatgggg cggagaatgg   1380
gcggaactgg gcggagttag gggcgggatg ggcggagtta ggggcgggac tatggttgct   1440
gactaattga gatgcatgct ttgcatactt ctgcctgctg gggagcctgg ggactttcca   1500
cacctggttg ctgactaatt gagatgcatg ctttgcatac ttctgcctgc tggggagcct   1560
ggggactttc cacacccta actgacacaca ttccacagcc gaagggcgaa ttaacgctag   1620
catggatgtt tcccagtca cgacgttgta aaacgacggc cagtcttaag ctcgggcccc   1680
aaataatgat ttatttttga ctgatagtga cctgttcgtt gcaacaaatt gatgagcaat   1740
gcttttttat aatgccaact ttgtacaaaa aagcaggctt taaggaacc aattcagtcg   1800
```

-continued

```
actggatccg gtaccgggcc cccctcgaa gatctaatat ttgcatgtcg ctatgtgttc    1860
tgggaaatca ccataaacgt gaaatccta tcagtgatag agacttataa gttccctatc    1920
agtgatagag acaccggcat caaggtgaac ttcagctgac ccgaaagggc gtgatgctga   1980
agttcacctt gatgcctttt ttgtcgagct tccttcggga agctctccat atttttgga    2040
tccactagtt ctagacccag ctttcttgta caaagttggc attataagaa agcattgctt   2100
atcaatttgt tgcaacgaac aggtcactat cagtcaaaat aaaatcatta tttgccatcc   2160
agctgatatc ccctatagtg agtcgtatta catggtcata gctgtttcct ggcagctctg   2220
gcccgtgtct caaatctct gatgttacat tgcacaagat aaaaatatat catcatgaac    2280
aataaaactg tctgcttaca taaacagtaa tacaaggggt gttatgagcc atattcaacg   2340
ggaaacgtcg aggccgcgat taaattccaa catggatgct gatttatatg gtataaatg    2400
ggctcgcgat aatgtcgggc aatcaggtgc gacaatctat cgcttgtatg ggaagcccga   2460
tgcgccagag ttgtttctga acatggcaa aggtagcgtt gccaatgatg ttacagatga    2520
gatggtcaga ctaaactggc tgacggaatt tatgcctctt ccgaccatca agcattttat   2580
ccgtactcct gatgatgcat ggttactcac cactgcgatc cccggaaaaa cagcattcca   2640
ggtattagaa gaatatcctg attcaggtga aaatattgtt gatgcgctgg cagtgttcct   2700
gcgccggttg cattcgattc ctgtttgtaa ttgtcctttt aacagcgatc gcgtatttcg   2760
tctcgctcag gcgcaatcac gaatgaataa cggtttggtt gatgcgagtg attttgatga   2820
cgagcgtaat ggctggcctg ttgaacaagt ctggaaagaa atgcataaac ttttgccatt   2880
ctcaccggat tcagtcgtca ctcatggtga tttctcactt gataaccttta ttttgacga   2940
ggggaaatta ataggttgta ttgatgttgg acgagtcgga atcgcagacc gataccagga   3000
tcttgccatc ctatggaact gcctcggtga gttttctcct tcattacaga aacggctttt   3060
tcaaaaatat ggtattgata atcctgtata gaataaattg cagtttcatt tgatgctcga   3120
tgagttttc taatcagaat tggttaattg gttgtaacac tggcagagca ttacgctgac    3180
ttgacgggac ggcgcaagct catgaccaaa atcccttaac gtgagttacg cgtcgttcca   3240
ctgagcgtca gaccccgtag aaaagatcaa aggatcttct tgagatcctt ttttctgcg    3300
cgtaatctgc tgcttgcaaa caaaaaaacc accgctacca gcggtggttt gtttgccgga   3360
tcaagagcta ccaactcttt ttccgaaggt aactggcttc agcagagcgc agataccaaa   3420
tactgttctt ctagtgtagc cgtagttagg ccaccacttc aagaactctg tagcaccgcc   3480
tacatacctc gctctgctaa tcctgttacc agtggctgct gccagtggcg ataagtcgtg   3540
tcttaccggg ttggactcaa gacgatagtt accggataag gcgcagcggt cgggctgaac   3600
ggggggttcg tgcacacagc ccagcttgga gcgaacgacc tacaccgaac tgagatacct   3660
acagcgtgag ctatgagaaa gcgccacgct tcccgaaggg agaaaggcgg acaggtatcc   3720
ggtaagcggc agggtcggaa caggagagcg cacgagggag cttccagggg gaaacgcctg   3780
gtatctttat agtcctgtcg ggtttcgcca cctctgactt gagcgtcgat ttttgtgatg   3840
ctcgtcaggg gggcggagcc tatggaaaaa cgccagcaac gcggcctttt tacggttcct   3900
ggccttttgc tggccttttg ctcacatgtt                                    3930
```

<210> SEQ ID NO 18
<211> LENGTH: 65
<212> TYPE: DNA
<213> ORGANISM: Artificial
<220> FEATURE:

<223> OTHER INFORMATION: pENTR L7Aer Top strand

<400> SEQUENCE: 18

```
caccggcatc aaggtgaact tcagctgacc cgaaagggcg tgatgctgaa gttcaccttg    60
atgcc                                                                65
```

<210> SEQ ID NO 19
<211> LENGTH: 65
<212> TYPE: DNA
<213> ORGANISM: Artificial
<220> FEATURE:
<223> OTHER INFORMATION: pENTR L7Aer Bottom strand

<400> SEQUENCE: 19

```
aaaaggcatc aaggtgaact tcagcatcac gcccttccgg gtcagctgaa gttcaccttg    60
atgcc                                                                65
```

<210> SEQ ID NO 20
<211> LENGTH: 20
<212> TYPE: DNA
<213> ORGANISM: Artificial
<220> FEATURE:
<223> OTHER INFORMATION: H1 Forward Primer

<400> SEQUENCE: 20

```
tgttctggga aatcaccata                                                20
```

<210> SEQ ID NO 21
<211> LENGTH: 17
<212> TYPE: DNA
<213> ORGANISM: Artificial
<220> FEATURE:
<223> OTHER INFORMATION: M13 Reverse Primer

<400> SEQUENCE: 21

```
caggaaacag ctatgac                                                   17
```

<210> SEQ ID NO 22
<211> LENGTH: 3929
<212> TYPE: DNA
<213> ORGANISM: Artificial
<220> FEATURE:
<223> OTHER INFORMATION: pENTR/H1/TO-shRNA-BoxC/D-mut-GFP

<400> SEQUENCE: 22

```
ctttcctgcg ttatccctg attctgtgga taaccgtatt accgcctttg agtgagctga     60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca atccgctcc cggcggattt gtcctactca ggagagcgtt caccgacaaa   420
caacagataa acgaaaggc ccagtcttcc gactgagcct ttcgttttat ttgatgcctg   480
gcagttccct actctcgcgt taattcgccc ttagacatga taagatacat tgatgagttt   540
ggacaaacca caactagaat gcagtgaaaa aatgctttta tttgtgaaat ttgtgatgct   600
attgctttat ttgtaaccat tataagctgc aataaacaag ttggggtggg cgaagaactc   660
cagcatgaga tccccgcgct ggaggatcat ccagccggcg tcccggaaaa cgattccgaa   720
```

```
gcccaaccttt tcatagaagg cggcggtgga atcgaaatct cgtagcacgt gtcagtcctg    780
ctcctcggcc acgaagtgca cgcagttgcc ggccgggtcg cgcagggcga actcccgccc    840
ccacggctgc tcgccgatct cggtcatggc cggcccggag cgtcccgga agttcgtgga     900 cacgacctcc gaccactcgg cgtacagctc gtccaggccg cgcacccaca cccaggccag    960
ggtgttgtcc ggcaccatct ggtcctggac cgcgctgatg aacagggtca cgtcgtcccg   1020
gaccacaccg gcgaagtcgt cctccacgaa gtcccgggag aacccgagcc ggtcggtcca   1080
gaactcgacc gctccggcga cgtcgcgcgc ggtgagcacc ggaacggcac tggtcaactt   1140
ggccatggtt tagttcctca ccttgtcgta ttatactatg ccgatatact atgccgatga   1200
ttaattgtca acacgtgctg atcagatccg aaaatggata tacaagctcc cgggagcttt   1260
ttgcaaaagc ctaggcctcc aaaaaagcct cctcactact tctggaatag ctcagaggca   1320
gaggcggcct cggcctctgc ataaataaaa aaaattagtc agccatgggg cggagaatgg   1380
gcggaactgg gcggagttag gggcgggatg ggcggagtta ggggcgggac tatggttgct   1440
gactaattga gatgcatgct ttgcatactt ctgcctgctg gggagcctgg ggactttcca   1500
cacctggttg ctgactaatt gagatgcatg ctttgcatac ttctgcctgc tggggagcct   1560
ggggactttc cacacccctaa ctgacacaca ttccacagcc gaagggcgaa ttaacgctag   1620
catggatgtt ttcccagtca cgacgttgta aaacgacggc cagtcttaag ctcgggcccc   1680
aaataatgat tttattttga ctgatagtga cctgttcgtt gcaacaaatt gatgagcaat   1740
gcttttttat aatgccaact ttgtacaaaa aagcaggctt taaaggaacc aattcagtcg   1800
actggatccg gtaccgggcc cccctcgaa gatctaatat ttgcatgtcg ctatgtgttc    1860
tgggaaatca ccataaacgt gaaatcccta tcagtgatag agacttataa gttccctatc   1920
agtgatagag acaccggcat caaggtgaac ttcagctgcc cgaaagggcg tcatgctgaa   1980
gttcaccttg atgccttttt tgtcgagctt ccttcgggaa gctctccata ttttttggat   2040
ccactagttc tagacccagc tttcttgtac aaagttggca ttataagaaa gcattgctta   2100
tcaatttgtt gcaacgaaca ggtcactatc agtcaaaata aaatcattat ttgccatcca   2160
gctgatatcc cctatagtga gtcgtattac atggtcatag ctgtttcctg gcagctctgg   2220
cccgtgtctc aaaatctctg atgttacatt gcacaagata aaaatatatc atcatgaaca   2280
ataaaactgt ctgcttacat aaacagtaat acaaggggtg ttatgagcca tattcaacgg   2340
gaaacgtcga ggccgcgatt aaattccaac atggatgctg atttatatgg gtataaatgg   2400
gctcgcgata atgtcgggca atcaggtgcg acaatctatc gcttgtatgg gaagcccgat   2460
gcgccagagt tgtttctgaa acatggcaaa ggtagcgttg ccaatgatgt tacagatgag   2520
atggtcagac taaactggct gacgaatttt atgcctcttc cgaccatcaa gcattttatc   2580
cgtactcctg atgatgcatg gttactcacc actgcgatcc ccggaaaaac agcattccag   2640
gtattagaag aatatcctga ttcaggtgaa aatattgttg atgcgctggc agtgttcctg   2700
cgccggttgc attcgattcc tgtttgtaat tgtccttta acagcgatcg cgtatttcgt   2760
ctcgctcagg cgcaatcacg aatgaataac ggtttggttg atgcgagtga ttttgatgac   2820
gagcgtaatg gctggcctgt tgaacaagtc tggaaagaaa tgcataaact tttgccattc   2880
tcaccggatt cagtcgtcac tcatggtgat ttctcacttg ataaccttat ttttgacgag   2940
gggaaattaa taggttgtat tgatgttgga cgagtcggaa tcgcagaccg ataccaggat   3000
cttgccatcc tatggaactg cctcggtgag ttttctcctt cattacagaa acggcttttt   3060
```

```
caaaaatatg gtattgataa tcctgatatg aataaattgc agtttcattt gatgctcgat    3120
gagtttttct aatcagaatt ggttaattgg ttgtaacact ggcagagcat acgctgact     3180 tgacgggacg gcgcaagctc atgaccaaaa tcccttaacg tgagttacgc gtcgttccac    3240
tgagcgtcag accccgtaga aaagatcaaa ggatcttctt gagatccttt ttttctgcgc    3300
gtaatctgct gcttgcaaac aaaaaaacca ccgctaccag cggtggtttg tttgccggat    3360
caagagctac caactctttt tccgaaggta actggcttca gcagagcgca gataccaaat    3420
actgttcttc tagtgtagcc gtagttaggc caccacttca agaactctgt agcaccgcct    3480
acatacctcg ctctgctaat cctgttacca gtggctgctg ccagtggcga taagtcgtgt    3540
cttaccgggt tggactcaag acgatagtta ccggataagg cgcagcggtc gggctgaacg    3600
gggggttcgt gcacacagcc cagcttggag cgaacgacct acaccgaact gagatacccta   3660 cagcgtgagc tatgagaaag cgccacgctt cccgaaggga gaaaggcgga caggtatccg    3720
gtaagcggca gggtcggaac aggagagcgc acgagggagc ttccaggggg aaacgcctgg    3780
tatctttata gtcctgtcgg gtttcgccac ctctgacttg agcgtcgatt tttgtgatgc    3840
tcgtcagggg gcggagcct atggaaaaac gccagcaacg cggcctttt acggttcctg     3900 gccttttgct ggccttttgc tcacatgtt                                      3929

<210> SEQ ID NO 23
<211> LENGTH: 64
<212> TYPE: DNA
<213> ORGANISM: Artificial
<220> FEATURE:
<223> OTHER INFORMATION: pENTR L7AerN Top strand

<400> SEQUENCE: 23
caccggcatc aaggtgaact tcagctgccc gaaagggcgt catgctgaag ttcaccttga     60
tgcc                                                                  64

<210> SEQ ID NO 24
<211> LENGTH: 64
<212> TYPE: DNA
<213> ORGANISM: Artificial
<220> FEATURE:
<223> OTHER INFORMATION: pENTR L7AerN Bottom strand

<400> SEQUENCE: 24
aaaaggcatc aaggtgaact tcagcatgac gccctttcgg gcagctgaag ttcaccttga     60
tgcc                                                                  64

<210> SEQ ID NO 25
<211> LENGTH: 3926
<212> TYPE: DNA
<213> ORGANISM: Artificial
<220> FEATURE:
<223> OTHER INFORMATION: pENTR/H1/TO-shRNA-GFP

<400> SEQUENCE: 25
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
```

```
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taattcgccc ttagacatga taagatacat tgatgagttt    540
ggacaaacca caactagaat gcagtgaaaa aaatgcttta tttgtgaaat ttgtgatgct    600
attgctttat ttgtaaccat tataagctgc aataaacaag ttggggtggg cgaagaactc    660
cagcatgaga tccccgcgct ggaggatcat ccagccggcg tcccggaaaa cgattccgaa    720
gcccaacctt tcatagaagg cggcggtgga atcgaaatct cgtagcacgt gtcagtcctg    780
ctcctcggcc acgaagtgca cgcagttgcc ggccgggtcg cgcagggcga actcccgccc    840
ccacggctgc tcgccgatct cggtcatggc cggcccggag gcgtcccgga agttcgtgga    900
cacgacctcc gaccactcgg cgtacagctc gtccaggccg cgcacccaca cccaggccag    960
ggtgttgtcc ggcaccatct ggtcctggac cgcgctgatg aacagggtca cgtcgtcccg   1020
gaccacaccg gcgaagtcgt cctccacgaa gtcccgggag aacccgagcc ggtcggtcca   1080
gaactcgacc gctccggcga cgtcgcgcgc ggtgagcacc ggaacggcac tggtcaactt   1140
ggccatggtt tagttcctca ccttgtcgta ttatactatg ccgatatact atgccgatga   1200
ttaattgtca acacgtgctg atcagatccg aaaatggata tacaagctcc cgggagcttt   1260
ttgcaaaagc ctaggcctcc aaaaaagcct cctcactact tctggaatag ctcagaggca   1320
gaggcggcct cggcctctgc ataaataaaa aaaattagtc agccatgggg cggagaatgg   1380
gcggaactgg gcggagttag gggcgggatg ggcggagtta ggggcgggac tatggttgct   1440
gactaattga gatgcatgct ttgcatactt ctgcctgctg gggagcctgg ggactttcca   1500
cacctggttg ctgactaatt gagatgcatg ctttgcatac ttctgcctgc tggggagcct   1560
ggggactttc cacaccctaa ctgacacaca ttccacagcc aagggcgaa ttaacgctag   1620 catggatgtt ttcccagtca cgacgttgta aaacgacggc cagtcttaag ctcgggcccc   1680
aaataatgat tttattttga ctgatagtga cctgttcgtt gcaacaaatt gatgagcaat   1740
gcttttttat aatgccaact ttgtacaaaa aagcaggctt taaaggaacc aattcagtcg   1800
actggatccg gtaccgggcc cccctcgaa gatctaatat ttgcatgtcg ctatgtgttc   1860
tgggaaatca ccataaacgt gaaatcccta tcagtgatag agacttataa gttccctatc   1920
agtgatagag acaccggcat caaggtgaac ttcaagatcc agcataggga tcttgaagtt   1980
caccttgatg cctttttgt cgagcttcct tcgggaagct ctccatattt tttggatcca   2040
ctagttctag acccagcttt cttgtacaaa gttggcatta taagaaagca ttgcttatca   2100
atttgttgca acgaacaggt cactatcagt caaaataaaa tcattatttg ccatccagct   2160
gatatcccct atagtgagtc gtattacatg gtcatagctg tttcctggca gctctggccc   2220
gtgtctcaaa atctctgatg ttacattgca caagataaaa atatatcatc atgaacaata   2280
aaactgtctg cttacataaa cagtaataca aggggtgtta tgagccatat tcaacgggaa   2340
acgtcgaggc cgcgattaaa ttccaacatg gatgctgatt tatatgggta taaatgggct   2400
cgcgataatg tcgggcaatc aggtgcgaca atctatcgct tgtatgggaa gcccgatgcg   2460
ccagagttgt ttctgaaaca tggcaaaggt agcgttgcca atgatgttac agatgagatg   2520
gtcagactaa actggctgac ggaatttatg cctcttccga ccatcaagca ttttatccgt   2580
actcctgatg atgcatggtt actcaccact gcgatcccg gaaaacagc attccaggta   2640 ttagaagaat atcctgattc aggtgaaaat attgttgatg cgctggcagt gttcctgcgc   2700
```

```
cggttgcatt cgattcctgt tgtaattgt ccttttaaca gcgatcgcgt atttcgtctc    2760
gctcaggcgc aatcacgaat gaataacggt ttggttgatg cgagtgattt tgatgacgag    2820
cgtaatggct ggcctgttga acaagtctgg aaagaaatgc ataaactttt gccattctca    2880
ccggattcag tcgtcactca tggtgatttc tcacttgata accttatttt tgacgagggg    2940
aaattaatag gttgtattga tgttggacga gtcggaatcg cagaccgata ccaggatctt    3000
gccatcctat ggaactgcct cggtgagttt tctccttcat acagaaacg gcttttcaa    3060 aaatatggta ttgataatcc tgatatgaat aaattgcagt ttcatttgat gctcgatgag    3120 ttttctaat cagaattggt taattggttg taacactggc agagcattac gctgacttga    3180
cgggacggcg caagctcatg accaaaatcc cttaacgtga gttacgcgtc gttccactga    3240
gcgtcagacc ccgtagaaaa gatcaaagga tcttcttgag atcctttttt tctgcgcgta    3300
atctgctgct tgcaaacaaa aaaaccaccg ctaccagcgg tggtttgttt gccggatcaa    3360
gagctaccaa ctcttttttcc gaaggtaact ggcttcagca gagcgcagat accaaatact    3420
gttcttctag tgtagccgta gttaggccac cacttcaaga actctgtagc accgcctaca    3480
tacctcgctc tgctaatcct gttaccagtg gctgctgcca gtggcgataa gtcgtgtctt    3540
accgggttgg actcaagacg atagttaccg gataagcgc agcggtcggg ctgaacgggg    3600
ggttcgtgca cacagcccag cttggagcga acgacctaca ccgaactgag atacctacag    3660
cgtgagctat gagaaagcgc cacgcttccc gaagggagaa aggcggacag gtatccggta    3720
agcggcaggg tcggaacagg agagcgcacg agggagcttc caggggggaaa cgcctggtat    3780 ctttatagtc ctgtcgggtt tcgccacctc tgacttgagc gtcgattttt gtgatgctcg    3840 tcagggggggc ggagcctatg gaaaaacgcc agcaacgcgg ccttttacg gttcctggcc    3900 ttttgctggc cttttgctca catgtt                                          3926

<210> SEQ ID NO 26
<211> LENGTH: 61
<212> TYPE: DNA
<213> ORGANISM: Artificial
<220> FEATURE:
<223> OTHER INFORMATION: pENTR 481P Top strand

<400> SEQUENCE: 26
caccggcatc aaggtgaact tcaagatcca gcatagggat cttgaagttc accttgatgc    60
c                                                                     61

<210> SEQ ID NO 27
<211> LENGTH: 61
<212> TYPE: DNA
<213> ORGANISM: Artificial
<220> FEATURE:
<223> OTHER INFORMATION: pENTR 481P Bottom strand

<400> SEQUENCE: 27
aaaaggcatc aaggtgaact tcaagatccc tatgctggat cttgaagttc accttgatgc    60
c                                                                     61

<210> SEQ ID NO 28
<211> LENGTH: 3926
<212> TYPE: DNA
<213> ORGANISM: Artificial
<220> FEATURE:
<223> OTHER INFORMATION: pENTR/H1/TO-shRNA-GFP-mut

<400> SEQUENCE: 28
```

```
ctttcctgcg ttatccctg attctgtgga taaccgtatt accgcctttg agtgagctga      60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgtttat ttgatgcctg     480 gcagttccct actctcgcgt taattcgccc ttagacatga aagatacat tgatgagttt    540 ggacaaacca caactagaat gcagtgaaaa aaatgcttta tttgtgaaat ttgtgatgct    600
attgctttat ttgtaaccat tataagctgc aataaacaag ttggggtggg cgaagaactc    660
cagcatgaga tccccgcgct ggaggatcat ccagccggcg tccggaaaaa cgattccgaa    720
gcccaacctt tcatagaagg cggcggtgga atcgaaatct cgtagcacgt gtcagtcctg    780
ctcctcggcc acgaagtgca cgcagttgcc ggccgggtcg cgcagggcga actcccgccc    840
ccacggctgc tcgccgatct cggtcatggc cggcccggag gcgtcccgga agttcgtgga    900
cacgacctcc gaccactcgg cgtacagctc gtccaggccg cgcacccaca cccaggccag    960
ggtgttgtcc ggcaccatct ggtcctggac cgcgctgatg aacagggtca cgtcgtcccg   1020
gaccacaccg gcgaagtcgt cctccacgaa gtcccgggag aacccgagcc ggtcggtcca   1080
gaactcgacc gctccggcga cgtcgcgcgc ggtgagcacc ggaacggcac tggtcaactt   1140
ggccatggtt tagttcctca ccttgtcgta ttatactatg ccgatatact atgccgatga   1200
ttaattgtca acacgtgctg atcagatccg aaaatggata tacaagctcc cgggagcttt   1260
ttgcaaaagc ctaggcctcc aaaaaagcct cctcactact tctggaatag ctcagaggca   1320
gaggcggcct cggcctctgc ataaataaaa aaaattagtc agccatgggg cggagaatgg   1380
gcggaactgg gcggagttag gggcgggatg ggcggagtta ggggcgggac tatggttgct   1440
gactaattga gatgcatgct ttgcatactt ctgcctgctg gggagcctgg ggactttcca   1500
cacctggttg ctgactaatt gagatgcatg ctttgcatac ttctgcctgc tggggagcct   1560
ggggactttc cacacccctaa ctgacacaca ttccacagcc gaagggcgaa ttaacgctag   1620
catggatgtt tcccagtcac gacgttgta aaacgacggc cagtcttaag ctcgggcccc   1680
aaataatgat tttattttga ctgatagtga cctgttcgtt gcaacaaatt gatgagcaat   1740
gcttttttat aatgccaact ttgtacaaaa aagcaggctt taaggaacc aattcagtcg    1800 actggatccg gtaccgggcc cccctcgaa gatctaatat ttgcatgtcg ctatgtgttc    1860
tgggaaatca ccataaacgt gaaatcccta tcagtgatag agacttataa gttccctatc   1920
agtgatagag acaccgcact agcgtatgaa tgaaagatcc agcataggga tctttcattc    1980
atacgctagt gctttttgt cgagcttcct tcgggaagct ctccatattt tttggatcca    2040
ctagttctag acccagcttt cttgtacaaa gttggcatta taagaaagca ttgcttatca    2100
atttgttgca acgaacaggt cactatcagt caaaataaaa tcattatttg ccatccagct    2160
gatatcccct atagtgagtc gtattacatg gtcatagctg tttcctggca gctctggccc    2220
gtgtctcaaa atctctgatg ttacattgca caagataaaa atatatcatc atgaacaata    2280
aaactgtctg cttacataaa cagtaataca agggtgtta tgagccatat tcaacgggaa    2340
```

```
acgtcgaggc cgcgattaaa ttccaacatg gatgctgatt tatatgggta taaatgggct    2400
cgcgataatg tcgggcaatc aggtgcgaca atctatcgct tgtatgggaa gcccgatgcg    2460
ccagagttgt ttctgaaaca tggcaaaggt agcgttgcca atgatgttac agatgagatg    2520
gtcagactaa actggctgac ggaatttatg cctcttccga ccatcaagca ttttatccgt    2580
actcctgatg atgcatggtt actcaccact gcgatcccg gaaaaacagc attccaggta    2640
ttagaagaat atcctgattc aggtgaaaat attgttgatg cgctggcagt gttcctgcgc    2700
cggttgcatt cgattcctgt ttgtaattgt ccttttaaca gcgatcgcgt atttcgtctc    2760
gctcaggcgc aatcacgaat gaataacggt ttggttgatg cgagtgattt tgatgacgag    2820
cgtaatggct ggcctgttga acaagtctgg aaagaaatgc ataaacttttt gccattctca    2880 ccggattcag tcgtcactca tggtgatttc tcacttgata accttatttt tgacgagggg    2940
aaattaatag gttgtattga tgttggacga gtcggaatcg cagaccgata ccaggatctt    3000
gccatcctat ggaactgcct cggtgagttt tctccttcat tacagaaacg gcttttttcaa    3060 aaatatggta ttgataatcc tgatatgaat aaattgcagt ttcatttgat gctcgatgag    3120
tttttctaat cagaattggt taattggttg taacactggc agagcattac gctgacttga    3180
cgggacggcg caagctcatg accaaaatcc cttaacgtga gttacgcgtc gttccactga    3240
gcgtcagacc ccgtagaaaa gatcaaagga tcttcttgag atcctttttt tctgcgcgta    3300
atctgctgct tgcaaacaaa aaaaccaccg ctaccagcgg tggtttgttt gccggatcaa    3360
gagctaccaa ctctttttcc gaaggtaact ggcttcagca gagcgcagat accaaatact    3420
gttcttctag tgtagccgta gttaggccac cacttcaaga actctgtagc accgcctaca    3480
tacctcgctc tgctaatcct gttaccagtg gctgctgcca gtggcgataa gtcgtgtctt    3540
accgggttgg actcaagacg atagttaccg gataaggcgc agcggtcggg ctgaacgggg    3600
ggttcgtgca cacagcccag cttggagcga acgacctaca ccgaactgag atacctacag    3660
cgtgagctat gagaaagcgc cacgcttccc gaagggagaa aggcggacag gtatccggta    3720
agcggcaggg tcggaacagg agagcgcacg agggagcttc caggggaaac gcctggtat    3780 ctttatagtc ctgtcgggtt tcgccacctc tgacttgagc gtcgattttt gtgatgctcg    3840 tcagggggc ggagcctatg gaaaaacgcc agcaacgcgg cctttttacg gttcctggcc    3900
ttttgctggc cttttgctca catgtt    3926

<210> SEQ ID NO 29
<211> LENGTH: 61
<212> TYPE: DNA
<213> ORGANISM: Artificial
<220> FEATURE:
<223> OTHER INFORMATION: pENTR Sk-7N Top strand

<400> SEQUENCE: 29
caccgcacta gcgtatgaat gaaagatcca gcatagggat ctttcattca tacgctagtg    60
c                                                                   61

<210> SEQ ID NO 30
<211> LENGTH: 61
<212> TYPE: DNA
<213> ORGANISM: Artificial
<220> FEATURE:
<223> OTHER INFORMATION: pENTR Sk-7N Bottom strand

<400> SEQUENCE: 30
aaaagcacta gcgtatgaat gaaagatccc tatgctggat ctttcattca tacgctagtg    60
```

```
                                        -continued
c                                                                        61

<210> SEQ ID NO 31
<211> LENGTH: 71
<212> TYPE: DNA
<213> ORGANISM: Artificial
<220> FEATURE:
<223> OTHER INFORMATION: shRNA-U1A-4 template

<400> SEQUENCE: 31
ctggcatcaa ggtgaacttc agggctttcg ccctgaagtt caccttgatg cctatagtga        60
gtcgtattag c                                                             71

<210> SEQ ID NO 32
<211> LENGTH: 44
<212> TYPE: DNA
<213> ORGANISM: Artificial
<220> FEATURE:
<223> OTHER INFORMATION: BamHI-NdeI-NotI-L7Ae-primer

<400> SEQUENCE: 32
aaggatccat catatgcggc cgcttatgta cgtgagattt gagg                         44

<210> SEQ ID NO 33
<211> LENGTH: 36
<212> TYPE: DNA
<213> ORGANISM: Artificial
<220> FEATURE:
<223> OTHER INFORMATION: L7Ae-EcoRI-XhoI-primer

<400> SEQUENCE: 33
cactcgagtt gaattctctt ctgaaggcct ttaatc                                  36

<210> SEQ ID NO 34
<211> LENGTH: 20
<212> TYPE: DNA
<213> ORGANISM: Artificial
<220> FEATURE:
<223> OTHER INFORMATION: T7 promoter primer

<400> SEQUENCE: 34
taatacgact cactataggg                                                    20

<210> SEQ ID NO 35
<211> LENGTH: 21
<212> TYPE: DNA
<213> ORGANISM: Artificial
<220> FEATURE:
<223> OTHER INFORMATION: BGHrev primer

<400> SEQUENCE: 35
gctggcaact agaaggcaca g                                                  21

<210> SEQ ID NO 36
<211> LENGTH: 17
<212> TYPE: DNA
<213> ORGANISM: Artificial
<220> FEATURE:
<223> OTHER INFORMATION: 481P Fwd

<400> SEQUENCE: 36
caaggaggac ggcaaca                                                       17

<210> SEQ ID NO 37
```

```
<211> LENGTH: 20
<212> TYPE: DNA
<213> ORGANISM: Artificial
<220> FEATURE:
<223> OTHER INFORMATION: 481P Rev

<400> SEQUENCE: 37
ccttgatgcc gttcttctgc                                                 20

<210> SEQ ID NO 38
<211> LENGTH: 19
<212> TYPE: DNA
<213> ORGANISM: Artificial
<220> FEATURE:
<223> OTHER INFORMATION: GAPDH Fwd

<400> SEQUENCE: 38
agccacatcg ctcagacac                                                  19

<210> SEQ ID NO 39
<211> LENGTH: 19
<212> TYPE: DNA
<213> ORGANISM: Artificial
<220> FEATURE:
<223> OTHER INFORMATION: GAPDH Rev

<400> SEQUENCE: 39
gcccaatacg accaaatcc                                                  19

<210> SEQ ID NO 40
<211> LENGTH: 6548
<212> TYPE: DNA
<213> ORGANISM: Artificial Sequence
<220> FEATURE:
<223> OTHER INFORMATION: pcDNA3.1-AsRed2-L7Ae-myc-His6

<400> SEQUENCE: 40
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagt   900
taagcttggt accgagctcg gatccactag tccagtgtgg tggaattccc accatggcct   960
cttttctgaa gaagaccatg cccttcagga ccaccatcga gggcaccgtg aacgccact  1020
acttcaagtg caccggcaag ggcgagggca acccctgga gggcacccag gagatgaaga  1080
```

```
tcgaggtgat cgagggcggc ccctgccct tcgccttcca catcctgtcc acctcctgca    1140
tgtacggctc caaggccttc atcaagtacg tgtccggcat ccccgactac ttcaagcagt    1200
ccctccccga gggcttcacc tgggagcgca ccaccaccta cgaggacggc ggcttcctga    1260
ccgcccacca ggacacctcc ctggacgcg actgcctggt gtacaaggtg aagatcctgg    1320
gcaacaactt ccccgccgac ggccccgtga tgcagaacaa ggccggccgc tgggagccct    1380
ccaccgagat cgtgtacgag gtggacgcg tgctgcgcgg ccagtccctg atggccctgg    1440
agtgccccgg cggtcgccac ctgacctgcc acctgcacac cacctaccgc tccaagaagc    1500
ccgcctccgc cctgaagatg cccggcttcc acttcgagga ccaccgcatc gagatcctgg    1560
aggaggtgga gaagggcaag tgctacaagc agtacgaggc cgccgtgggc cgctactgcg    1620
acgccgcccc ctccaagctg ggccacaacg aagggcggcc gcttatgtac gtgagatttg    1680
aggttcctga ggacatgcag aacgaagctc tgagtctgct ggagaaggtt agggagagcg    1740
gtaaggtaaa gaaaggtacc aacgagacga caaaggctgt ggagagggga ctggcaaagc    1800
tcgtttacat cgcagaggat gttgacccgc ctgagatcgt tgctcatctg cccctcctct    1860
gcgaggagaa gaatgtgccg tacatttacg ttaaaagcaa gaacgacctt ggaagggctg    1920
tgggcattga ggtgccatgc gcttcggcag cgataatcaa cgagggagag ctgagaaagg    1980
agcttggaag ccttgtggag aagattaaag gccttcagaa gagaattcaa ctcgagtcta    2040
gagggccctt cgaacaaaaa ctcatctcag aagaggatct gaatatgcat accggtcatc    2100
atcaccatca ccattgagtt taaacccgct gatcagcctc gactgtgcct tctagttgcc    2160
agccatctgt tgtttgcccc tcccccgtgc cttccttgac cctggaaggt gccactccca    2220
ctgtcctttc ctaataaaat gaggaaattg catcgcattg tctgagtagg tgtcattcta    2280
ttctgggggg tggggtgggg caggacagca aggggggagga ttgggaagac aatagcaggc    2340
atgctgggga tgcggtgggc tctatggctt ctgaggcgga agaaccagc tggggctcta    2400 gggggtatcc ccacgcgccc tgtagcggcg cattaagcgc ggcgggtgtg gtggttacgc    2460
gcagcgtgac cgctacactt gccagcgccc tagcgcccgc tcctttcgct ttcttccctt    2520
cctttctcgc cacgttcgcc ggctttcccc gtcaagctct aaatcggggg ctccctttag    2580
ggttccgatt tagtgcttta cggcacctcg accccaaaaa acttgattag ggtgatggtt    2640
cacgtagtgg gccatcgccc tgatagacgg ttttttcgcc ctttgacgttg gagtccacgt    2700 tctttaatag tggactcttg ttccaaactg gaacaacact caaccctatc tcggtctatt    2760
cttttgattt ataagggatt ttgccgattt cggcctattg gttaaaaaat gagctgattt    2820
aacaaaaatt taacgcgaat taattctgtg gaatgtgtgt cagttagggt gtggaaagtc    2880
cccaggctcc ccagcaggca gaagtatgca aagcatgcat ctcaattagt cagcaaccag    2940
gtgtggaaag tccccaggct cccagcagg cagaagtatg caaagcatgc atctcaatta    3000
gtcagcaacc atagtcccgc ccctaactcc gcccatcccg cccctaactc cgcccagttc    3060
cgcccattct ccgccccatg ctgactaat tttttttatt tatgcagagg ccgaggccgc    3120
ctctgcctct gagctattcc agaagtagtg aggaggcttt tttggaggcc taggcttttg    3180
caaaaagctc ccgggagctt gtatatccat tttcggatct gatcaagaga caggatgagg    3240
atcgtttcgc atgattgaac aagatggatt gcacgcaggt tctccggccg cttgggtgga    3300
gaggctattc ggctatgact gggcacaaca gacaatcggc tgctctgatg ccgccgtgtt    3360
ccggctgtca gcgcaggggc gcccggttct ttttgtcaag accgacctgt ccggtgccct    3420
```

```
gaatgaactg caggacgagg cagcgcggct atcgtggctg gccacgacgg gcgttccttg    3480
cgcagctgtg ctcgacgttg tcactgaagc gggaagggac tggctgctat tgggcgaagt    3540
gccggggcag gatctcctgt catctcacct tgctcctgcc gagaaagtat ccatcatggc    3600
tgatgcaatg cggcggctgc atacgcttga tccggctacc tgcccattcg accaccaagc    3660
gaaacatcgc atcgagcgag cacgtactcg gatggaagcc ggtcttgtcg atcaggatga    3720
tctggacgaa gagcatcagg ggctcgcgcc agccgaactg ttcgccaggc tcaaggcgcg    3780
catgcccgac ggcgaggatc tcgtcgtgac ccatggcgat gcctgcttgc cgaatatcat    3840
ggtggaaaat ggccgctttt ctggattcat cgactgtggc cggctgggtg tggcggaccg    3900
ctatcaggac atagcgttgg ctacccgtga tattgctgaa gagcttggcg gcgaatgggc    3960
tgaccgcttc ctcgtgcttt acggtatcgc cgctcccgat tcgcagcgca tcgccttcta    4020
tcgccttctt gacgagttct tctgagcggg actctggggt tcgcgaaatg accgaccaag    4080
cgacgcccaa cctgccatca cgagatttcg attccaccgc cgccttctat gaaaggttgg    4140
gcttcggaat cgttttccgg gacgccggct ggatgatcct ccagcgcggg gatctcatgc    4200
tggagttctt cgcccacccc aacttgttta ttgcagctta taatggttac aaataaagca    4260
atagcatcac aaatttcaca aataaagcat ttttttcact gcattctagt tgtggtttgt    4320
ccaaactcat caatgtatct tatcatgtct gtataccgtc gacctctagc tagagcttgg    4380
cgtaatcatg gtcatagctg tttcctgtgt gaaattgtta tccgctcaca attccacaca    4440
acatacgagc cggaagcata aagtgtaaag cctggggtgc ctaatgagtg agctaactca    4500
cattaattgc gttgcgctca ctgcccgctt tccagtcggg aaacctgtcg tgccagctgc    4560
attaatgaat cggccaacgc gcggggagag gcggtttgcg tattgggcgc tcttccgctt    4620
cctcgctcac tgactcgctg cgctcggtcg ttcggctgcg gcgagcggta tcagctcact    4680
caaaggcggt aatacggtta tccacagaat caggggataa cgcaggaaag aacatgtgag    4740
caaaaggcca gcaaaaggcc aggaaccgta aaaaggccgc gttgctggcg tttttccata    4800
ggctccgccc ccctgacgag catcacaaaa atcgacgctc aagtcagagg tggcgaaacc    4860
cgacaggact ataaagatac caggcgtttc ccccctggaag ctccctcgtg cgctctcctg    4920
ttccgaccct gccgcttacc ggatacctgt ccgcctttct cccttcggga agcgtggcgc    4980
tttctcatag ctcacgctgt aggtatctca gttcggtgta ggtcgttcgc tccaagctgg    5040
gctgtgtgca cgaaccccc gttcagcccg accgctgcgc cttatccggt aactatcgtc    5100
ttgagtccaa cccggtaaga cacgacttat cgccactggc agcagccact ggtaacagga    5160
ttagcagagc gaggtatgta ggcggtgcta cagagttctt gaagtggtgg cctaactacg    5220
gctacactag aagaacagta tttggtatct gcgctctgct gaagccagtt accttcggaa    5280
aaagagttgg tagctcttga tccggcaaac aaaccaccgc tggtagcggt ggtttttttg    5340
tttgcaagca gcagattacg cgcagaaaaa aaggatctca agaagatcct ttgatctttt    5400
ctacggggtc tgacgctcag tggaacgaaa actcacgtta agggatttg gtcatgagat    5460
tatcaaaaag gatcttcacc tagatccttt taaattaaaa atgaagtttt aaatcaatct    5520
aaagtatata tgagtaaact tggtctgaca gttaccaatg cttaatcagt gaggcaccta    5580
tctcagcgat ctgtctattt cgttcatcca tagttgcctg actccccgtc gtgtagataa    5640
ctacgatacg ggagggctta ccatctggcc ccagtgctgc aatgataccg cgagacccac    5700
gctcaccggc tccagattta tcagcaataa accagccagc cggaagggcc gagcgcagaa    5760
gtggtcctgc aactttatcc gcctccatcc agtctattaa ttgttgccgg gaagctagag    5820
```

```
taagtagttc gccagttaat agtttgcgca acgttgttgc cattgctaca ggcatcgtgg    5880
tgtcacgctc gtcgtttggt atggcttcat tcagctccgg ttcccaacga tcaaggcgag    5940
ttacatgatc ccccatgttg tgcaaaaaag cggttagctc cttcggtcct ccgatcgttg    6000
tcagaagtaa gttggccgca gtgttatcac tcatggttat ggcagcactg cataattctc    6060
ttactgtcat gccatccgta agatgctttt ctgtgactgg tgagtactca accaagtcat    6120
tctgagaata gtgtatgcgg cgaccgagtt gctcttgccc ggcgtcaata cgggataata    6180
ccgcgccaca tagcagaact ttaaaagtgc tcatcattgg aaaacgttct cggggcgaa     6240 aactctcaag gatcttaccg ctgttgagat ccagttcgat gtaacccact cgtgcaccca    6300
actgatcttc agcatctttt actttcacca gcgtttctgg gtgagcaaaa acaggaaggc    6360
aaaatgccgc aaaaaaggga ataagggcga cacggaaatg ttgaatactc atactcttcc    6420
tttttcaata ttattgaagc atttatcagg gttattgtct catgagcgga tacatatttg    6480
aatgtattta gaaaaataaa caaatagggg ttccgcgcac atttccccga aaagtgccac    6540
ctgacgtc                                                             6548
```

<210> SEQ ID NO 41
<211> LENGTH: 6203
<212> TYPE: DNA
<213> ORGANISM: Artificial Sequence
<220> FEATURE:
<223> OTHER INFORMATION: pcDNA3.1-EGFP-myc-His6

<400> SEQUENCE: 41

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgc cccattgacg caaatgggcg      780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttggt accgagctcg gatccactag tccagtgtgg tggaattccc accatggtga     960
gcaagggcga ggagctgttc accggggtgg tgcccatcct ggtcgagctg gacggcgacg    1020
taaacggcca agttcagc gtgtccggcg agggcgaggg cgatgccacc tacggcaagc      1080
tgaccctgaa gttcatctgc accaccggca agctgcccgt gccctggccc accctcgtga    1140
ccaccctgac ctacggcgtg cagtgcttca gccgctaccc cgaccacatg aagcagcacg    1200
acttcttcaa gtccgccatg cccgaaggct acgtccagga gcgcaccatc ttcttcaagg    1260
```

```
acgacggcaa ctacaagacc cgcgccgagg tgaagttcga gggcgacacc ctggtgaacc    1320
gcatcgagct gaagggcatc gacttcaagg aggacggcaa catcctgggg cacaagctgg    1380
agtacaacta caacagccac aacgtctata tcatggccga caagcagaag aacggcatca    1440
aggtgaactt caagatccgc cacaacatcg aggacggcag cgtgcagctc gccgaccact    1500
accagcagaa cacccccatc ggcgacggcc ccgtgctgct gcccgacaac cactacctga    1560
gcacccagtc cgccctgagc aaagacccca acgagaagcg cgatcacatg gtcctgctgg    1620
agttcgtgac cgccgccggg atcactctcg gcatggacga gctgtacaag aagggcggc    1680 cgcaactcga gtctagaggg cccttcgaac aaaaactcat ctcagaagag gatctgaata    1740
tgcataccgg tcatcatcac catcaccatt gagtttaaac ccgctgatca gcctcgactg    1800
tgccttctag ttgccagcca tctgttgttt gcccctcccc cgtgccttcc ttgaccctgg    1860
aaggtgccac tcccactgtc ctttcctaat aaaatgagga aattgcatcg cattgtctga    1920
gtaggtgtca ttctattctg gggggtgggg tggggcagga cagcaagggg gaggattggg    1980
aagacaatag caggcatgct ggggatgcgg tgggctctat ggcttctgag gcggaaagaa    2040
ccagctgggg ctctagggg tatccccacg cgccctgtag cggcgcatta agcgcggcgg    2100
gtgtggtggt tacgcgcagc gtgaccgcta cacttgccag cgccctagcg cccgctcctt    2160
tcgctttctt cccttccttt ctcgccacgt tcgccggctt tccccgtcaa gctctaaatc    2220
gggggctccc tttagggttc cgatttagtg ctttacggca cctcgacccc aaaaaacttg    2280
attagggtga tggttcacgt agtgggccat cgccctgata dacggttttt cgccctttga    2340
cgttggagtc cacgttcttt aatagtggac tcttgttcca aactggaaca cactcaacc    2400 ctatctcggt ctattctttt gatttataag ggattttgcc gatttcggcc tattggttaa    2460
aaaatgagct gatttaacaa aaatttaacg cgaattaatt ctgtggaatg tgtgtcagtt    2520
agggtgtgga aagtccccag gctccccagc aggcagaagt atgcaaagca tgcatctcaa    2580
ttagtcagca accaggtgtg gaaagtcccc aggctcccca gcaggcagaa gtatgcaaag    2640
catgcatctc aattagtcag caaccatagt cccgccccta actccgccca tcccgcccct    2700
aactccgccc agttccgccc attctccgcc ccatggctga ctaattttt ttatttatgc    2760 agaggccgag gccgcctctg cctctgagct attccagaag tagtgaggag gctttttttgg    2820 aggcctaggc ttttgcaaaa agctcccggg agcttgtata tccattttcg gatctgatca    2880
agagacagga tgaggatcgt ttcgcatgat tgaacaagat ggattgcacg caggttctcc    2940
ggccgcttgg gtgagaggc tattcggcta tgactgggca caacagacaa tcggctgctc    3000
tgatgccgcc gtgttccggc tgtcagcgca ggggcgcccg gttcttttg tcaagaccga    3060 cctgtccggt gccctgaatg aactgcagga cgaggcagcg cggctatcgt ggctggccac    3120
gacgggcgtt ccttgcgcag ctgtgctcga cgttgtcact gaagcgggaa gggactggct    3180
gctattgggc gaagtgccgg ggcaggatct cctgtcatct caccttgctc ctgccgagaa    3240
agtatccatc atggctgatg caatgcggcg gctgcatacg cttgatccgg ctacctgccc    3300
attcgaccac caagcgaaac atcgcatcga gcgagcacgt actcggatgg aagccggtct    3360
tgtcgatcag gatgatctgg acgaagagca tcagggctc gcgccagccg aactgttcgc    3420
caggctcaag gcgcgcatgc ccgacggcga ggatctcgtc gtgacccatg gcgatgcctg    3480
cttgccgaat atcatggtgg aaaatggccg cttttctgga ttcatcgact gtggccggct    3540
gggtgtggcg gaccgctatc aggacatagc gttggctacc cgtgatattg ctgaagagct    3600
tggcggcgaa tgggctgacc gcttcctcgt gctttacggt atcgccgctc ccgattcgca    3660
```

-continued

```
gcgcatcgcc ttctatcgcc ttcttgacga gttcttctga gcgggactct ggggttcgcg    3720
aaatgaccga ccaagcgacg cccaacctgc catcacgaga tttcgattcc accgccgcct    3780
tctatgaaag gttgggcttc ggaatcgttt tccgggacgc cggctggatg atcctccagc    3840
gcggggatct catgctggag ttcttcgccc accccaactt gtttattgca gcttataatg    3900
gttacaaata aagcaatagc atcacaaatt tcacaataa agcatttttt tcactgcatt    3960
ctagttgtgg tttgtccaaa ctcatcaatg tatcttatca tgtctgtata ccgtcgacct    4020
ctagctagag cttggcgtaa tcatggtcat agctgtttcc tgtgtgaaat tgttatccgc    4080
tcacaattcc acacaacata cgagccggaa gcataaagtg taaagcctgg ggtgcctaat    4140
gagtgagcta actcacatta attgcgttgc gctcactgcc cgctttccag tcgggaaacc    4200
tgtcgtgcca gctgcattaa tgaatcggcc aacgcgcggg gagaggcggt ttgcgtattg    4260
ggcgctcttc cgcttcctcg ctcactgact cgctgcgctc ggtcgttcgg ctgcggcgag    4320
cggtatcagc tcactcaaag gcggtaatac ggttatccac agaatcaggg gataacgcag    4380
gaaagaacat gtgagcaaaa ggccagcaaa aggccaggaa ccgtaaaaag gccgcgttgc    4440
tggcgttttt ccataggctc cgcccccctg acgagcatca caaaaatcga cgctcaagtc    4500
agaggtggcg aaacccgaca ggactataaa gataccaggc gtttccccct ggaagctccc    4560
tcgtgcgctc tcctgttccg accctgccgc ttaccggata cctgtccgcc tttctccctt    4620
cgggaagcgt ggcgctttct catagctcac gctgtaggta tctcagttcg gtgtaggtcg    4680
ttcgctccaa gctgggctgt gtgcacgaac cccccgttca gcccgaccgc tgcgccttat    4740
ccggtaacta tcgtcttgag tccaacccgg taagacacga cttatcgcca ctggcagcag    4800
ccactggtaa caggattagc agagcgaggt atgtaggcgg tgctacagag ttcttgaagt    4860
ggtggcctaa ctacggctac actagaagaa cagtatttgg tatctgcgct ctgctgaagc    4920
cagttacctt cggaaaaaga gttggtagct cttgatccgg caaacaaacc accgctggta    4980
gcggtggttt ttttgtttgc aagcagcaga ttacgcgcag aaaaaaagga tctcaagaag    5040
atcctttgat cttttctacg ggtctgacgc tcagtggaa cgaaaactca cgttaaggga    5100
ttttggtcat gagattatca aaaaggatct tcacctagat ccttttaaat taaaaatgaa    5160
gttttaaatc aatctaaagt atatatgagt aaacttggtc tgacagttac caatgcttaa    5220
tcagtgaggc acctatctca gcgatctgtc tatttcgttc atccatagtt gcctgactcc    5280
ccgtcgtgta gataactacg atacgggagg gcttaccatc tggccccagt gctgcaatga    5340
taccgcgaga cccacgctca ccggctccag atttatcagc aataaaccag ccagccggaa    5400
gggccgagcg cagaagtggt cctgcaactt tatccgcctc catccagtct attaattgtt    5460
gccgggaagc tagagtaagt agttcgccag ttaatagttt cgcaacgtt gttgccattg    5520 ctacaggcat cgtggtgtca cgctcgtcgt ttggtatggc ttcattcagc tccggttccc    5580
aacgatcaag gcgagttaca tgatcccca tgttgtgcaa aaaagcggtt agctccttcg    5640
gtcctccgat cgttgtcaga agtaagttgg ccgcagtgtt atcactcatg gttatggcag    5700
cactgcataa ttctcttact gtcatgccat ccgtaagatg cttttctgtg actggtgagt    5760
actcaaccaa gtcattctga aatagtgta tgcggcgacc gagttgctct tgcccggcgt    5820
caatacggga taataccgcg ccacatagca gaactttaaa agtgctcatc attggaaaac    5880
gttcttcggg gcgaaaactc tcaaggatct taccgctgtt gagatccagt tcgatgtaac    5940
ccactcgtgc acccaactga tcttcagcat cttttacttt caccagcgtt tctgggtgag    6000
```

-continued

| | |
|---|---|
| caaaaacagg aaggcaaaat gccgcaaaaa agggaataag ggcgacacgg aaatgttgaa | 6060 |
| tactcatact cttccttttt caatattatt gaagcattta tcagggttat tgtctcatga | 6120 |
| gcggatacat atttgaatgt atttagaaaa ataaacaaat aggggttccg cgcacatttc | 6180 |
| cccgaaaagt gccacctgac gtc | 6203 |

<210> SEQ ID NO 42
<211> LENGTH: 6182
<212> TYPE: DNA
<213> ORGANISM: Artificial
<220> FEATURE:
<223> OTHER INFORMATION: pcDNA3.1-AsRed2-myc-His6

<400> SEQUENCE: 42

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagt | 900 |
| taagcttggt accgagctcg gatccactag tccagtgtgg tggaattccc accatggcct | 960 |
| ctttgctgaa gaagaccatg cccttcagga ccaccatcga gggcaccgtg aacggccact | 1020 |
| acttcaagtg caccggcaag ggcgagggca ccccctgga gggcacccag agatgaaga | 1080 |
| tcgaggtgat cgagggcggc cccctgccct tcgccttcca catcctgtcc acctcctgca | 1140 |
| tgtacggctc caaggccttc atcaagtacg tgtccggcat ccccgactac ttcaagcagt | 1200 |
| ccctccccga gggcttcacc tgggagcgca ccaccaccta cgaggacggc ggcttcctga | 1260 |
| ccgcccacca ggacacctcc ctggacgcg actgcctggt gtacaaggtg aagatcctgg | 1320 |
| gcaacaactt ccccgccgac ggccccgtga tgcagaacaa ggccggccgc tgggagccct | 1380 |
| ccaccgagat cgtgtacgag gtggacggcg tgctgcgcgg ccagtccctg atggcctgg | 1440 |
| agtgccccgg cggtcgccac ctgacctgcc acctgcacac cacctaccgc tccaagaagc | 1500 |
| ccgcctccgc cctgaagatg cccggcttcc acttcgagga ccaccgcatc gagatcctgg | 1560 |
| aggaggtgga aagggcaag tgctacaagc agtacgaggc cgccgtgggc cgctactgcg | 1620 |
| acgccgcccc ctccaagctg ggccacaacg aagggcggcc gcaactcgag tctagagggc | 1680 |
| ccttcgaaca aaaactcatc tcagaagagg atctgaatat gcataccggt catcatcacc | 1740 |
| atcaccattg agtttaaacc cgctgatcag cctcgactgt gccttctagt tgccagccat | 1800 |
| ctgttgtttg cccctccccc gtgccttcct tgaccctgga aggtgccact cccactgtcc | 1860 |

```
tttcctaata aaatgaggaa attgcatcgc attgtctgag taggtgtcat tctattctgg    1920
ggggtggggt ggggcaggac agcaagggg aggattggga agacaatagc aggcatgctg     1980
gggatgcggt gggctctatg gcttctgagg cggaaagaac cagctggggc tctagggggt    2040
atccccacgc gccctgtagc ggcgcattaa gcgcggcggg tgtggtggtt acgcgcagcg    2100
tgaccgctac acttgccagc gccctagcgc ccgctccttt cgctttcttc ccttcctttc    2160
tcgccacgtt cgccggcttt ccccgtcaag ctctaaatcg ggggctccct ttagggttcc    2220
gatttagtgc tttacggcac ctcgacccca aaaaacttga ttagggtgat ggttcacgta    2280
gtgggccatc gccctgatag acggttttc gccctttgac gttggagtcc acgttcttta    2340
atagtggact cttgttccaa actggaacaa cactcaaccc tatctcggtc tattcttttg    2400
atttataagg gattttgccg atttcggcct attggttaaa aaatgagctg atttaacaaa    2460
aatttaacgc gaattaattc tgtggaatgt gtgtcagtta gggtgtggaa agtccccagg    2520
ctccccagca ggcagaagta tgcaaagcat gcatctcaat tagtcagcaa ccaggtgtgg    2580
aaagtcccca ggctccccag caggcagaag tatgcaaagc atgcatctca attagtcagc    2640
aaccatagtc ccgcccctaa ctccgcccat cccgcccta actccgccca gttccgccca    2700
ttctccgccc catggctgac taattttttt tatttatgca gaggccgagg ccgcctctgc    2760
ctctgagcta ttccagaagt agtgaggagg ctttttttgga ggcctaggct tttgcaaaaa    2820
gctcccggga gcttgtatat ccatttttcgg atctgatcaa gagacaggat gaggatcgtt    2880
tcgcatgatt gaacaagatg gattgcacgc aggttctccg gccgcttggg tggagaggct    2940
attcggctat gactgggcac aacagacaat cggctgctct gatgccgccg tgttccggct    3000
gtcagcgcag gggcgcccgg ttcttttttgt caagaccgac ctgtccggtg ccctgaatga    3060
actgcaggac gaggcagcgc ggctatcgtg gctggccacg acgggcgttc cttgcgcagc    3120
tgtgctcgac gttgtcactg aagcgggaag ggactggctg ctattgggcg aagtgccggg    3180
gcaggatctc ctgtcatctc accttgctcc tgccgagaaa gtatccatca tggctgatgc    3240
aatgcggcgg ctgcatacgc ttgatccggc tacctgccca ttcgaccacc aagcgaaaca    3300
tcgcatcgag cgagcacgta ctcggatgga agccggtctt gtcgatcagg atgatctgga    3360
cgaagagcat caggggctcg cgccagccga actgttcgcc aggctcaagg cgcgcatgcc    3420
cgacggcgag gatctcgtcg tgacccatgg cgatgcctgc ttgccgaata tcatggtgga    3480
aaatggccgc ttttctggat tcatcgactg tggccggctg ggtgtggcgg accgctatca    3540
ggacatagcg ttggctaccc gtgatattgc tgaagagctt ggcggcgaat gggctgaccg    3600
cttcctcgtg ctttacggta tcgccgctcc cgattcgcag cgcatcgcct tctatcgcct    3660
tcttgacgag ttcttctgag cgggactctg gggttcgcga aatgaccgac caagcgacgc    3720
ccaacctgcc atcacgagat ttcgattcca ccgccgcctt ctatgaaagg ttgggcttcg    3780
gaatcgtttt ccgggacgcc ggctggatga tcctccagcg cggggatctc atgctggagt    3840
tcttcgccca ccccaacttg tttattgcag cttataatgg ttacaaataa agcaatagca    3900
tcacaaattt cacaaataaa gcatttttt cactgcattc tagttgtggt ttgtccaaac    3960
tcatcaatgt atcttatcat gtctgtatac cgtcgacctc tagctagagc ttggcgtaat    4020
catggtcata gctgtttcct gtgtgaaatt gttatccgct cacaattcca cacaacatac    4080
gagccggaag cataaagtgt aaagcctggg gtgcctaatg agtgagctaa ctcacattaa    4140
ttgcgttgcg ctcactgccc gctttccagt cgggaaacct gtcgtgccag ctgcattaat    4200
```

```
gaatcggcca acgcgcgggg agaggcggtt tgcgtattgg gcgctcttcc gcttcctcgc    4260
tcactgactc gctgcgctcg gtcgttcggc tgcggcgagc ggtatcagct cactcaaagg    4320
cggtaatacg gttatccaca gaatcagggg ataacgcagg aaagaacatg tgagcaaaag    4380
gccagcaaaa ggccaggaac cgtaaaaagg ccgcgttgct ggcgtttttc cataggctcc    4440
gcccccctga cgagcatcac aaaaatcgac gctcaagtca gaggtggcga aacccgacag    4500
gactataaag ataccaggcg tttccccctg gaagctccct cgtgcgctct cctgttccga    4560
ccctgccgct taccggatac ctgtccgcct ttctcccttc gggaagcgtg gcgctttctc    4620
atagctcacg ctgtaggtat ctcagttcgg tgtaggtcgt tcgctccaag ctgggctgtg    4680
tgcacgaacc ccccgttcag cccgaccgct gcgccttatc cggtaactat cgtcttgagt    4740
ccaacccggt aagacacgac ttatcgccac tggcagcagc cactggtaac aggattagca    4800
gagcgaggta tgtaggcggt gctacagagt tcttgaagtg gtggcctaac tacggctaca    4860
ctagaagaac agtatttggt atctgcgctc tgctgaagcc agttaccttc ggaaaaagag    4920
ttggtagctc ttgatccggc aaacaaacca ccgctggtag cggtggtttt tttgtttgca    4980
agcagcagat tacgcgcaga aaaaaaggat ctcaagaaga tcctttgatc ttttctacgg    5040
ggtctgacgc tcagtggaac gaaaactcac gttaagggat tttggtcatg agattatcaa    5100
aaaggatctt cacctagatc cttttaaatt aaaaatgaag ttttaaatca atctaaagta    5160
tatatgagta aacttggtct gacagttacc aatgcttaat cagtgaggca cctatctcag    5220
cgatctgtct atttcgttca tccatagttg cctgactccc cgtcgtgtag ataactacga    5280
tacgggaggg cttaccatct ggccccagtg ctgcaatgat accgcgagac ccacgctcac    5340
cggctccaga tttatcagca ataaaccagc cagccggaag ggccgagcgc agaagtggtc    5400
ctgcaacttt atccgcctcc atccagtcta ttaattgttg ccgggaagct agagtaagta    5460
gttcgccagt taatagtttg cgcaacgttg ttgccattgc tacaggcatc gtggtgtcac    5520
gctcgtcgtt tggtatggct tcattcagct ccggttccca acgatcaagg cgagttacat    5580
gatcccccat gttgtgcaaa aaagcggtta gctccttcgg tcctccgatc gttgtcagaa    5640
gtaagttggc cgcagtgtta tcactcatgg ttatggcagc actgcataat tctcttactg    5700
tcatgccatc cgtaagatgc ttttctgtga ctggtgagta ctcaaccaag tcattctgag    5760
aatagtgtat gcggcgaccg agttgctctt gcccggcgtc aatacgggat aataccgcgc    5820
cacatagcag aactttaaaa gtgctcatca ttggaaaacg ttcttcgggg cgaaaactct    5880
caaggatctt accgctgttg agatccagtt cgatgtaacc cactcgtgca cccaactgat    5940
cttcagcatc ttttactttc accagcgttt ctgggtgagc aaaaacagga aggcaaaatg    6000
ccgcaaaaaa gggaataagg gcgacacgga aatgttgaat actcatactc ttcctttttc    6060
aatattattg aagcatttat cagggttatt gtctcatgag cggatacata tttgaatgta    6120
tttagaaaaa taaacaaata ggggttccgc gcacatttcc ccgaaaagtg ccacctgacg    6180
tc                                                                  6182
```

<210> SEQ ID NO 43
<211> LENGTH: 63
<212> TYPE: RNA
<213> ORGANISM: Artificial
<220> FEATURE:
<223> OTHER INFORMATION: shRNA-BoxC/D- Bcl-xL

<400> SEQUENCE: 43

```
gcuuugaaca gguagugaau gugacccgaa agggcgugau cauucacuac cuguucaaag    60
``` cag                                                             63

<210> SEQ ID NO 44
<211> LENGTH: 82
<212> TYPE: DNA
<213> ORGANISM: Artificial
<220> FEATURE:
<223> OTHER INFORMATION: shRNA-BoxC/D-BclxL template

<400> SEQUENCE: 44
ctgctttgaa caggtagtga atgatcacgc cctttcgggt cacattcact acctgttcaa    60
agctatagtg agtcgtatta gc                                            82

<210> SEQ ID NO 45
<211> LENGTH: 62
<212> TYPE: RNA
<213> ORGANISM: Artificial
<220> FEATURE:
<223> OTHER INFORMATION: shRNA-BoxC/D mut-Bcl-xL

<400> SEQUENCE: 45
gcuuugaaca gguagugaau gugcccgaaa gggcgucauc auucacuacc uguucaaagc    60
ag                                                                  62

<210> SEQ ID NO 46
<211> LENGTH: 81
<212> TYPE: DNA
<213> ORGANISM: Artificial
<220> FEATURE:
<223> OTHER INFORMATION: shRNA-BoxC/D mut-BclxL template

<400> SEQUENCE: 46
ctgctttgaa caggtagtga atgatgacgc cctttcgggc acattcacta cctgttcaaa    60
gctatagtga gtcgtattag c                                             81

<210> SEQ ID NO 47
<211> LENGTH: 59
<212> TYPE: RNA
<213> ORGANISM: Artificial
<220> FEATURE:
<223> OTHER INFORMATION: shRNA-Bcl-xL

<400> SEQUENCE: 47
gcuuugaaca gguagugaau gaacuagcau agaguucauu cacuaccugu ucaaagcag    59

<210> SEQ ID NO 48
<211> LENGTH: 78
<212> TYPE: DNA
<213> ORGANISM: Artificial
<220> FEATURE:
<223> OTHER INFORMATION: shRNA-Bcl-xL template

<400> SEQUENCE: 48
ctgctttgaa caggtagtga atgaactcta tgctagttca ttcactacct gttcaaagct    60
atagtgagtc gtattagc                                                 78

<210> SEQ ID NO 49
<211> LENGTH: 3930
<212> TYPE: DNA
<213> ORGANISM: Artificial
<220> FEATURE:
<223> OTHER INFORMATION: pENTR/H1/TO-shRNA-BoxC/D-Bcl-xL

```
<400> SEQUENCE: 49
ctttcctgcg ttatccctg attctgtgga taaccgtatt accgcctttg agtgagctga      60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taattcgccc ttagacatga aagatacat tgatgagttt     540
ggacaaacca aactagaat gcagtgaaaa aaatgcttta tttgtgaaat ttgtgatgct     600
attgctttat ttgtaaccat tataagctgc aataaacaag ttggggtggg cgaagaactc    660
cagcatgaga tccccgcgct ggaggatcat ccagccggcg tcccggaaaa cgattccgaa    720
gcccaacctt tcatagaagg cggcggtgga atcgaaatct cgtagcacgt gtcagtcctg    780
ctcctcggcc acgaagtgca cgcagttgcc ggccgggtcg cgcagggcga actcccgccc    840
ccacggctgc tcgccgatct cggtcatggc cggcccggag cgtcccgga agttcgtgga    900
cacgacctcc gaccactcgg cgtacagctc gtccaggccg cgcacccaca cccaggccag    960
ggtgttgtcc ggcaccatct ggtcctggac cgcgctgatg aacagggtca cgtcgtcccg   1020
gaccacaccg gcgaagtcgt cctccacgaa gtcccgggag aacccgagcc ggtcggtcca   1080
gaactcgacc gctccggcga cgtcgcgcgc ggtgagcacc ggaacggcac tggtcaactt   1140
ggccatggtt tagttcctca ccttgtcgta ttatactatg ccgatatact atgccgatga   1200
ttaattgtca acacgtgctg atcagatccg aaaatggata tacaagctcc cgggagcttt   1260
ttgcaaaagc ctaggcctcc aaaaaagcct cctcactact tctggaatag ctcagaggca   1320
gaggcggcct cggcctctgc ataaataaaa aaaattagtc agccatgggg cggagaatgg   1380
gcggaactgg gcggagttag gggcgggatg ggcggagtta ggggcgggac tatggttgct   1440
gactaattga gatgcatgct ttgcatactt ctgcctgctg gggagcctgg ggactttcca   1500
cacctggttg ctgactaatt gagatgcatg ctttgcatac ttctgcctgc tggggagcct   1560
ggggactttc cacaccctaa ctgacacaca ttccacagcc gaagggcgaa ttaacgctag   1620
catggatgtt ttcccagtca cgacgttgta aaacgacggc cagtcttaag ctcgggcccc   1680
aaataatgat tttattttga ctgatagtga cctgttcgtt gcaacaaatt gatgagcaat   1740
gcttttttat aatgccaact ttgtacaaaa aagcaggctt taaaggaacc aattcagtcg   1800
actggatccg gtaccgggcc ccccctcgaa gatctaatat ttgcatgtcg ctatgtgttc   1860
tgggaaatca ccataaacgt gaaatcccta tcagtgatag agacttataa gttccctatc   1920
agtgatagag acaccgcttt gaacaggtag tgaatgtgac ccgaaagggc gtgatcattc   1980
actacctgtt caaagctttt ttgtcgagct ccttcgggaa agctctccat atttttggaa   2040
tccactagtt ctagacccag ctttcttgta caaagttggc attataagaa agcattgctt   2100
atcaatttgt tgcaacgaac aggtcactat cagtcaaaat aaaatcatta tttgccatcc   2160
agctgatatc ccctatagtg agtcgtatta catggtcata gctgtttcct ggcagctctg   2220
gcccgtgtct caaaatctct gatgttacat tgcacaagat aaaatatat catcatgaac   2280
aataaaactg tctgcttaca taaacagtaa tacaaggggt gttatgagcc atattcaacg   2340
```

```
ggaaacgtcg aggccgcgat taaattccaa catggatgct gatttatatg ggtataaatg    2400
ggctcgcgat aatgtcgggc aatcaggtgc gacaatctat cgcttgtatg ggaagcccga    2460
tgcgccagag ttgtttctga acatggcaa aggtagcgtt gccaatgatg ttacagatga     2520
gatggtcaga ctaaactggc tgacggaatt tatgcctctt ccgaccatca agcattttat    2580
ccgtactcct gatgatgcat ggttactcac cactgcgatc cccggaaaaa cagcattcca    2640
ggtattagaa gaatatcctg attcaggtga aaatattgtt gatgcgctgg cagtgttcct    2700
gcgccggttg cattcgattc ctgtttgtaa ttgtccttt aacagcgatc gcgtatttcg     2760
tctcgctcag gcgcaatcac gaatgaataa cggtttggtt gatgcgagtg attttgatga    2820
cgagcgtaat ggctggcctg ttgaacaagt ctggaaagaa atgcataaac ttttgccatt    2880
ctcaccggat tcagtcgtca ctcatggtga tttctcactt gataaccta ttttgacga     2940 ggggaaatta ataggttgta ttgatgttgg acgagtcgga atcgcagacc gataccagga    3000
tcttgccatc ctatggaact gcctcggtga gttttctcct tcattacaga aacggctttt    3060
tcaaaaatat ggtattgata atcctgatat gaataaattg cagtttcatt tgatgctcga    3120 tgagttttc taatcagaat tggttaattg gttgtaacac tggcagagca ttacgctgac     3180
ttgacgggac ggcgcaagct catgaccaaa atcccttaac gtgagttacg cgtcgttcca    3240
ctgagcgtca gaccccgtag aaaagatcaa aggatcttct tgagatcctt ttttctgcg    3300 cgtaatctgc tgcttgcaaa caaaaaaacc accgctacca gcggtggttt gtttgccgga    3360
tcaagagcta ccaactcttt ttccgaaggt aactggcttc agcagagcgc agataccaaa    3420
tactgttctt ctagtgtagc cgtagttagg ccaccacttc aagaactctg tagcaccgcc    3480
tacatacctc gctctgctaa tcctgttacc agtggctgct gccagtggcg ataagtcgtg    3540
tcttaccggg ttggactcaa gacgatagtt accggataag gcgcagcggt cgggctgaac    3600
ggggggttcg tgcacacagc ccagcttgga gcgaacgacc tacaccgaac tgagatacct    3660
acagcgtgag ctatgagaaa gcgccacgct tcccgaaggg agaaaggcgg acaggtatcc    3720
ggtaagcggc agggtcggaa caggagagcg cacgagggag cttccagggg gaaacgcctg    3780
gtatctttat agtcctgtcg ggtttcgcca cctctgactt gagcgtcgat ttttgtgatg    3840
ctcgtcaggg gggcggagcc tatggaaaaa cgccagcaac gcggcctttt tacggttcct    3900
ggccttttgc tggccttttg ctcacatgtt                                     3930

<210> SEQ ID NO 50
<211> LENGTH: 65
<212> TYPE: DNA
<213> ORGANISM: Artificial
<220> FEATURE:
<223> OTHER INFORMATION: BoxC/D Bcl-xL Top strand

<400> SEQUENCE: 50
caccgctttg aacaggtagt gaatgtgacc cgaaagggcg tgatcattca ctacctgttc    60
aaagc                                                                65

<210> SEQ ID NO 51
<211> LENGTH: 65
<212> TYPE: DNA
<213> ORGANISM: Artificial
<220> FEATURE:
<223> OTHER INFORMATION: BoxC/D Bcl-xL Bottom strand

<400> SEQUENCE: 51
```

```
aaaagctttg aacaggtagt gaatgatcac gcccttccgg gtcacattca ctacctgttc    60
aaagc                                                                65

<210> SEQ ID NO 52
<211> LENGTH: 3929
<212> TYPE: DNA
<213> ORGANISM: Artificial
<220> FEATURE:
<223> OTHER INFORMATION: pENTR H1 TO-shRNA-BoxC/D mut-Bcl-xL

<400> SEQUENCE: 52
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca atccgctccc ggcggatttg tcctactcag gagagcgttc accgacaaac   420
aacagataaa acgaaaggcc cagtcttcc gactgagcct ttcgttttat ttgatgcctg   480
gcagttccct actctcgcgt taattcgccc ttagacatga aagatacat tgatgagttt   540 ggacaaacca caactagaat gcagtgaaaa aaatgcttta tttgtgaaat ttgtgatgct   600
attgctttat ttgtaaccat tataagctgc aataaacaag ttggggtggg cgaagaactc   660
cagcatgaga tccccgcgct ggaggatcat ccagccggcg tcccgaaaa cgattccgaa   720 gcccaacctt tcatagaagg cggcggtgga atcgaaatct cgtagcacgt gtcagtcctg   780
ctcctcggcc acgaagtgca cgcagttgcc ggccgggtcg cgcagggcga actcccgccc   840
ccacggctgc tcgccgatct cggtcatggc cggcccggag gcgtcccgga agttcgtgga   900
cacgacctcc gaccactcgg cgtacagctc gtccaggccg cgcacccaca cccaggccag   960
ggtgttgtcc ggcaccatct ggtcctggac cgcgctgatg aacagggtca cgtcgtcccg  1020
gaccacaccg gcgaagtcgt cctccacgaa gtccgggag aacccgagcc ggtcggtcca  1080
gaactcgacc gctccggcga cgtcgcgcgc ggtgagcacc ggaacggcac tggtcaactt  1140
ggccatggtt tagttcctca ccttgtcgta ttatactatg ccgatatact atgccgatga  1200
ttaattgtca acacgtgctg atcagatccg aaaatggata tacaagctcc cgggagcttt  1260
ttgcaaaagc ctaggcctcc aaaaaagcct cctcactact tctggaatag ctcagaggca  1320
gaggcggcct cggcctctgc ataaataaaa aaaattagtc agccatgggg cggagaatgg  1380
gcggaactgg gcggagttag gggcgggatg ggcggagtta ggggcgggac tatggttgct  1440
gactaattga gatgcatgct ttgcatactt ctgcctgctg gggagcctgg ggactttcca  1500
cacctggttg ctgactaatt gagatgcatg ctttgcatac ttctgcctgc tggggagcct  1560
ggggactttc cacaccctaa ctgacacaca ttccacagcc gaaggcgaa ttaacgctag   1620 catggatgtt ttcccagtca cgacgttgta aaacgacggc cagtcttaag ctcgggcccc  1680
aaataatgat ttattttga ctgatagtga cctgttcgtt gcaacaaatt gatgagcaat  1740
gcttttttat aatgccaact ttgtacaaaa aagcaggctt taaggaacc aattcagtcg   1800 actggatccg gtaccggcc cccctcgaa gatctaatat ttgcatgtcg ctatgtgttc   1860
tgggaaatca ccataaacgt gaaatcccta tcagtgatag agacttataa gttccctatc  1920
agtgatagag acaccgcttt gaacaggtag tgaatgtgcc cgaaagggcg tcatcattca  1980
```

```
ctacctgttc aaagcttttt tgtcgagctt ccttcgggaa gctctccata ttttttggat    2040
ccactagttc tagacccagc tttcttgtac aaagttggca ttataagaaa gcattgctta    2100
tcaatttgtt gcaacgaaca ggtcactatc agtcaaaata aaatcattat ttgccatcca    2160
gctgatatcc cctatagtga gtcgtattac atggtcatag ctgtttcctg gcagctctgg    2220
cccgtgtctc aaaatctctg atgttacatt gcacaagata aaatatatc atcatgaaca     2280 ataaaactgt ctgcttacat aaacagtaat acaaggggtg ttatgagcca tattcaacgg    2340
gaaacgtcga ggccgcgatt aaattccaac atggatgctg atttatatgg gtataaatgg    2400
gctcgcgata atgtcgggca atcaggtgcg acaatctatc gcttgtatgg aagcccgat    2460 gcgccagagt tgtttctgaa acatggcaaa ggtagcgttg ccaatgatgt tacagatgag    2520
atggtcagac taaactggct gacggaattt atgcctcttc cgaccatcaa gcattttatc    2580
cgtactcctg atgatgcatg gttactcacc actgcgatcc ccggaaaaac agcattccag    2640
gtattagaag aatatcctga ttcaggtgaa aatattgttg atgcgctggc agtgttcctg    2700
cgccggttgc attcgattcc tgtttgtaat tgtccttttta acagcgatcg cgtatttcgt    2760
ctcgctcagg cgcaatcacg aatgaataac ggtttggttg atgcgagtga ttttgatgac    2820
gagcgtaatg ctggcctgt tgaacaagtc tggaaagaaa tgcataaact tttgccattc     2880
tcaccggatt cagtcgtcac tcatggtgat ttctcacttg ataaccttat ttttgacgag    2940
gggaaattaa taggttgtat tgatgttgga cgagtcggaa tcgcagaccg ataccaggat    3000
cttgccatcc tatggaactg cctcggtgag ttttctcctt cattacagaa acggcttttt    3060
caaaaatatg gtattgataa tcctgatatg aataaattgc agtttcattt gatgctcgat    3120 gagttttct aatcagaatt ggttaattgg ttgtaacact ggcagagcat acgctgact     3180 tgacgggacg gcgcaagctc atgaccaaaa tcccttaacg tgagttacgc gtcgttccac    3240
tgagcgtcag accccgtaga aaagatcaaa ggatcttctt gagatccttt ttttctgcgc    3300
gtaatctgct gcttgcaaac aaaaaaacca ccgctaccag cggtggtttg tttgccggat    3360
caagagctac caactctttt tccgaaggta actggcttca gcagagcgca gataccaaat    3420
actgttcttc tagtgtagcc gtagttaggc caccacttca agaactctgt agcaccgcct    3480
acatacctcg ctctgctaat cctgttacca gtggctgctg ccagtggcga taagtcgtgt    3540
cttaccgggt tggactcaag acgatagtta ccggataagg cgcagcggtc gggctgaacg    3600
gggggttcgt gcacacagcc cagcttggag cgaacgacct acaccgaact gagataccta    3660
cagcgtgagc tatgagaaag cgccacgctt cccgaaggga gaaaggcgga caggtatccg    3720
gtaagcggca gggtcggaac aggagagcgc acgagggagc ttccaggggg aaacgcctgg    3780
tatctttata gtcctgtcgg gtttcgccac ctctgacttg agcgtcgatt tttgtgatgc    3840
tcgtcagggg gcggagcct atggaaaaac gccagcaacg cggcctttt acggttcctg     3900 gccttttgct ggccttttgc tcacatgtt                                      3929
```

<210> SEQ ID NO 53
<211> LENGTH: 64
<212> TYPE: DNA
<213> ORGANISM: Artificial
<220> FEATURE:
<223> OTHER INFORMATION: BoxC/D mut Bcl-xL Top strand

<400> SEQUENCE: 53

```
caccgctttg aacaggtagt gaatgtgccc gaaagggcgt catcattcac tacctgttca       60
```

```
aagc                                                              64

<210> SEQ ID NO 54
<211> LENGTH: 64
<212> TYPE: DNA
<213> ORGANISM: Artificial
<220> FEATURE:
<223> OTHER INFORMATION: BoxC/D mut Bcl-xL Bottom strand

<400> SEQUENCE: 54
aaaagctttg aacaggtagt gaatgatgac gcccttccgg gcacattcac tacctgttca    60
aagc                                                              64

<210> SEQ ID NO 55
<211> LENGTH: 3926
<212> TYPE: DNA
<213> ORGANISM: Artificial
<220> FEATURE:
<223> OTHER INFORMATION: pENTR/H1/TO-shRNA-Bcl-xL

<400> SEQUENCE: 55
ctttcctgcg ttatccctg attctgtgga taaccgtatt accgcctttg agtgagctga      60
taccgctcgc cgcagccgaa cgaccgagcg cagcgagtca gtgagcgagg aagcggaaga   120
gcgcccaata cgcaaaccgc ctctccccgc gcgttggccg attcattaat gcagctggca   180
cgacaggttt cccgactgga aagcgggcag tgagcgcaac gcaattaata cgcgtaccgc   240
tagccaggaa gagtttgtag aaacgcaaaa aggccatccg tcaggatggc cttctgctta   300
gtttgatgcc tggcagttta tggcgggcgt cctgcccgcc accctccggg ccgttgcttc   360
acaacgttca atccgctccc ggcggatttg tcctactcag ggagagcgtt caccgacaaa   420
caacagataa aacgaaaggc ccagtcttcc gactgagcct ttcgttttat ttgatgcctg   480
gcagttccct actctcgcgt taattcgccc ttagacatga agatacat tgatgagttt    540 ggacaaacca caactagaat gcagtgaaaa aaatgcttta tttgtgaaat ttgtgatgct   600
attgctttat ttgtaaccat tataagctgc aataaacaag ttggggtggg cgaagaactc   660
cagcatgaga tccccgcgct ggaggatcat ccagccggcg tccggaaaaa cgattccgaa   720
gcccaacctt tcatagaagg cggcggtgga atcgaaatct cgtagcacgt gtcagtcctg   780
ctcctcggcc acgaagtgca cgcagttgcc ggccgggtcg cgcagggcga actcccgccc   840
ccacggctgc tcgccgatct cggtcatggc cggcccggag gcgtcccgga agttcgtgga   900
cacgacctcc gaccactcgg cgtacagctc gtccaggccg cgcacccaca cccaggccag   960
ggtgttgtcc ggcaccatct ggtcctggac cgcgctgatg aacagggtca cgtcgtcccg  1020
gaccacaccg gcgaagtcgt cctccacgaa gtcccgggag aacccgagcc ggtcggtcca  1080
gaactcgacc gctccggcga cgtcgcgcgc ggtgagcacc ggaacggcac tggtcaactt  1140
ggccatggtt tagttcctca ccttgtcgta ttatactatg ccgatatact atgccgatga  1200
ttaattgtca acacgtgctg atcagatccg aaaatggata tacaagctcc cgggagcttt  1260
ttgcaaaagc ctaggcctcc aaaaaagcct cctcactact tctggaatag ctcagaggca  1320
gaggcggcct cggcctctgc ataaataaaa aaaattagtc agccatgggg cggagaatgg  1380
gcggaactgg gcggagttag gggcgggatg ggcggagtta ggggcgggac tatggttgct  1440
gactaattga gatgcatgct ttgcatactt ctgcctgctg gggagcctgg gactttcca   1500 cacctggttg ctgactaatt gagatgcatg ctttgcatac ttctgcctgc tggggagcct  1560
ggggactttc cacacccctaa ctgacacaca ttccacagcc gaagggcgaa ttaacgctag  1620
```

-continued

```
catggatgtt ttcccagtca cgacgttgta aaacgacggc cagtcttaag ctcgggcccc    1680
aaataatgat tttattttga ctgatagtga cctgttcgtt gcaacaaatt gatgagcaat    1740
gcttttttat aatgccaact ttgtacaaaa aagcaggctt taaaggaacc aattcagtcg    1800
actggatccg gtaccgggcc cccctcgaa gatctaatat ttgcatgtcg ctatgtgttc     1860
tgggaaatca ccataaacgt gaaatcccta tcagtgatag agacttataa gttccctatc    1920
agtgatagag acaccgcttt gaacaggtag tgaatgaact agcatagagt tcattcacta    1980
cctgttcaaa gcttttttgt cgagcttcct tcgggaagct ctccatatt tttggatcca    2040 ctagttctag acccagcttt cttgtacaaa gttggcatta taagaaagca ttgcttatca    2100
atttgttgca acgaacaggt cactatcagt caaaataaaa tcattatttg ccatccagct    2160
gatatcccct atagtgagtc gtattacatg gtcatagctg tttcctggca gctctggccc    2220
gtgtctcaaa atctctgatg ttacattgca caagataaaa atatatcatc atgaacaata    2280
aaactgtctg cttacataaa cagtaataca aggggtgtta tgagccatat tcaacgggaa    2340
acgtcgaggc cgcgattaaa ttccaacatg gatgctgatt tatatgggta taaatgggct    2400
cgcgataatg tcgggcaatc aggtgcgaca atctatcgct tgtatgggaa gcccgatgcg    2460
ccagagttgt ttctgaaaca tggcaaaggt agcgttgcca atgatgttac agatgagatg    2520
gtcagactaa actggctgac ggaatttatg cctcttccga ccatcaagca ttttatccgt    2580
actcctgatg atgcatggtt actcaccact gcgatcccg gaaaaacagc attccaggta    2640
ttagaagaat atcctgattc aggtgaaaat attgttgatg cgctggcagt gttcctgcgc    2700
cggttgcatt cgattcctgt ttgtaattgt ccttttaaca gcgatcgcgt atttcgtctc    2760
gctcaggcgc aatcacgaat gaataacggt ttggttgatg cgagtgattt tgatgacgag    2820
cgtaatggct ggcctgttga acaagtctgg aaagaaatgc ataaactttt gccattctca    2880
ccggattcag tcgtcactca tggtgatttc tcacttgata accttatttt tgacgagggg    2940
aaattaatag gttgtattga tgttggacga gtcggaatcg cagaccgata ccaggatctt    3000
gccatcctat ggaactgcct cggtgagttt tctccttcat tacagaaacg gcttttttcaa   3060 aaaatatggta ttgataatcc tgatatgaat aaattgcagt ttcatttgat gctcgatgag    3120 ttttttctaat cagaattggt taattggttg taacactggc agagcattac gctgacttga    3180
cgggacggcg caagctcatg accaaaatcc cttaacgtga gttacgcgtc gttccactga    3240
gcgtcagacc ccgtagaaaa gatcaaagga tcttcttgag atcctttttt tctgcgcgta    3300
atctgctgct tgcaaacaaa aaaaccaccg ctaccagcgg tggtttgttt gccggatcaa    3360
gagctaccaa ctctttttcc gaaggtaact ggcttcagca gagcgcagat accaaatact    3420
gttcttctag tgtagccgta gttaggccac cacttcaaga actctgtagc accgcctaca    3480
tacctcgctc tgctaatcct gttaccagtg gctgctgcca gtggcgataa gtcgtgtctt    3540
accgggttgg actcaagacg atagttaccg gataaggcgc agcggtcggg ctgaacgggg    3600
ggttcgtgca cacagcccag cttggagcga acgacctaca ccgaactgag atacctacag    3660
cgtgagctat gagaaagcgc cacgcttccc gaagggagaa aggcggacag gtatccggta    3720
agcggcaggg tcggaacagg agagcgcacg agggagcttc caggggggaaa cgcctggtat    3780 ctttatagtc ctgtcgggtt tcgccacctc tgacttgagc gtcgattttt gtgatgctcg    3840
tcaggggggc ggagcctatg gaaaaacgcc agcaacgcgg cctttttacg gttcctggcc    3900
ttttgctggc cttttgctca catgtt                                         3926
```

<210> SEQ ID NO 56
<211> LENGTH: 61
<212> TYPE: DNA
<213> ORGANISM: Artificial
<220> FEATURE:
<223> OTHER INFORMATION: Bcl-xL Top strand

<400> SEQUENCE: 56

```
caccgctttg aacaggtagt gaatgaacta gcatagagtt cattcactac ctgttcaaag    60
c                                                                   61
```

<210> SEQ ID NO 57
<211> LENGTH: 61
<212> TYPE: DNA
<213> ORGANISM: Artificial
<220> FEATURE:
<223> OTHER INFORMATION: Bcl-xL Bottom strand

<400> SEQUENCE: 57

```
aaaagctttg aacaggtagt gaatgaactc tatgctagtt cattcactac ctgttcaaag    60
c                                                                   61
```

<210> SEQ ID NO 58
<211> LENGTH: 6173
<212> TYPE: DNA
<213> ORGANISM: Artificial
<220> FEATURE:
<223> OTHER INFORMATION: pcDNA-AmCyan-myc-His6

<400> SEQUENCE: 58

```
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca caaggcaag gcttgaccga caattgcatg aagaatctgc    180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagt   900
taagcttggt accgagctcg gatccactag tccagtgtgg tggaattccc accatggctc   960
tttcaaacaa gttatcggag atgacatgaa aatgacctac catatggatg gctgtgtca   1020
atgggcatta ctttaccgtc aaaggtgaag gcagcgggaa gccatacgaa gggacgcaga  1080
cctcgacttt taagtcacc atggccaacg tgggccct tgcattctcc tttgacatac    1140
tatctacagt gttcatgtat ggaaatcgat gctttactgc gtatcctacc agtatgcccg  1200
actatttcaa acaagcattt cctgacggaa tgtcatgatga aaggactttt acctatgaag  1260
```

```
atggaggagt tgctacagcc agttgggaaa taagccttaa aggcaactgc tttgagcaca    1320
aatccacgtt tcatggagtg aactttcctg ctgatggacc tgtgatggcg aagatgacaa    1380
ctggttggga cccatctttt gagaaaatga ctgtctgcga tggaatattg aagggtgatg    1440
tcaccgcgtt cctcatgctg caaggaggtg gcaattacag atgccaattc cacacttctt    1500
acaagacaaa aaaaccggtg acgatgccac caaaccatgc ggtggaacat cgcattgcga    1560
ggaccgacct tgacaaaggt ggcaacagtg ttcagctgac ggagcacgct gttgcacata    1620
taacctctgt tgtccctttc gaagggcggc cgcaactcga gtctagaggg cccttcgaac    1680
aaaaactcat ctcagaagag gatctgaata tgcataccgg tcatcatcac catcaccatt    1740
gagtttaaac ccgctgatca gcctcgactg tgccttctag ttgccagcca tctgttgttt    1800
gcccctcccc cgtgccttcc ttgacccctgg aaggtgccac tcccactgtc ctttcctaat    1860
aaaatgagga aattgcatcg cattgtctga gtaggtgtca ttctattctg ggggtggggg    1920
tggggcagga cagcaagggg gaggattggg aagacaatag caggcatgct ggggatgcgg    1980
tgggctctat ggcttctgag gcggaaagaa ccagctgggg ctctaggggg tatccccacg    2040
cgccctgtag cggcgcatta gcgcggcgg gtgtggtggt tacgcgcagc gtgaccgcta    2100
cacttgccag cgccctagcg cccgctcctt tcgctttctt cccttccttt ctcgccacgt    2160
tcgccggctt tccccgtcaa gctctaaatc ggggggctccc tttagggttc cgatttagtg    2220
ctttacggca cctcgacccc aaaaaacttg attagggtga tggttcacgt agtgggccat    2280
cgccctgata gacggttttt cgccctttga cgttggagtc cacgttcttt aatagtggac    2340
tcttgttcca aactggaaca acactcaacc ctatctcggt ctattctttt gatttataag    2400
ggattttgcc gatttcggcc tattggttaa aaaatgagct gatttaacaa aaatttaacg    2460
cgaattaatt ctgtggaatg tgtgtcagtt agggtgtgga aagtccccag gctccccagc    2520
aggcagaagt atgcaaagca tgcatctcaa ttagtcagca accaggtgtg aaagtccccc    2580
aggctcccca gcaggcagaa gtatgcaaag catgcatctc aattagtcag caaccatagt    2640
cccgccccta actccgccca tcccgcccct aactccgccc agttccgccc attctccgcc    2700
ccatggctga ctaatttttt ttatttatgc agaggccgag gccgcctctg cctctgagct    2760
attccagaag tagtgaggag gctttttttgg aggcctaggc ttttgcaaaa agctcccggg    2820
agcttgtata tccattttcg gatctgatca agagacagga tgaggatcgt ttcgcatgat    2880
tgaacaagat ggattgcacg caggttctcc ggccgcttgg gtggagaggc tattcggcta    2940
tgactgggca caacagacaa tcggctgctc tgatgccgcc gtgttccggc tgtcagcgca    3000
ggggcgcccg gttcttttg tcaagaccga cctgtccggt gccctgaatg aactgcagga    3060
cgaggcagcg cggctatcgt ggctggccac gacgggcgtt ccttgcgcag ctgtgctcga    3120
cgttgtcact gaagcgggaa gggactggct gctattgggc gaagtgccgg ggcaggatct    3180
cctgtcatct caccttgctc ctgccgagaa agtatccatc atggctgatg caatgcggcg    3240
gctgcatacg cttgatccgg ctacctgccc attcgaccac caagcgaaac atcgcatcga    3300
gcgagcacgt actcggatgg aagccggtct tgtcgatcag gatgatctgg acgaagagca    3360
tcaggggctc gcgccagccg aactgttcgc caggctcaag gcgcgcatgc ccgacggcga    3420
ggatctcgtc gtgacccatg gcgatgcctg cttgccgaat atcatggtgg aaaatggccg    3480
cttttctgga ttcatcgact gtggccggct gggtgtggcg gaccgctatc aggacatagc    3540
gttggctacc cgtgatattg ctgaagagct tggcggcgaa tgggctgacc gcttcctcgt    3600
```

```
gctttacggt atcgccgctc ccgattcgca gcgcatcgcc ttctatcgcc ttcttgacga    3660
gttcttctga gcgggactct ggggttcgcg aaatgaccga ccaagcgacg cccaacctgc    3720
catcacgaga tttcgattcc accgccgcct tctatgaaag gtttgggcttc ggaatcgttt   3780 tccgggacgc cggctggatg atcctccagc gcggggatct catgctggag ttcttcgccc    3840
accccaactt gtttattgca gcttataatg gttacaaata aagcaatagc atcacaaatt    3900
tcacaaataa agcatttttt tcactgcatt ctagttgtgg tttgtccaaa ctcatcaatg    3960
tatcttatca tgtctgtata ccgtcgacct ctagctagag cttggcgtaa tcatggtcat    4020
agctgtttcc tgtgtgaaat tgttatccgc tcacaattcc acacaacata cgagccggaa    4080
gcataaagtg taaagcctgg ggtgcctaat gagtgagcta actcacatta attgcgttgc    4140
gctcactgcc cgctttccag tcgggaaacc tgtcgtgcca gctgcattaa tgaatcggcc    4200
aacgcgcggg gagaggcggt ttgcgtattg ggcgctcttc cgcttcctcg ctcactgact    4260
cgctgcgctc ggtcgttcgg ctgcggcgag cggtatcagc tcactcaaag gcggtaatac    4320
ggttatccac agaatcaggg gataacgcag gaaagaacat gtgagcaaaa ggccagcaaa    4380
aggccaggaa ccgtaaaaag gccgcgttgc tggcgttttt ccataggctc cgcccccctg    4440
acgagcatca caaaaatcga cgctcaagtc agaggtggcg aaacccgaca ggactataaa    4500
gataccaggc gtttccccct ggaagctccc tcgtgcgctc tcctgttccg accctgccgc    4560
ttaccggata cctgtccgcc tttctccctt cgggaagcgt ggcgctttct catagctcac    4620
gctgtaggta tctcagttcg gtgtaggtcg ttcgctccaa gctgggctgt gtgcacgaac    4680
cccccgttca gcccgaccgc tgcgccttat ccggtaacta tcgtcttgag tccaacccgg    4740
taagacacga cttatcgcca ctggcagcag ccactggtaa caggattagc agagcgaggt    4800
atgtaggcgg tgctacagag ttcttgaagt ggtggcctaa ctacggctac actagaagaa    4860
cagtatttgg tatctgcgct ctgctgaagc cagttacctt cggaaaaaga gttggtagct    4920
cttgatccgg caaacaaacc accgctggta gcggtggttt ttttgtttgc aagcagcaga    4980
ttacgcgcag aaaaaaagga tctcaagaag atcctttgat cttttctacg gggtctgacg    5040
ctcagtggaa cgaaaactca cgttaaggga ttttggtcat gagattatca aaaaggatct    5100
tcacctagat ccttttaaat taaaaatgaa gttttaaatc aatctaaagt atatatgagt    5160
aaacttggtc tgacagttac caatgcttaa tcagtgaggc acctatctca gcgatctgtc    5220
tatttcgttc atccatagtt gcctgactcc ccgtcgtgta gataactacg atacgggagg    5280
gcttaccatc tggccccagt gctgcaatga taccgcgaga cccacgctca ccggctccag    5340
atttatcagc aataaaccag ccagccggaa gggccgagcg cagaagtggt cctgcaactt    5400
tatccgcctc catccagtct attaattgtt gccgggaagc tagagtaagt agttcgccag    5460
ttaatagttt gcgcaacgtt gttgccattg ctacaggcat cgtggtgtca cgctcgtcgt    5520
ttggtatggc ttcattcagc tccggttccc aacgatcaag gcgagttaca tgatccccca    5580
tgttgtgcaa aaaagcggtt agctccttcg gtcctccgat cgttgtcaga agtaagttgg    5640
ccgcagtgtt atcactcatg gttatggcag cactgcataa ttctcttact gtcatgccat    5700
ccgtaagatg cttttctgtg actggtgagt actcaaccaa gtcattctga atagtgta     5760 tgcggcgacc gagttgctct tgcccggcgt caatacggga taataccgcg ccacatagca    5820
gaactttaaa agtgctcatc attggaaaac gttcttcggg gcgaaaactc tcaaggatct    5880
taccgctgtt gagatccagt tcgatgtaac ccactcgtgc acccaactga tcttcagcat    5940
cttttacttt caccagcgtt tctgggtgag caaaaacagg aaggcaaaat gccgcaaaaa    6000
```

-continued

```
agggaataag ggcgacacgg aaatgttgaa tactcatact cttccttttt caatattatt    6060
gaagcattta tcagggttat tgtctcatga gcggatacat atttgaatgt atttagaaaa    6120
ataaacaaat aggggttccg cgcacatttc cccgaaaagt gccacctgac gtc           6173
```

CONSTRUCTION OF PROTEIN-RESPONSIVE SHRNA/RNAI CONTROL SYSTEM USING RNP MOTIF

TECHNICAL FIELD

The present invention relates to the construction of a protein-responsive shRNA and RNAi control system using an RNP motif.

BACKGROUND ART

RNA interference (hereinafter, referred to as RNAi) is a phenomenon in which translation is transiently inhibited by cleaving mRNA in a sequence-specific manner. An approach called knockdown, which causes this RNAi by introducing an RNA duplex such as short hairpin RNA (hereinafter, referred to as shRNA), has been established in various organism species. RNAi has been diffused widely, including study on its application to medical treatment, in a period as short as 10 years from its discovery as the convenient and potent approach of transiently inhibiting gene expression. However, its mechanisms or introduction techniques still remain to be evolved. Moreover, at this time, the theme of RNAi centers on studies for making knockdown strongly effective or the development of delivery techniques for delivering RNA to a site of interest.

Chung et al. have prepared artificial RNA in which the binding site of theophylline known as a caffeine-like low-molecular-weight compound has been introduced in the loop portion of shRNA, and have revealed that RNAi is inhibited in a theophylline concentration-dependent manner (see Non-Patent Document 1).

Non-Patent Document 1: Chung-Il An, Vu B. Trinh, and Yohei Yokobayashi, RNA, May 2006; 12: 710-716

DISCLOSURE OF THE INVENTION

Problems to be Solved by the Invention

An object of the present invention is to provide an RNAi control system using RNP for the purpose of newly designing and preparing a translational control mechanism using RNAs or proteins as inhibitors and incorporating such an artificial translational control system into a living body.

Means for Solving the Problems

The present invention has been achieved for attaining the object. Specifically, according to one embodiment, the present invention relates to an shRNA comprising: a guide strand having a sequence complementary to a target sequence; a passenger strand which forms a duplex with the guide strand; and a linker strand which links the guide strand and the passenger strand, wherein the linker strand comprises an RNP-derived protein-binding motif sequence. In the present specification, this shRNA is also referred to as a sensor shRNA.

It is preferred that the RNP-derived protein-binding motif sequence should be a Box C/D sequence.

According to an alternative aspect, the present invention relates to an RNAi control system comprising: the sensor shRNA; and an RNP-derived protein which specifically binds to a protein-binding motif sequence in the shRNA.

According to an alternative aspect, the present invention relates to an RNAi control system comprising: a vector for expression of the sensor shRNA; and a vector for expression of an RNP-derived protein which specifically binds to a protein-binding motif sequence in the shRNA.

According to a further alternative aspect, the present invention relates to an RNAi control method comprising the steps of: contacting the sensor shRNA with an RNP-derived protein which specifically binds to a protein-binding motif sequence in the shRNA, in a solution; and introducing the solution containing the shRNA and the protein into a cell.

According to a further alternative aspect, the present invention relates to an intracellular RNAi control method comprising the steps of: introducing a vector for expression of the sensor shRNA into a cell; introducing a vector for expression of an RNP-derived protein which specifically binds to a protein-binding motif sequence in the shRNA, into the cell; and causing their expressions from the vector for expression of the shRNA and the vector for expression of the protein.

According to a further alternative aspect, the present invention provides an RNAi control system responsive to a protein expressed in a cell, the system comprising: the sensor shRNA in which RNP-derived protein-binding motif sequence is a sequence specifically binding to the protein expressed in the cell, or a vector for expression of the shRNA, and also provides an RNAi control method responsive to a protein expressed in a cell, the method comprising the step of: introducing the sensor shRNA in which RNP-derived protein-binding motif sequence is a sequence specifically binding to the protein expressed in the cell, or a vector for expression of the shRNA, into a cell.

According to a further alternative aspect, the present invention provides the RNAi control system which controls the expression of an apoptosis regulatory protein wherein the target sequence of the shRNA is Bcl-xL mRNA, and also provides an artificial protein information conversion system using the shRNA, wherein information of a protein specifically binding to an RNP-derived protein-binding motif sequence is converted to information of a protein encoded by an RNA of the target sequence of the shRNA.

Advantageous Effects of the Invention

As an advantageous effects of the present invention, use of the sensor shRNA described above enables RNAi control such that RNAi is inhibited in a manner dependent on a protein specifically binding to the shRNA. This means that in the presence of the sensor shRNA, use of a particular protein as an input signal can inhibit the RNAi of particular mRNA and relatively increase the amount of proteins expressed from the particular mRNA. The sensor shRNA according to the present invention used in combination with the particular protein is useful in the construction of biosensors for quantifying the expression of intracellular marker proteins without destroying cells or artificial gene circuits capable of activating the translation of proteins of interest in response to the expression level of marker proteins. For example, the present invention produces significant advantageous effects that lead to the treatment of diseases such as cancer or Alzheimer's disease by activating apoptosis-inducing proteins in response to the expression of cancer marker proteins.

BRIEF DESCRIPTION OF THE DRAWINGS

In FIGS. 5(A) to 5(D), the wedge-shaped mark represents the position of cleavage by Dicer;

FIG. 11 is a graph showing results of FACS-analyzing fluorescence intensity distribution in Example 2;

FIG. 13(A) shows the secondary structure sequence of shRNA-Bc1xL for Bc1xL knockdown (SEQ ID NO:47), FIG. 13(B) shows the secondary structure sequence of shRNA-Box C/D-Bc1xL that is expected to specifically bind at the Box C/D sequence to an L7Ae protein (SEQ ID NO:45), and FIG. 13(C) shows the secondary structure sequence of shRNA-Box C/D mut-Bc1xL that does not bind to L7Ae (SEQ ID NO:59). In FIGS. 13(A) to 13(C), the arrowheads indicate Dicer cleavage site;

Figure 1:
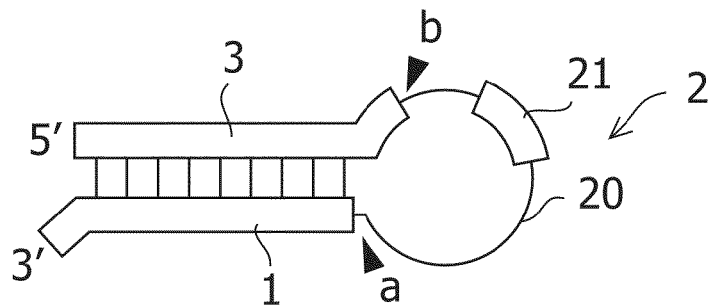
FIG. 1 schematically shows an shRNA according to the first embodiment.

DESCRIPTION OF SYMBOLS 1 guide strand
2 linker strand
20 base sequence
21 protein-binding motif sequence
3 passenger strand
4 protein
a Dicer cleavage site
b Dicer cleavage site
1d guide strand-encoding DNA sequence
2d linker strand-encoding DNA sequence
3d passenger strand-encoding DNA sequence

BEST MODE FOR CARRYING OUT THE INVENTION

Hereinafter, the present invention will be described in detail with reference to embodiments. However, the present invention is not intended to be limited to the description below.

In recent years, various noncoding RNAs that function in vivo have been discovered, and their roles have received attention. However, these RNAs often form a complex with a protein (RNP) in vivo. Thus, artificial RNP has been expected as a novel nanoblock capable of controlling cell functions. Naturally occurring RNP is found to form many complexes using an RNA-protein interaction motif (RNP motif) composed of a relatively short sequence. For example, HIV Rev proteins interact with high affinity with RNA motifs that recognize Rev. Thus, RNP has been expected to be used as a research material for synthetic biology (field in which biological molecules or the systems of life are constituted through the procedures of artificially creating biological molecules to induce new technologies).

To develop a system for controlling the translation of proteins of interest in response to proteins expressed in cells, the present inventors have come up with the idea that RNA interference is controlled using this RNA-protein interaction motif, thereby controlling the translation of proteins of interest. Based on this idea, the present invention has been completed.

According to a first embodiment, the present invention provides an shRNA comprising: a guide strand having a sequence complementary to a target sequence; a passenger strand which forms a duplex with the guide strand; and a linker strand which links the guide strand and the passenger strand, wherein the linker strand comprises an RNP-derived protein-binding motif sequence.

The shRNA according to the first embodiment is schematically shown in FIG. 1. The shRNA according to the first embodiment comprises a guide strand 1, a linker strand 2, and a passenger strand 3 in this order from the 3' end. The linker strand 2 has an RNP-derived protein-binding motif sequence 21 in the strand.

The guide strand 1 may be an RNA nucleotide sequence of approximately 21 bases to 26 bases and may be located at the 3' end in the shRNA. The guide strand 1 has a sequence complementary to a particular sequence of mRNA to be controlled (hereinafter, referred to as a target sequence). The mRNA to be controlled can be selected appropriately by those skilled in the art according to the purpose. Examples of the mRNA to be controlled include, but not limited to, mRNAs of apoptosis-inducing genes, mRNAs of apoptosis-suppressing genes, and mRNAs of cancer marker genes. More specific examples of the mRNA to be controlled include GFP mRNA, BimEL mRNA, and Bc1-xL mRNA. Moreover, in these mRNAs, a sequence used as the target sequence can be selected appropriately by those skilled in the art by using design software based on information about the constitution and type of its primary gene sequence in view of inhibited off-target effect and the more efficiently inhibited expression of the target gene. The guide strand must be completely complementary to the target sequence. This is to cause the RNAi effect. At least 2 bases of the 3'-terminal in the guide strand 1 may form overhang that does not form complementary strands with the passenger strand. The guide strand 1 is a portion that becomes siRNA after cleavage by Dicer.

The passenger strand 3 may be an RNA nucleotide sequence of approximately 21 bases to 26 bases and may be located at the 5' end of the shRNA. When the passenger strand 3 is, for example, of 21 bases, bases 3 to 21 from the 3' end of the passenger strand 3 have a sequence that forms complementary strands with bases 3 to 21 from the 3' end of the guide strand 1. When the passenger strand 3 is composed of 21 bases, usually, the guide strand is also composed of 21 bases. The numbers of bases constituting the passenger strand 3 and the guide strand 1 may be 22, 23, 24, 25, or 26. In either case, the numbers of bases of the passenger strand 3 and the guide strand 5 are usually equal. Moreover, as shown in FIG. 1, base 3 from the 3' end to the base at the 5' end of the passenger strand 3 has a sequence that forms complementary strands with the base at the 5' end to base 3 from the 3' end of the guide strand 1. In this case, the passenger strand may be permitted to contain a 1-base to 2-base mismatch to the guide strand. After cleavage by Dicer, the passenger strand 3 may have, at the 3' end, overhang of at least 2 bases that forms complementary strands neither with a portion of the guide strand 1 nor with a portion of the linker strand. The passenger strand 3 may be also a portion that becomes siRNA after cleavage by Dicer.

The linker strand 2 serves as a linker between the guide strand 1 and the passenger strand 3. The linker strand 2 may be bound to the 5' end of the guide strand 1 and the 3' end of the passenger strand 3. In other words, the linker strand 2 may be a portion that is cleaved off from the guide strand 1 and the passenger strand 3 after cleavage by Dicer. The linker strand 2 may constitute the major part of the nonhybridized loop portion, as shown in the drawing, in the sensor shRNA according to the present invention. A portion of the nonhybridized loop portion may be derived from a portion of the 3' end of the passenger strand 3. Alternatively, the linker strand 2 may constitute the whole nonhybridized loop portion, and a few bases at the 3' end of the linker strand 2 and a few bases at the 5' end of the linker strand 2 may form a portion of the stem portion of the hairpin structure through hybridization therebetween, though this structure is not shown in the drawings.

The linker strand 2 may comprise a base sequence 20 and an RNP-derived protein-binding motif sequence 21. In this context, the base sequence 20 in the present invention refers to a portion of the sequence constituting the linker strand and a portion that is not derived from the RNP-derived protein-binding motif sequence 21. In another embodiment, the linker strand 2 may be composed only of the RNP-derived protein-binding motif sequence 21. When the linker strand 2 comprises the base sequence 20 and the RNP-derived protein-binding motif sequence 21 or when the linker strand 2 is composed only of the RNP-derived protein-binding motif sequence 21, the linker strand 2 may have, in its sequence, a sequence that does not form complementary strands, and this sequence may constitute the loop portion of the shRNA. The sequence that does not form complementary strands may be of 4 to 20 bases, preferably 4 to 11 bases, and the types of the bases are not limited. Preferable examples of the sequence that does not directly form complementary strands include, but not limited to, 5'-AGCAUAG-3' and 5'-GAAA-3'.

The 3'-terminal 2 bases of the linker strand 2 may form complementary strands with the 3'-terminal 2 bases of the passenger strand 3. Furthermore, bases 3 to 7 bases may from the 3' end of the linker strand 2 may form complementary strands with bases 1 to 4 from the 5' end of the linker strand 2. In this case, the number of bases forming complementary strands is 4. However, this number is not limited to 4 and can be determined between 1 and 8 bases.

When the protein-binding motif sequence 21 is introduced to the base sequence 20, the introduction position of the protein-binding motif sequence 21 is not limited and may be a range which maintains recognition by Dicer described later. Moreover, when the linker strand is free from the base sequence, the protein-binding motif sequence 21 can be bound directly to the guide strand 1 and the passenger strand 3.

In this context, examples of the protein-binding motif sequence 21 include nucleotide sequences derived from RNA-protein complex interaction motifs (RNP motifs), and nucleotide sequences mutated from these nucleotide sequences. In the present invention, the nucleotide sequences derived from RNA-protein complex interaction motifs encompass: nucleotide sequences known as the RNA sequences of RNA-protein interaction motifs in known natural RNA-protein complexes; and nucleotide sequences as the RNA sequences of artificial RNA-protein complex interaction motifs obtained by an in-vitro evolution method. The RNA-protein complexes are a large number of associates of proteins and RNAs that have been confirmed in vivo, and are 3D objects having a complicated structure. The nucleotide sequences derived from natural RNA-protein complex interaction motifs are usually composed of approximately 10 to 80 bases and known to form specific binding in a noncovalent manner, i.e., through a hydrogen bond, with a particular amino acid sequence of a particular protein. Such nucleotide sequences derived from natural RNA-protein complex interaction motifs can be selected from Tables 1 and 2 below and the database: http://gibk26.bse.kyutech.acjp/jouhou/image/dna-protein/rna/ma.html that is available on the website. The protein-binding motif sequence 21 as an RNA-protein interaction motif-derived nucleotide sequence preferably used in the present embodiment is a sequence that can be recognized by Dicer described below in detail to cause RNAi when incorporated in the shRNA. For conformational conditions, it is preferred that such a protein-binding motif sequence 21 should form a characteristic RNA tertiary structure comprising nonnatural base pairs and be highly specific for a protein binding to this site. Moreover, it is preferred that the RNA-protein interaction motif should have Kd of, but not limited to, approximately 0.1 nM to approximately 1 μM.

TABLE 1

| RNA name | Protein name | Kd | Document |
|---|---|---|---|
| 5S RNA (*Xenopus laevis* oocyte) | 5R1 | 0.64 ± 0.10 nM | Nat Struct Biol. 1998 Jul; 5(7): 543-6 |
| 5S RNA (*Xenopus laevis* oocyte) | 5R2 | 0.35 ± 0.03 nM | Nat Struct Biol. 1998 Jul; 5(7): 543-6 |
| dsRNA | B2 | 1.4 ± 0.13 nM | Nat Struct Mol Biol. 2005 Nov; 12(11): 952-7 |
| RNA splicing motif with UGCAUGU element | Fox-1 | 0.49 nM at 150 mM salt | EMBO J. 2006 Jan 11; 25(1): 163-73. |
| TGE | GLD-1 | 9.2 ± 2 nM | J Mol Biol. 2005 Feb 11; 346(1): 91-104. |

TABLE 1-continued

| RNA name | Protein name | Kd | Document |
|---|---|---|---|
| sodB mRNA | Hfq | 1.8 nM | EMBO J. 2004 Jan 28; 23(2): 396-405. |
| RyhB (siRNA) | Hfq | 1500 nM | Annu Rev Microbiol. 2004; 58: 303-28 |
| mRNA | HuD | 0.7 ± 0.02 nM | Nat Struct Biol. 2001 Feb; 8(2): 141-5 |
| S domain of 7S RNA | human SRP19 | | RNA. 2005 Jul; 11(7): 1043-50. Epub 2005 May 31 |
| Large subunit of SRP RNA | human SRP19 | 2 nM | Nat Struct Biol. 2001 Jun; 8(6): 515-20 |
| 23S rRNA | L1 | | Nat Struct Biol. 2003 Feb; 10(2): 104-8 |
| 23S rRNA | L11 | | Nat Struct Biol. 2000 Oct; 7(10): 834-7 |
| 5S rRNA | L18 | | Biochem J. 2002 May 1; 363(Pt 3): 553-61 |
| 23S rRNA | L20 | 13 ± 2 nM | J Biol Chem. 2003 Sep 19; 278(38): 36522-30. |
| Own mRNA site1 | L20 | 88 ± 23 nM | J Biol Chem. 2003 Sep 19; 278(38): 36522-30. |
| Own mRNA site2 | L20 | 63 ± 23 nM | Mol Microbiol. 2005 Jun; 56(6): 1441-56 |
| 23S rRNA | L23 | | J Biomol NMR. 2003 Jun; 26(2): 131-7 |
| 5S rRNA | L25 | | EMBO J. 1999 Nov 15; 18(22): 6508-21 |
| Own mRNA | L30 | | Nat Struct Biol. 1999 Dec; 6(12): 1081-3. |
| mRNA | LicT | | EMBO J. 2002 Apr 15; 21(8): 1987-97 |
| Own mRNA | MS2 coat | 39 ± 5 nM | FEBS J. 2006 Apr; 273(7): 1463-75 |
| Stem-loop RNA motif | Nova-2 | | Cell. 2000 Feb 4; 100(3): 323-32 |
| SL2 | Nucleocapsid | 110 ± 50 nM | J Mol Biol. 2000 Aug 11; 301(2): 491-511 |
| Pre-rRNA | Nucleolin | | EMBO J. 2000 Dec 15; 19(24): 6870-81 |
| | p19 | 0.17 ± 0.02 nM | Cell. 2003 Dec 26; 115(7): 799-811 |
| Box C/D | L7Ae | 0.9 ± 0.2 nM | RNA. 2005 Aug; 11(8): 1192-200. |

TABLE 2

| RNA name | Protein name | Kd | Document |
|---|---|---|---|
| siRNA with the characteristic two-base 3' overhangs | PAZ (PiWi Argonaut and Zwille) | | Nat Struct Biol. 2003 Dec; 10(12): 1026-32. |
| dsRNA | Rnase III | | Cell. 2006 Jan 27; 124(2): 355-66 |
| HIV-1 RRE (IIB) | RR1-38 | 3-8 nM | Nat Struct Biol. 1998 Jul; 5(7): 543-6 |
| Own mRNA | S15 | 5 nM | EMBO J. 2003 Apr 15; 22(8): 1898-908 |
| 16S rRNA | S15 | 6 nM | Nat Struct Biol. 2000 Apr; 7(4): 273-277. |
| Own mRNA | S15 | 43 nM | EMBO J. 2003 Apr 15; 22(8): 1898-908 |
| 16S rRNA | S4 | 6.5 μM in 4° C., 1.7 nM in 42° C. | J Biol Chem. 1979 Mar 25; 254(6): 1775-7 |
| 16S rRNA | S4 | 18 μM | J Biol Chem. 1979 Mar 25; 254(6): 1775-7 |
| 16S rRNA | S8 | 26 ± 7 nM | J Mol Biol. 2001 Aug 10; 311(2): 311-24 |
| mRNA | S8 | 200 nM | RNA. 2004 Jun; 10(6): 954-64 |
| mRNA | SacY | 1400 nM | EMBO J. 1997 Aug 15; 16(16): 5019-29 |
| SnRNA | Sm | | Cold Spring Harb Symp Quant Biol. 2006; 71: 313-20. |
| tmRNA | SmpB | 21 ± 7 nM | J Biochem (Tokyo). 2005 Dec; 138(6): 729-39 |
| TD3 of tmRNA | SmpB | 650 nM | J Biochem (Tokyo). 2005 Dec; 138(6): 729-39 |
| U1 snRNA | snRNP U1A | 0.032 ± 0.007 nM (salt dependence) | Nat Struct Biol. 2000 Oct; 7(10): 834-7 |
| S domain of 7S RNA | SRP54 | 500 nM | RNA. 2005 Jul; 11(7): 1043-50. |
| TAR | Tat | 200-800 nM | Nucleic Acids Res. 1996 Oct 15; 24(20): 3974-81 |
| BIV TAR | Tat | 1.3 nM or 8 nM or 60 nM (depending on difference in Mg) | Mol Cell. 2000 Nov; 6(5): 1067-76 |
| tRNA$^{Thr}$ | ThrRS | 500 nM | Nat Struct Biol. 2002 May; 9(5): 343-7 |
| thrS mRNA operator | ThrRS | 10 nM | Trends Genet. 2003 Mar; 19(3): 155-61 |
| Single stranded mRNA | TIS11d | | Nat Struct Mol Biol. 2004 Mar; 11(3): 257-64. |
| PSTVd | Virp1 | 500 nM | Nucleic Acids Res. 2003 Oct 1; 31(19): 5534-43 |
| RNA hairpin; Smaug recognition element (SRE) | Vts1p | 30 nM | Nat Struct Mol Biol. 2006 Feb; 13(2): 177-8. |
| ☐ BoxB | ☐ N | 90 nM | Cell. 1998 Apr 17; 93(2): 289-99 |

The nucleotide sequences derived from artificial RNA-protein complex interaction motifs are the RNA nucleotide sequences of RNA-protein interaction motifs in artificially designed RNA-protein complexes. Such nucleotide sequences are usually composed of approximately 10 to 80 bases and designed to form specific binding in a noncovalent manner, i.e., through a hydrogen bond, with a particular amino acid sequence of a particular protein. Examples of such nucleotide sequences derived from artificial RNA-protein complex interaction motifs include, but are not limited to, RNA aptamers specifically binding to the apoptosis-inducing protein Bcl-2 family, and RNA aptamers specifically recognizing cancer cell surface antigens. Moreover, nucleotide sequences listed in Table 3 below are also known, and these can also be used as the RNA-protein complex interaction motif-derived nucleotide sequence 2 of the present invention.

TABLE 3

| RNA name | Protein name | Kd | Document |
|---|---|---|---|
| Rev aptamer 5 | Rev | 190 nM | RNA. 2005 Dec; 11(12): 1848-57 |
| Aptamer | p50 | 5.4 ± 2.2 nM | Proc Natl Acad Sci USA. 2003 Aug 5; 100(16): 9268-73. |
| BMV Gag aptamer | BMV Gag | 20 nM | RNA. 2005 Dec; 11(12): 1848-57 |

TABLE 3-continued

| RNA name | Protein name | Kd | Document |
|---|---|---|---|
| BMV Gag aptamer | CCMV Gag | 260 nM | RNA. 2005 Dec; 11(12): 1848-57 |
| CCMV Gag aptamer | CCMV Gag | 280 nM | RNA. 2005 Dec; 11(12): 1848-57 |
| CCMV Gag aptamer | BMV Gag | 280 nM | RNA. 2005 Dec; 11(12): 1848-57 |

The artificial RNA-protein complexes can be prepared by using a molecular design method and an in-vivo evolution method in combination. The in-vivo evolution method can produce aptamers or ribozymes by selecting functional RNAs from molecular libraries having various sequence diversities, and repeating the reactions of amplification and transcription of their genes (DNAs). Thus, RNA-protein interaction motifs adapted to RNP having a functional structure of interest can be extracted in advance from natural RNP molecules by molecular design or prepared artificially by the in-vitro evolution method. In the present embodiment, for the RNA-protein complex interaction motif-derived nucleotide sequence 2, it is preferred that the RNA-protein complex from which the nucleotide sequence is derived should have a dissociation constant Kd of approximately 0.1 nM to approximately 1 µM. Specific examples of the protein-binding motif sequence 21 include a Box CD sequence: 5'-GGGCGUGAUGCGAAAGCUGACCC-3' (SEQ ID NO: 2), which is a nucleotide sequence binding to L7Ae (SEQ ID NO: 1) (Moore T et al., Structure Vol. 12, pp. 807-818 (2004)) known to participate in RNA modifications such as RNA methylation or pseudouridylation.

The constitution of the shRNA according to the present embodiment can be obtained by molecular design. The sensor shRNA of the present embodiment can be obtained, for example, by introducing a protein-binding motif sequence to a sequence portion forming the linker strand, based on the sequence of known natural or nonnatural shRNA, or by replacing a protein-binding motif sequence for a sequence portion forming the linker strand, based on the sequence of known natural or nonnatural shRNA. In this procedure, the type and introduction position of the protein-binding motif sequence can be determined in view of the appropriate placement of RNP of interest such that the function of the Dicer protein can be inhibited.

Alternatively, the nucleotide sequence of the guide strand can be determined according to the desired target sequence to design the linker strand and the passenger strand by computer-aided molecular modeling. In this procedure, particular attention may be paid to the correct formation of a duplex structure by the guide strand and the passenger strand.

The shRNA according to the first embodiment may be stably present through the formation of the hairpin structure shown in FIG. 1 under physiological conditions involving pH 6.5 to 8.0 and a temperature of 4 to 42° C., preferably pH 7.3 to 7.5 and a temperature of 4 to 37° C. When the shRNA according to the first embodiment may be present in this form in vivo, this shRNA is recognized by an RNA duplex-cleaving enzyme Dicer. Then, the shRNA may be cleaved at positions shown by arrowheads a and b in FIG. 1 to form an RNA duplex of approximately 19 to 24 bases in the length of each strand having a 2-base protruding end. As a result, the guide RNA complementary to the target mRNA can be transferred from RLC to RISC to inhibit the translation of the mRNA to be controlled by its cleavage.

Thus, the shRNA according to the first embodiment is characterized in that the shRNA in the form shown in the drawing, i.e., in the form in which the protein-binding motif sequence 21 is unbound to the particular protein, functions in the same way as known natural shRNA.

Next, according to the second embodiment, the present invention provides an RNAi control system comprising: the shRNA according to the first embodiment; and an RNP-derived protein which specifically binds to a protein-binding motif sequence in the shRNA.

Figure 2A:
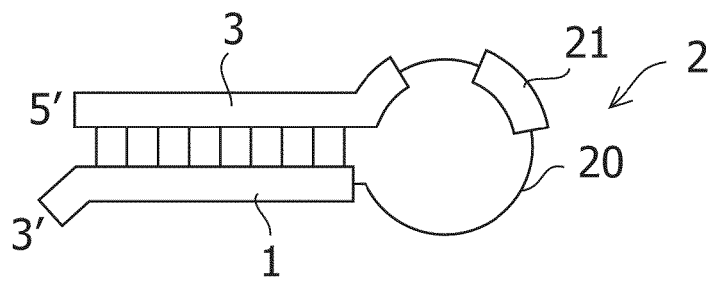
FIG. 2(A) schematically shows an shRNA constituting an RNAi control system according to the second embodiment, FIG. 2(B) schematically shows an RNP-derived protein 4 constituting the RNAi control system according to the second embodiment, and FIG. 2(C) schematically shows a complex of the shRNA and the protein 4 in a system in which the shRNA and the protein 4 coexist.
Figure 2B:
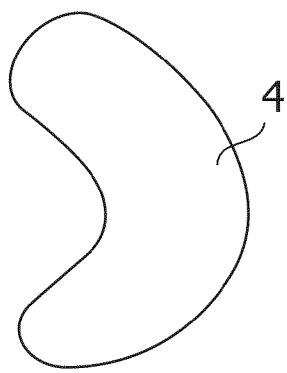

The shRNA constituting the RNAi control system according to the present embodiment is schematically shown in FIG. 2(A), and an RNP-derived protein 4 is schematically shown in FIG. 2(B). The shRNA is as described in the first embodiment, and its description is omitted here. The same reference numerals will be used to designate the same components as those in FIG. 1.

The protein 4 shown in FIG. 2(B) is a protein that is derived from RNP and specifically binds to the protein-binding motif sequence 21 on the shRNA. Accordingly, this protein 4 can be determined in a manner specific for a sequence selected as the protein-binding motif sequence 21. Specifically, when Box C/D (SEQ ID NO: 2) is selected as the protein-binding motif sequence 21, the protein 4 is L7Ae (SEQ ID NO: 1). The protein 4 may also be a fusion protein containing the protein specifically binding to the protein-binding motif sequence 21 or may be a protein having an additional peptide added to the protein specifically binding to the protein-binding motif sequence 21. This is because the protein 4 needs only to be capable of inhibiting recognition by Dicer described below.

In the state shown in FIG. 2(A), the shRNA according to the present embodiment functions in the same way as known natural shRNA, as described in the first embodiment, in the absence of the protein 4 to cause RNAi such that the translational function of particular mRNA is inhibited.

Figure 2C:
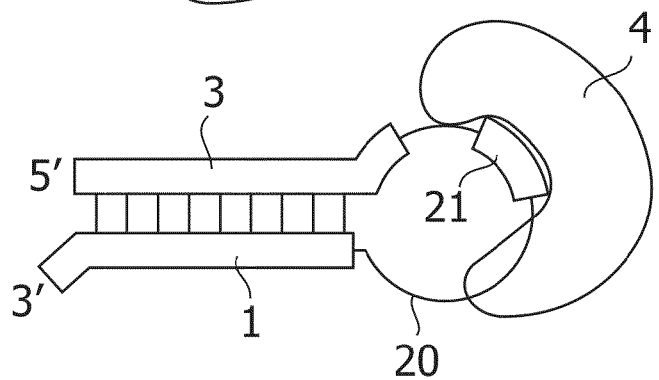

Next, the states of the shRNA according to the present embodiment and the protein 4 in a system in which these molecules coexist will be described. FIG. 2(C) schematically shows the shRNA and the protein 4 in the system in which the shRNA and the protein 4 coexist. The shRNA and the protein 4 may be stably present in the form of an RNP complex formed by specific binding under physiological conditions involving pH 6.5 to 8.0 and a temperature of 4 to 42° C., preferably pH 7.0 to 7.5 and a temperature of 4 to 37° C.

The present embodiment is characterized in that when the protein-binding motif sequence 21 on the shRNA specifically bind the protein 4 to form an RNP by specific binding, Dicer fails to recognize the shRNA in this RNP form. As a result, the Dicer fails to cleave the shRNA. Then, it cannot proceed to the next step of RNAi such that mRNA to be controlled is made insusceptible to cleavage. In other words, the coexistence of the shRNA according to the present embodiment with the protein 4 can inhibit RNAi. Moreover, according to the embodiment the protein 4 as input information is transformed to RNAi inhibition as output.

In this context, the system in which the shRNA and the protein 4 coexist may be a mixture of separately prepared shRNA and protein 4 molecules in a medium. Alternatively, a vector for expression of the shRNA molecule may be designed, and a vector for expression of the molecule of the protein 4 may be designed. These vectors may be introduced into the same cell, and their expressions can also be caused to achieve the system in which the shRNA and the protein 4 coexist. The vector design will be described in detail in Examples described later.

The RNAi control system according to the second embodiment of the present invention can achieve the inhibition of shRNA-mediated RNAi in a protein-specific manner.

Next, according to the third embodiment, the present invention relates to an RNAi control method comprising the steps of: contacting the sensor shRNA according to the first embodiment with an RNP-derived protein which specifically binds to a protein-binding motif sequence in the shRNA, in a solution; and introducing the solution containing the shRNA and the protein into a cell. The combination of the sensor shRNA and the protein used in the present embodiment can be selected based on the first and second embodiments to determine their sequences.

[In-Vitro Synthesis of a Sensor ShRNA]

In this context, the sensor shRNA can be obtained by an in-vitro synthesis method called in-vitro transcription. Single-stranded DNA in which a 19-base antisense sequence (TATAGTGAGTCGTATTAGC; SEQ ID NO: 3) of a T7 promoter sequence may be bound to the 3' end of a sequence serving as a template of shRNA is artificially synthesized (Hokkaido System Science Co., Ltd.), and this may be associated with a 19-base T7 promoter sequence (GCTAATAC-GACTCACTATA (SEQ ID NO: 4)) artificially synthesized in the same way. This associate may be mixed with ribonucleic acids, salts, and T7 RNA polymerase and reacted at 37° C., as specifically described in detail in Examples to obtain the sensor shRNA.

[Production of Protein]

On the other hand, the protein can be obtained by preparing a vector for expression of the protein and causing its expression using $E.\ coli$, followed by purification. For example, a vector for expression of L7Ae (SEQ ID NO: 2), which is a protein specifically binding to a Box-C/D motif represented by SEQ ID NO: 1, can be prepared with reference to Nucleic Acid Research, 2003, Vol. 31, No. 3 869-877. One example of the vector for expression of L7Ae (SEQ ID NO: 2) in $E.\ coli$ is shown in SEQ ID NO: 5.

In the present embodiment, the contacting step may be performed by mixing the thus-prepared sensor shRNA and protein in the same solution system. The mixing of the shRNA and the protein may be performed under physiological conditions involving pH 6.5 to 8.0 and a temperature of 4 to 42° C., preferably pH 7.3 to 7.5 and a temperature of 4 to 37° C. As a result, the shRNA and the protein may specifically interact with each other to form an RNP complex.

RNAi may be inhibited in the presence of Dicer, ATP, and Mg ions and under appropriate physiological conditions, in addition to the conditions described above. Accordingly, in the contacting step, the sensor shRNA and the protein may be mixed to form an RNP complex, and then, the step of introduction into a cell can be carried out. The concentration of the RNP complex introduced into a cell is, for example, 1 nM to 40 nM shRNA, preferably 1 nM to 20 nM shRNA, and a protein concentration of preferably, but not limited to, that about 1 to 10 times the shRNA concentration. The introduction of the RNP complex into a cell can be performed by, but not limited to, transfection using liposomes and can be performed by those skilled in the art using general methods for introduction of an RNP into cells known in the art.

After the introduction of the RNP complex into a cell, the phenomenon described in the first embodiment with reference to FIG. 2 may take place in the cell containing Dicer. Specifically, Dicer neither recognizes the RNA cleavage site in the prepared complex of the sensor shRNA and the protein nor cleaves the shRNA. Then, mRNA complementary to the guide strand may not undergo RNAi. Thus, the expression of a protein encoded by this mRNA may be inhibited.

According to the third embodiment of the present invention, RNAi can be inhibited in vitro.

In a modification of the third embodiment, the protein alone can be administered directly to a cell. This modification involves, after the introduction of the protein into a cell, forming an RNP complex of the sensor shRNA and the protein in the cell, and differs in this point from the third embodiment which involves forming an RNP complex and then introducing it into a cell. In this modification, the sensor shRNA can be introduced into the cell before or after the introduction of the protein into the cell. When the sensor shRNA is introduced into the cell before the protein introduction, a vector for expression of the shRNA may be designed such that the expression of the shRNA in this vector introduced into the cell can be controlled using a small molecule such as tetracycline. In this method, the shRNA can be expressed using tetracycline after the protein introduction. When the sensor shRNA is introduced into the cell after the protein introduction, the shRNA may be introduced directly into the cell or a vector for expression of the shRNA may be introduced into the cell. The protein introduced in the cell forms an RNP complex with the sensor shRNA and enables the expression of a gene of interest to be controlled by RNAi in the cell. Thus, the present embodiment seems to be effective in the development of protein drugs or the treatment of diseases such as cancer.

According to the fourth embodiment, the present invention relates to an intracellular RNAi control method comprising the steps of: introducing a vector for expression of the shRNA according to the first embodiment into a cell; introducing a vector for expression of an RNP-derived protein which specifically binds to a protein-binding motif sequence in the shRNA, into the cell; and causing their expressions from the vector for expression of the shRNA and the vector for expression of the protein.

Figure 3A:
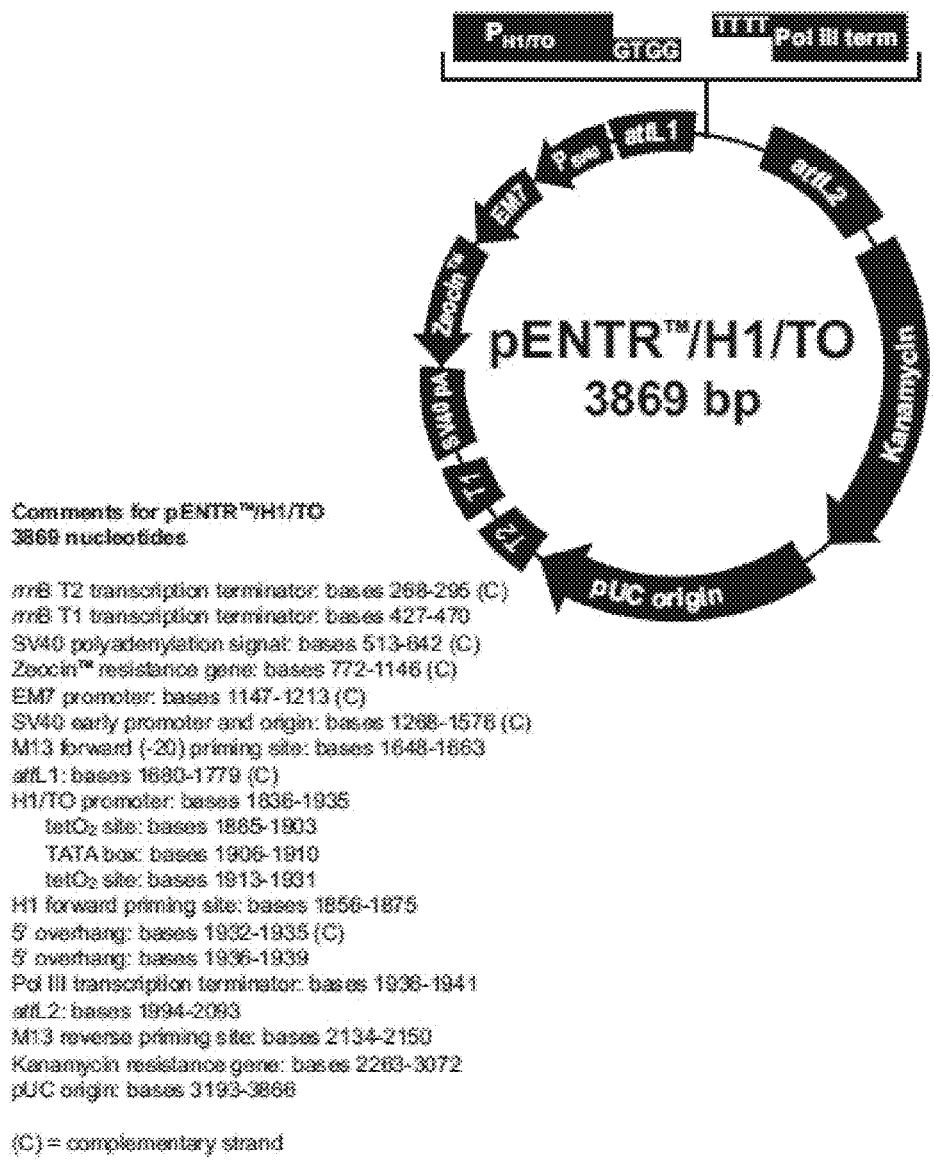
FIG. 3(A) shows a pENTR (trademark)/H1/TO vector sold by Invitrogen Corp., FIG. 3(B) schematically shows a DNA duplex inserted to the pENTR (trademark)/H1/TO vector.
Figure 3B:
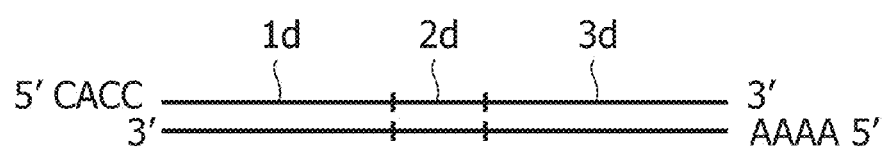

The vector for expression of the sensor shRNA can be prepared based on the primary structure sequence of the sensor shRNA determined as described in the first embodiment. One example of the vector preparation method is shown in FIG. 3. FIG. 3(A) shows a pENTR (trademark)/H1/TO vector (SEQ ID NO: 8) sold by Invitrogen Corp. A DNA sequence encoding the shRNA of the present invention may be inserted to the site shown by the arrow of FIG. 3(A). The inserted DNA duplex is schematically shown in FIG. 3(B). The upper strand shown in FIG. 3(B) comprises overhang CACC, a guide strand-encoding DNA sequence 1$d$, a linker strand-encoding DNA sequence 2$d$, and a passenger strand-encoding DNA sequence 3$d$ located in this order from the 5' end. The lower DNA strand shown in the drawing is a strand complementary to the upper strand and has overhang AAAA located at the 5' end. Those skilled in the art can obtain the desired sensor shRNA by inserting the desired sequence into commercially available plasmids to prepare plasmids producing the desired sensor shRNA.

Figure 4:
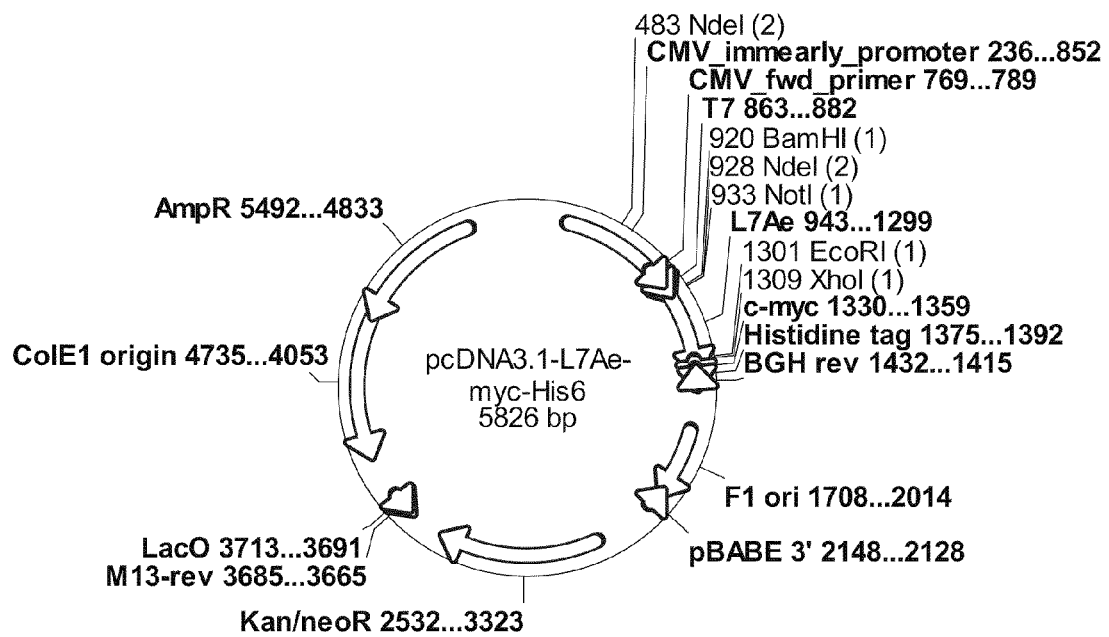
FIG. 4 shows a preparation example of a protein expression vector.

The protein expression vector can be prepared by incorporating a DNA sequence encoding a protein to be expressed, into vectors for mammalian expression. A vector preparation example is shown in FIG. 4. The vector shown in this drawing is a vector for expression of L7Ae (SEQ ID NO: 2), which is a protein specifically binding to a Box-C/D motif represented by SEQ ID NO: 1. The sequence of the vector is shown in SEQ ID NO: 6. Such a vector can be prepared with reference to Nucleic Acid Research, 2003, Vol. 31, No. 3 869-877, and a gene can be extracted therefrom and recombined to mammalian expression vector. This vector can be prepared using a pcDNA3.1 (+) myc H is A vector (SEQ ID NO: 7) commercially available from Invitrogen Corp.

The present embodiment is characterized by introducing the vector for expression of the shRNA and the vector for expression of the protein into the same cell and causing their expressions. The introducing step can be carried out by transfection. Examples of the transfection include, but not limited to, transfection using liposomes, direct injection, electroporation, and a lentiviral transfection method. The amounts of the shRNA expression vector and the protein expression vector introduced into a cell may differ depending on the purpose and are, for example, the amount of the L7Ae protein expression vector ¼ times to 10 times, preferably 1 time to 4 times that of the shRNA expression vector.

According to the fourth embodiment, RNAi can be inhibited by causing the intracellular expressions of the shRNA and the protein. Examples of a practical application of the embodiment include the treatment of cancer. Moreover, an RNAi control system can also be prepared by combining the vector for expression of the sensor shRNA and the protein expression vector used in the present embodiment.

In a modification, shRNA can be designed such that the protein specifically binding to the protein-binding motif sequence shown in FIGS. 1 and 2 is, for example, a biological molecule expressed only in cancer cells, and the target sequence of the guide strand is an apoptosis-promoting gene. In this case, the shRNA may be introduced directly or via a vector into a cancer cell to form an RNP complex with a biological molecule expressed only in cancer, in the cancer cell. As a result, the shRNA may be made insusceptible to recognition by Dicer. Then, in the cancer cell, the RNAi of the apoptosis-promoting gene may be inhibited, resulting in the selective expression of the apoptosis-promoting gene to promote the apoptosis of the cancer cell. On the other hand, in a normal cell, which may be free from the biological molecule expressed only in cancer, RNAi may not be inhibited even if the same shRNA is introduced thereinto directly or via a vector. Therefore, the expression of the apoptosis-promoting gene may be inhibited by RNAi.

Moreover, in a further modification of this embodiment, shRNA can be designed such that the protein specifically binding to the protein-binding motif shown in FIGS. 1 and 2 is, for example, a biological molecule that becomes no longer expressed by carcinogenesis, and the target sequence of the guide strand may be an apoptosis-suppressing gene. In this case, the shRNA is introduced directly or via a vector into a normal cell to form an RNP complex with a biological molecule that becomes no longer expressed by carcinogenesis, in the normal cell. As a result, the shRNA may be made insusceptible to recognition by Dicer. Then, in the normal cell, the RNAi of the apoptosis-suppressing gene may be inhibited, resulting in the selective expression of the apoptosis-suppressing gene to suppress the apoptosis of the normal cell. On the other hand, in a cancer cell, which may be free from the biological molecule that becomes no longer expressed by carcinogenesis, RNAi may not be inhibited even if the same shRNA is introduced thereinto directly or via a vector. Therefore, the expression of the apoptosis-suppressing gene may be inhibited by RNAi.

Furthermore, a cancer control system using L7Ae may be constructed. The same promoter as that expressing such a cancer-related protein is incorporated upstream of the L7Ae protein expression vector. As a result, the RNAi function of apoptosis-controlling sensor shRNA comprising Box C/D incorporated in the linker strand can be regulated freely by regulating the expression of L7 in response to the expression of the cancer-related protein.

EXAMPLE 1

[Design of Protein Molecule-Responsive shRNA]

Figure 5A:
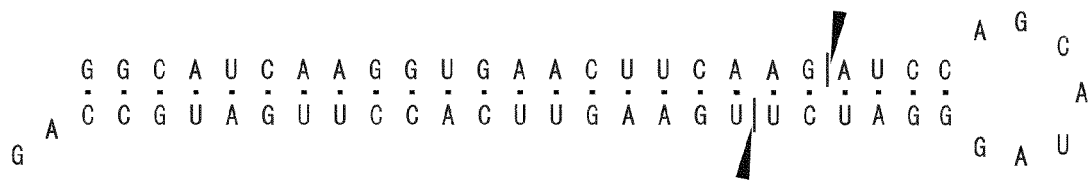
FIG. 5(A) shows the secondary structure sequence of shRNA-GFP for EGFP knockdown (SEQ ID NO:10)
Figure 5B:
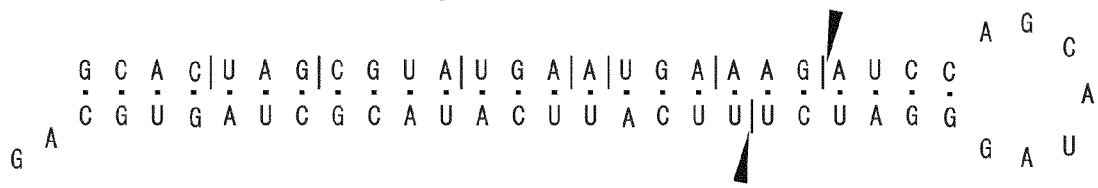
FIG. 5(B) shows the secondary structure sequence of shRNA-GFP-mut used as a negative control that does not cause EGFP knockdown (SEQ ID NO:12)
Figure 5C:
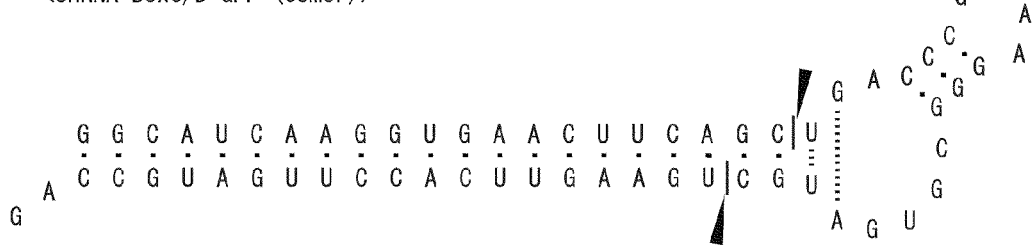
FIG. 5(C) shows the secondary structure sequence of shRNA-Box C/D-GFP that is expected to specifically bind at the Box C/D sequence to an L7Ae protein (SEQ ID NO:9)
Figure 5D:
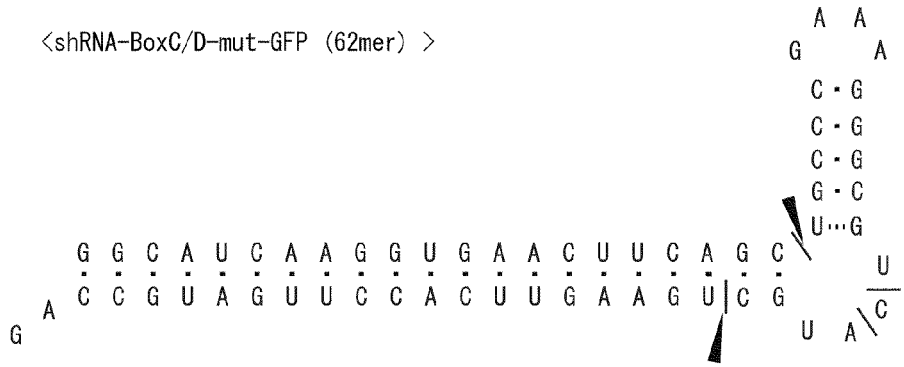
FIG. 5(D) shows the secondary structure sequence of shRNA-Box C/D-mut-GFP that does not bind to L7Ae (SEQ ID NO:11).

An shRNA-GFP sequence for EGFP knockdown (shRNA-GFP (59 mer) GGCAUCAAGGUGAACUUCAAGAUC-CAGCAUAGGGAUCUUGAAGUUCACCUUGA UGC-CAG; FIG. 5A (SEQ ID NO: 10)) was kindly provided by Dr. Tsutomu Suzuki and Dr. Takayuki Kato, the University of Tokyo. For shRNA-GFP-mut (shRNA-GFP-mut (59 mer) GCACUAGCGUAUGAAUGAAAGAUCCAG-CAUAGGGAUCUUUCAUUCAUACGCUA GUGCAG; FIG. 5B (SEQ ID NO: 12)), first, a guide strand in which three sequences complementary to the stop codons were inserted in the reading frame of three codons one for each was designed, and this was replaced for the guide strand of shRNA-GFP to design the shRNA-GFP-mut sequence. This shRNA-GFP-mut was used as a negative control that did not cause EGFP knockdown. Next, from the structure of an RNP motif L7Ae-Box C/D, the RNA sequence of Box C/D was obtained and inserted such that it was located as close to a Dicer protein cleavage site in shRNA as possible and the duplex structure of guide and passenger strands was maintained to design shRNA-Box C/D-GFP (shRNA-Box C/D-GFP (63 mer) GGCAUCAAGGUGAACUUCAGCUGAC-CCGAAAGGGCGUGAUGCUGAAGUUCACC UUGAUGCCAG; FIG. 5C (SEQ ID NO: 9)) that was expected to specifically bind at the Box C/D sequence to an L7Ae protein. In its guide strand, the 3'-terminal 21 bases of the guide strand of shRNA-GFP were used. Furthermore, shRNA in which adenine at base 24 from the 5' end of this shRNA-Box C/D-GFP was deleted and guanine at base 38 was replaced by cytosine was designed as shRNA-Box C/D-mut-GFP (shRNA-Box C/D-mut-GFP (62 mer) GGCAU-CAAGGUGAACUUCAGCUGC-CCGAAAGGGCGUCAUGCUGAAGUUCACCU UGAUGCCAG; FIG. 5(D) (SEQ ID NO: 11)) that did not bind to L7Ae.

[In-Vitro Synthesis of shRNA]
[shRNA-Box C/D-GFP]

5.25 µL of L7Aer template (100 µM, 5'-CTGGCAT-CAAGGTGAACTTCAGCATCACGC-CCTTTCGGGTCAGCTGAAGTTCACC TTGATGC-CTATAGTGAGTCGTATTAGC-3; SEQ ID NO: 13) as template DNA of shRNA, 5.25 µL of T7 sense primer (100 µM, 5'-GCTAATACGACTCACTATA-3; SEQ ID NO: 4), 30 µL of T7 RNA polymerase, 5 µL of 1 mg/mL pyrophosphatase (ROCHE), 1.75 µL of 20 mg/mL BSA, 28 µL of 1 M Hepes-KOH, 14 µL of 1 M MgCl$_2$, 3.5 µL of 1 M DTT, 14 µL of 0.1 M spermidine, 33.6 µL of 0.1 M ATP (the same holds true for CTP and UTP), 8.96 µL of 0.1 M GTP, 89.6 µL of 0.1 M GMP, and 385 µL of ultrapure water were mixed and reacted overnight at 37° C. After the reaction, 10 µL of TURBO DNase was added thereto and reacted at 37° C. for 30 minutes to degrade the template DNA. After the reaction, phenol extraction and chloroform extraction were performed, and the supernatant was charged into a PD-10 column (GE Healthcare) equilibrated with a PD-10 buffer (0.3 M potassium acetate, 15% (v/v) ethanol, pH 6.0), and washed with 3 mL of PD-10 buffer, followed by elution with 500 µL of PD-10 buffer twice. Then, to the eluate, an equal amount of ethanol was added to perform ethanol precipitation. The supernatant was discarded, and the pellet was dried and then dissolved in 20 µL of 5× dye solution (0.25% BPB, 30% glycerol). The solution was layered on a nondenaturing 15% polyacrylamide (1/30 bisacrylamide) gel and electrophoresed at room temperature for 50 minutes for separation. A band with the size of interest was excised, and 500 µL of elution buffer (0.5 M NaCl, 0.1% SDS, 1 mM EDTA) was added thereto, followed by elution overnight at 37° C. Then, a microfilter (22 μm Millex GP) was attached to a 5-mL syringe (TERUMO CORP.), and the eluate was added to the syringe and filtered through the filter. To this filtrate, a 2.5-fold volume of ethanol was added to perform ethanol precipitation. The supernatant was discarded, and the pellet was dried and then dissolved in 22 μL of ultrapure water. After concentration measurement, this solution was used in subsequent experiments.

[shRNA-Box C/D mut-GFP]

5.25 μL of L7AerN template (100 μM, 5'-CTGGCAT-CAAGGTGAACTTCAGCATGACGC-CCTTTCGGGCAGCTGAAGTTCACCT TGATGCCTAT-AGTGAGTCGTATTAGC-3; SEQ ID NO: 15) as template DNA of shRNA and 5.25 μL of T7 sense primer (100 μM, SEQ ID NO: 4) were used to perform transcription/synthesis and purification in the same way as in shRNA-Box C/D-GFP. The purification product was dissolved in 22 μL of ultrapure water. After concentration measurement, this solution was used in subsequent experiments.

[shRNA-GFP]

5.25 μL of 481P template (100 μM, 5'-CTGGCATCAAG-GTGAACTTCAAGATCCCTATGCTG-GATCTTGAAGTTCACCTTGA TGCCTATAGT-GAGTCGTATTAGC-3; SEQ ID NO: 16) as template DNA of shRNA and 5.25 μL of T7 sense primer (100 μM, SEQ ID NO: 4) were used to perform transcription/synthesis and purification in the same way as in shRNA-Box C/D-GFP. The purification product was dissolved in 22 μL of ultrapure water. After concentration measurement, this solution was used in subsequent experiments.

[Expression and Purification of L7Ae Protein]

Plasmids comprising a gene of the L7Ae protein incorporated in pET-28b+, kindly provided by Dr. Huttenhofer were amplified. From a −80° C. glycerol bacterial stock of E. coli BL21 (DE3) pLysS transformed with the pET-28b+L7Ae plasmid (SEQ ID NO: 5), the bacterial cells were inoculated to 5 mL of medium and shaken-cultured overnight at 37° C. Subsequently, the whole amount of the culture solution was inoculated to 500 mL of LB medium containing 50 μg/mL kanamycin and 100 μg/mL chloramphenicol. The bacterial cells were shake-cultured at 37° C. until O.D.$_{600}$ became 0.6 to 0.7. Then, 500 μL of 1 M IPTG was added (final concentration: 1 mM) thereto for inducing expression, and the cells were shake-cultured overnight at 30° C. The bacterial cells were collected by centrifugation (4° C., 6000 rpm, 20 minutes). After addition of 5 mL of sonication buffer (50 mM Na phosphate, 0.3 M NaCl, 2.5 mM imidazole, pH 8.0), sonication was performed to disrupt the bacterial cells. In this sonication, the procedure of cooling on ice and then irradiation with ultrasonic waves for 15 seconds was repeated 6 times. Then, impurity proteins were denatured at 80° C. for 15 minutes. The supernatant was collected by centrifugation (4° C., 6000 rpm, 20 minutes), and histidine-tagged proteins were purified by the batch method using an Ni-NTA column (Qiagen). Specifically, first, the supernatant and 1 mL of Ni-NTA were mixed and stirred at 4° C. for 1 hour. Then, the mixture was charged into the column and washed twice with 4 mL of wash buffer (50 mM Na phosphate, 0.3 M NaCl, 20 mM imidazole, pH 8.0). Stepwise elution was performed with 1 mL each of 50 mM, 100 mM, 200 mM, and 300 mM imidazole elution buffers (prepared by adding imidazole to 50 mM Na phosphate, 0.3 M NaCl, pH 8.0) in each of two runs. The proteins of interest were confirmed by 15% SDS-PAGE. Subsequently, Microcon YM-3 (Millipore Corp.) was used to concentrate the proteins, followed by buffer replacement by a dialysis buffer (20 mM Hepes-KOH, 1.5 mM MgCl$_2$, 150 mM KCl, 5% glycerol, pH 7.5). Moreover, the protein concentration was determined by the Bradford method using Protein Assay (Bio-Rad Laboratories, Inc.).

[Confirmation of RNP Complex by Gel Shift Assay]

Figure 6:
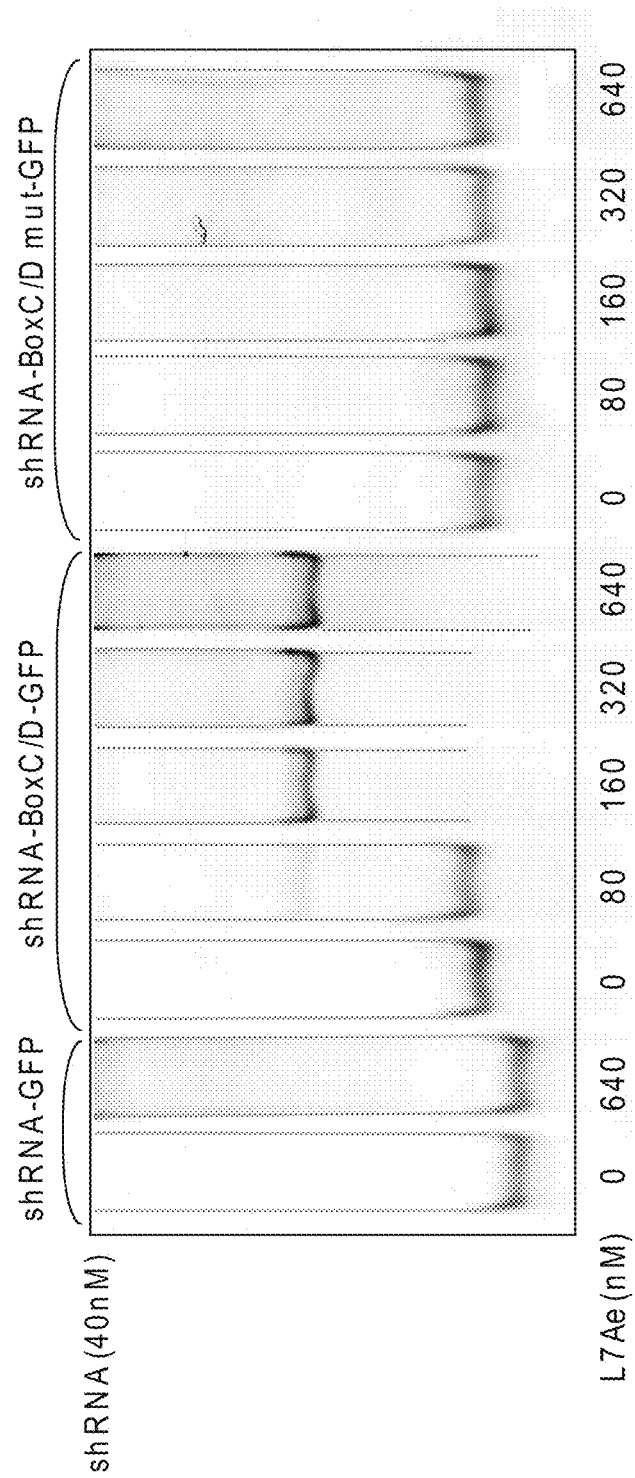
FIG. 6 shows the binding of shRNA-GFP, shRNA-Box C/D-GFP, and shRNA-Box C/D mut-GFP to L7Ae by gel shift assay.

The binding between each shRNA and the protein was confirmed as follows: after dilution with a dialysis buffer to bring the protein concentration to concentrations 25 times the final concentrations of 80 to 640 nM, 2 μL of the protein solution with each concentration, 2 μL of 1 μM shRNA-Box C/D-GFP, 6 μL of ultrapure water, and 40 μL of Opti-MEM I (trademark, Invitrogen Corp.) were mixed and left standing at room temperature for 30 minutes to bind shRNA (40 nM) to L7Ae (80 nM, 160 nM, 320 nM, or 640 nM). shRNA-GFP and shRNA-Box C/D mut-GFP were bound to L7Ae in the same way. To each solution, 13 μL of 5× dye solution (0.25% BPB, 30% glycerol) was added and mixed, and 15 μL of this mixed solution was layered on a nondenaturing 15% polyacrylamide (1/30 bisacrylamide) gel and electrophoresed at 250 V at 4° C. for 50 minutes. After the electrophoresis, the gel was stained with SYBR Green for 15 minutes, and bands were confirmed using FLA-7000 (FUJI FILM). FIG. 6 shows the binding of shRNA-GFP, shRNA-Box C/D-GFP, and shRNA-Box C/D mut-GFP to L7Ae by gel shift assay. The results suggested that shRNA-Box C/D-GFP is bound to L7Ae in a sequence-specific manner.

[Confirmation of Dicer Cleavage Inhibition by In-Vitro Dicer Cleavage Assay]

Figure 7:
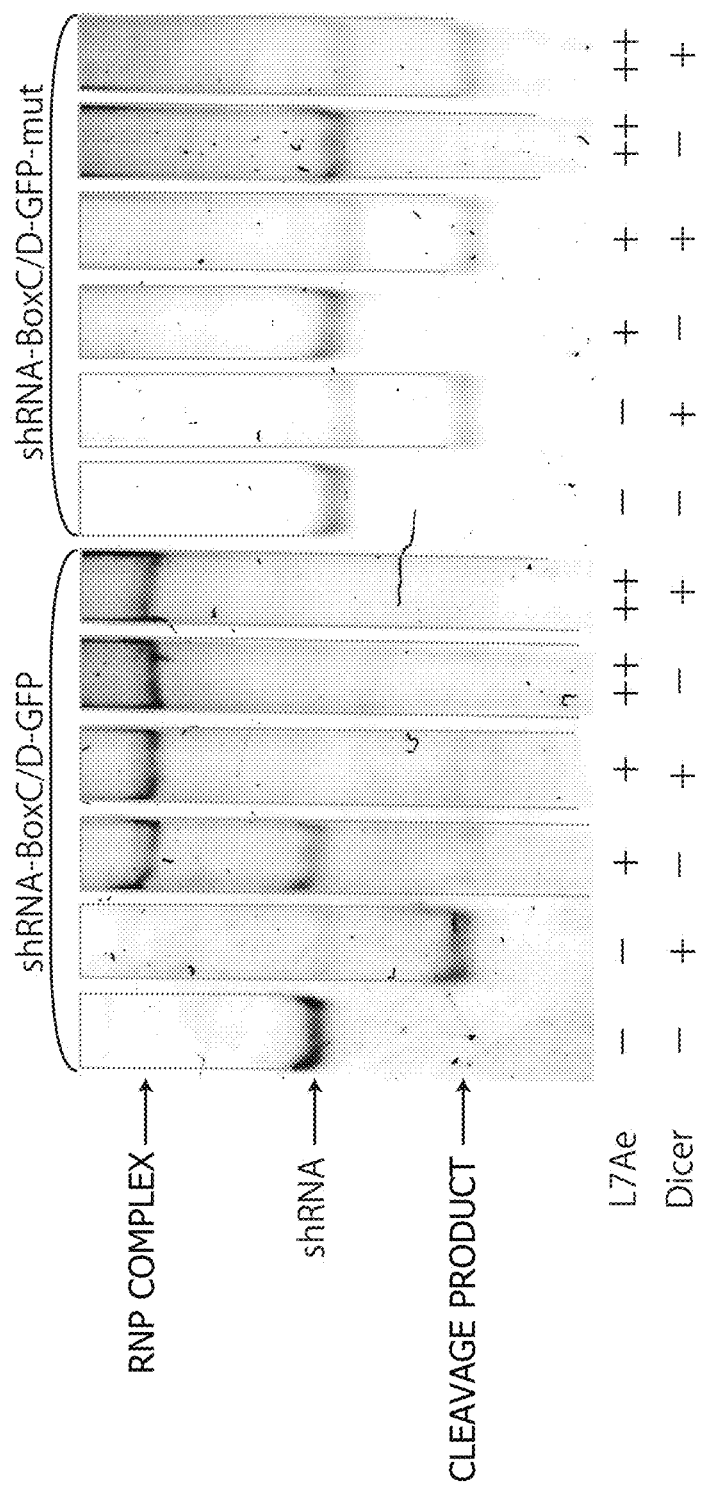
FIG. 7 shows results of the inhibition of Dicer cleavage of shRNA-Box C/D-GFP by L7Ae using an in-vitro reconstituted Dicer system.

The inhibition of Dicer cleavage of shRNA-Box C/D-GFP and shRNA-Box C/D mut-GFP by L7Ae was confirmed as follows using GTS, Inc. Recombinant Human Dicer Enzyme Kit according to the protocol: first, 0.4 μL of 4 μM shRNA, 2 μL of 4 μM or 8 μM L7Ae, 1 μL of 10 mM ATP, 0.5 μL of 50 mM MgCl$_2$, 4 μL of Dicer Reaction Buffer (GTS, Inc.), 2 μL of 0.5 unit/μL Recombinant Dicer Enzyme, and 0.1 μL of ultrapure water were mixed and reacted at 37° C. for 15 hours. Then, 2 μL of Dicer Stop Solution was added thereto and mixed. To 8 μL of this mixed solution, 2 μL of 5× dye solution was added, and the mixture was layered on a nondenaturing 15% polyacrylamide (1/30 bisacrylamide) gel and electrophoresed at 4° C. for 50 minutes. After the electrophoresis, the gel was stained with SYBR Green, and bands were confirmed using FLA-7000 (FUJI FILM). FIG. 7 shows results of the inhibition of Dicer cleavage of shRNA-Box C/D-GFP and shRNA-Box C/D mut-GFP by L7Ae using an in-vitro reconstituted Dicer system. In FIG. 7, the mark + in L7Ae represents a sample prepared from 4 μM L7Ae, the mark ++ represents a sample prepared from 8 μM L7Ae, and the mark − represents that L7Ae was not used. Likewise, the mark + in Dicer represents that Dicer was used, and the mark − represents that Dicer was not used. The results suggested that upon sequence-specific binding to L7Ae, shRNA-Box C/D-GFP is made insusceptible to cleavage by Dicer.

[Construction/Synthesis of shRNA Expression Plasmid]
[Synthesis of pENTR/H1/TO-shRNA-Box C/D-GFP (SEQ ID NO: 17)]

5 μL of pENTR L7Aer Top strand (200 μM, 5'-CACCG-GCATCAAGGTGAACTTCAGCTGAC-CCGAAAGGGCGTGATGCTGAAGTTC ACCTTGAT-GCC-3; SEQ ID NO: 18) as single-stranded DNA containing an shRNA-encoding sequence for insertion to pENTR/H1/TO vectors (Invitrogen Corp.), 5 μL of pENTR L7Aer Bottom strand (200 μM, 5'-AAAAGGCATCAAGGTGAACT-TCAGCATCACGCCCTTTCGGGTCAGCTGAAGTTCA CCTTGATGCC-3; SEQ ID NO: 19) as single-stranded DNA containing a complementary strand thereof, 2 μL of 10× Oligo Annealing Buffer (Invitrogen Corp.), and 2 μL of ultrapure water were mixed, incubated at 95° C. for 4 minutes, and then left standing at room temperature for 5 minutes to form a DNA duplex. This duplex is a duplex shown in FIG. 3(B). This DNA duplex solution was diluted 100-fold with ultrapure water, and then, 1 μL of the diluted solution was diluted 100-fold by mixing with 10 μL of 10×Oligo Annealing Buffer and 89 μL of ultrapure water. Then, 4 μL of 5× Ligation Buffer, 2 μL of 0.75 ng/μL pENTR/H1/TO vectors, 5 μL of the 10,000-fold diluted DNA solution, 8 μL of ultrapure water, and 1 μL of 1 U/μL T4 DNA Ligase were mixed and left standing at room temperature for 5 minutes to incorporate the shRNA-encoding sequence into the pENTR/H1/TO vectors. 4 μL of this reaction solution was added to TOP 10 Competent E. coli for transformation. After addition of 250 μL of S.O.C. medium, the bacterial cells were shake-cultured for 1 hour, then seeded over an LB plate containing 50 μg/mL kanamycin, and cultured overnight at 37° C. The formed colonies were confirmed, and the insert in the plasmid vectors was confirmed by colony PCR using H1 Forward Primer (10 μM, 5'-TGTTCTGGGAAATCACCATA-3; SEQ ID NO: 20), M13 Reverse Primer (10 μM, 5'-CAGGAAACAGCTAT-GAC-3; SEQ ID NO: 21), and KOD-Plus-ver. 2 (TOYOBO CO., LTD.). This colony was inoculated to 50 mL of LB medium containing 50 μg/mL kanamycin and shake-cultured at 37° C. for 16 hours. The bacterial cells were collected by centrifugation (4° C., 6000 rpm, 15 minutes) and purified according to the protocol of Plasmid Purification Kit (Qiagen), followed by isopropanol precipitation. The supernatant was discarded, and the pellet was dried and then dissolved by the addition of 55 μL of ultrapure water. After plasmid vector concentration measurement, this was used in subsequent experiments.

[Synthesis of pENTR/H1/TO-shRNA-Box C/D-mut-GFP (SEQ ID NO: 22)]

pENTR/H1/TO-shRNA-Box C/D-mut-GFP was synthesized and purified in the same way as above using 5 μL of pENTR L7AerN Top strand (200 μM, 5'-CACCGGCAT-CAAGGTGAACTTCAGCTGC-CCGAAAGGGCGTCATGCTGAAGTTCAC CTTGAT-GCC-3; SEQ ID NO: 23) as single-stranded DNA containing an shRNA-encoding sequence for insertion to pENTR/H1/TO vectors (Invitrogen Corp.) and pENTR L7AerN Bottom strand (200 μM, 5'-AAAAGGCATCAAGGTGAACT-TCAGCATGACGCCCTTTCGGGCAGCTGAAGTTCAC CTTGATGCC-3; SEQ ID NO: 24) as single-stranded DNA containing a complementary strand thereof, and dissolved by the addition of 55 μL of ultrapure water. After plasmid vector concentration measurement, this was used in subsequent experiments.

[Synthesis of pENTR/H1/TO-shRNA-GFP (SEQ ID NO: 25)]

pENTR/H1/TO-shRNA-GFP was synthesized and purified in the same way as above using 5 μL of pENTR 481P Top strand (200 μM, 5'-CACCGGCATCAAGGTGAACTTCAA-GATCCAGCATAGGGATCTTGAAGTTCACCTT GAT-GCC-3; SEQ ID NO: 26) as single-stranded DNA containing an shRNA-encoding sequence for insertion to pENTR/H1/TO vectors (Invitrogen Corp.) and pENTR 481P Bottom strand (200 μM, 5'-AAAAGGCATCAAGGTGAACT-TCAAGATCCCTATGCTGGATCTTGAAGTTCACCTT GATGCC-3; SEQ ID NO: 27) as single-stranded DNA containing a complementary strand thereof, and dissolved by the addition of 55 μL of ultrapure water. After plasmid vector concentration measurement, this was used in subsequent experiments.

[Synthesis of pENTR/H1/TO-shRNA-GFP-mut (SEQ ID NO: 28)]

pENTR/H1/TO-shRNA-GFP-mut was synthesized and purified in the same way as above using 5 μL of pENTR Sk-7N Top strand (200 μM, 5'-CACCGCACTAGCGTAT-GAATGAAAGATCCAGCATAGG-GATCTTTCATTCATACGC TAGTGC-3; SEQ ID NO: 29) as single-stranded DNA containing an shRNA-encoding sequence for insertion to pENTR/H1/TO vectors (Invitrogen Corp.) and pENTR Sk-7N Bottom strand (200 μM, 5'-AAAAGCACTAGCGTATGAATGAAAGATC-CCTATGCTGGATCTTTCATTCATACGC TAGTGC-3; SEQ ID NO: 30) as single-stranded DNA containing a complementary strand thereof, and dissolved by the addition of 55 μL of ultrapure water. After plasmid vector concentration measurement, this was used in subsequent experiments.

[Synthesis of pcDNA3.1-L7Ae-myc-His6 (SEQ ID NO: 6)]

PCR was performed using pET-28b+L7Ae (SEQ ID NO: 5) as template DNA and BamHI-NdeI-NotI-L7Ae-primer (5'-AAGGATCCATCATATGCGGCCGCTTATG-TACGTGAGATTTGAGG-3') (SEQ ID NO: 32) and L7Ae-EcoRI-XhoI-primer (5'-CACTCGAGTTGAATTCTCTTCTGAAGGCCTTTAATC-3') (SEQ ID NO: 33) as primers. 50 μL of this reaction solution contained a mixture of 2.5 μL of 10 ng/μL template DNA, 1.5 μL of each 10 μM DNA primer, 5 μL of 2 mM dNTPs, 5 μL of 10×KOD-PLUS-buffer ver. 2, 2 μL of 25 mM MgSO$_4$, 1 μL of KOD-PLUS-DNA Polymerase, and 31.5 μL of ultrapure water. The reaction was performed by initial incubation at 94° C. for 2 minutes, followed by 36 cycles each involving 98° C. for 10 seconds, 55° C. for 30 seconds, and 68° C. for 1 minute. From the resulting PCR product, DNA was purified using PCR Purification Kit (QIAGEN). However, elution was performed with 30 μL of ultrapure water, and this DNA was used as a template in restriction enzyme treatment. 27 μL of the template, 5 μL of B Buffer (ROCHE), 1 μL of 10 U/μL BamH1 (ROCHE), 1 μL of 10 U/μL XhoI (ROCHE), and 16 μL of ultrapure water were mixed and reacted at 37° C. for 2 hours for restriction enzyme treatment. Also for pcDNA3.1 (+) myc H is A vectors (Invitrogen Corp.), 1.88 μL of 1.6 μg/μL pcDNA vectors, 5 μL of B Buffer, 1 μL of 10 U/μL BamH1, 1 μL of 10 U/μL XhoI, and 41.12 μL of ultrapure water were mixed, and restriction enzyme treatment was performed in the same way. These treatment products were purified using PCR Purification Kit (QIAGEN). However, for elution, DNA was eluted into 10 μL of ultrapure water.

1.75 μL of the PCR product thus subjected to restriction enzyme treatment, 0.25 μL of the vectors thus subjected to restriction enzyme treatment, and 2 μL of Ligation High were mixed and incubated at 16° C. for 30 minutes. To the whole amount of this ligation reaction solution, 20 μL of Top10 Chemically competent cells (Invitrogen Corp.) was added. The cells were left standing on ice for 45 minutes, then placed in water bath at 42° C. for 1 minute, and left standing again on ice for 2 minutes for transformation. After further addition of 160 μL of LB medium, the cells were seeded over an LB plate containing 50 μg/mL ampicillin and incubated overnight at 37° C. The formed colonies were subjected to colony PCR using Extaq (TAKARA BIO INC.) and the DNA primers described above to check the insert. A colony in which the insert was confirmed was inoculated to 50 mL of LB medium containing 50 μg/mL ampicillin and shake-cultured overnight at 37° C. The bacterial cells were collected by centrifugation (4° C., 6000 rpm, 15 minutes) and purified according to the protocol of Plasmid Purification Kit (Qiagen), followed by isopropanol precipitation. The supernatant was discarded, and the pellet was dried and then dissolved by the addition of 55 μL of ultrapure water. After plasmid vector concentration measurement, this plasmid vector was sequenced using T7 promoter primer (5'-TAATACGACTCACTATAGGG-3; SEQ ID NO: 34) and BGH rev primer (5'-GCTGGCAACTA-GAAGGCACAG-3; SEQ ID NO: 35) and used in subsequent experiments.

[Confirmation of Knockdown Function Control by Fluorescence Microscope Image]

On the day before transfection, HeLa cells were seeded over a 24-well plate at a concentration of $0.8 \times 10^5$ cells/well and cultured in a $CO_2$ incubator at 37° C. On the next day, the cells were cotransfected with each pENTR/H1/TO shRNA expression vector, pcDNA3.1-AsRed2-L7Ae-myc-His6 (SEQ ID NO: 40), and pcDNA3.1-EGFP-myc-His6 (SEQ ID NO: 41) using Lipofectamine 2000 (Invitrogen Corp.) (trademark). To 0.3 μg each of pENTR-shRNA-GFP, pENTR-shRNA-GFP mut, pENTR-shRNA-Box C/D-GFP, and pENTR-shRNA-Box C/D mut-GFP, 0.3 μg of pcDNA3.1-AsRed2-L7Ae-myc-His6 or pcDNA3.1-AsRed2-myc-His6 (SEQ ID NO: 42) and 0.2 μg of pcDNA3.1-EGFP-myc-His6 were added, and 1.25 μl of Lipofectamine 2000 was added per sample. These DNA-lipid complexes were incubated at room temperature for 20 minutes and added dropwise to the medium for HeLa cells. 4 hours later, medium replacement was performed. 24 hours later, the fluorescence microscope image of the cells was obtained using a fluorescence microscope (OLYMPUS IX-81) to observe the inhibition of shRNA-Box C/D-GFP function by AsRed2-L7Ae expression.

Figure 12:
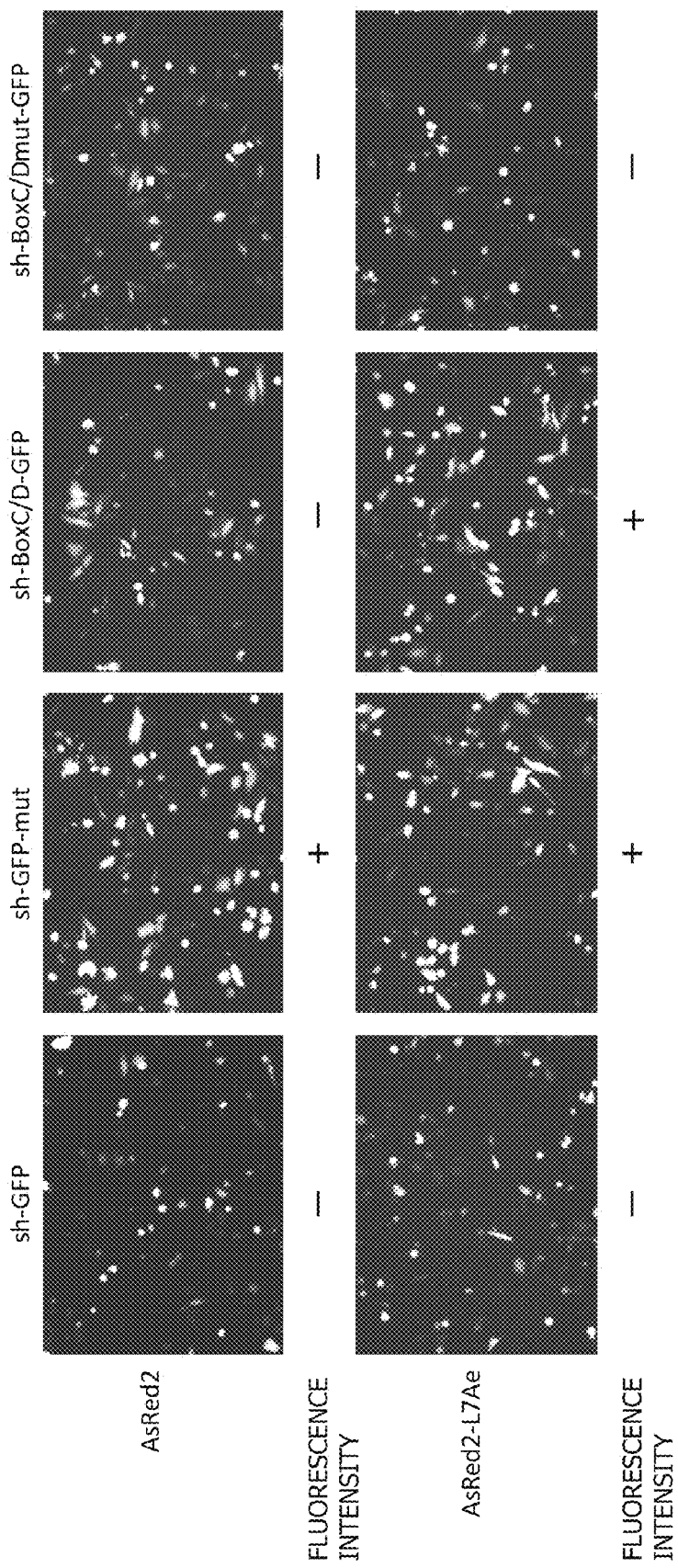
FIG. 12 is a fluorescence image of EGFP showing the inhibitory effect of AsRed2-L7Ae on the knockdown function of shRNA-Box C/D-GFP.

FIG. 12 is an EGFP fluorescence image obtained through a 510-550 nm wavelength filter by irradiation with excitation light having a wavelength around 488 nm. In FIG. 12, the mark "+" below each panel represents high fluorescence intensity, and the mark "−" represents low fluorescence intensity. This image demonstrated the inhibitory effect of AsRed2-L7Ae on the knockdown function of shRNA-Box C/D-GFP.

[Confirmation of RNAi Control by RT-PCR Analysis]

Change in GFP mRNA level caused by RNAi control by L7Ae was determined by real-time PCR.

On the previous day, HeLa-GFP cells were seeded over a 6-well plate at a concentration of $0.5 \times 10^6$ cells/well and cultured in a $CO_2$ incubator at 37° C. Then, the cells were cotransfected with each pENTR/H1/TO shRNA expression vector and pcDNA3.1-L7Ae-myc-His6. To 4 μg each of pENTR-shRNA-Box C/D-GFP and pENTR-shRNA-Box C/D mut-GFP, 0, 2, or 4 μg of pcDNA3.1-L7Ae-myc-His6 was added, and 5 μl of Lipofectamine 2000 was added per sample. These DNA-lipid complexes were incubated at room temperature for 20 minutes and added dropwise to the cells. 4 hours later, medium replacement was performed. 24 hours after the transfection, the cells were collected, and RNA extraction and DNA removal were performed using RNAqueous 4PCR Kit (Ambion, Inc. (trademark)).

Figure 8:
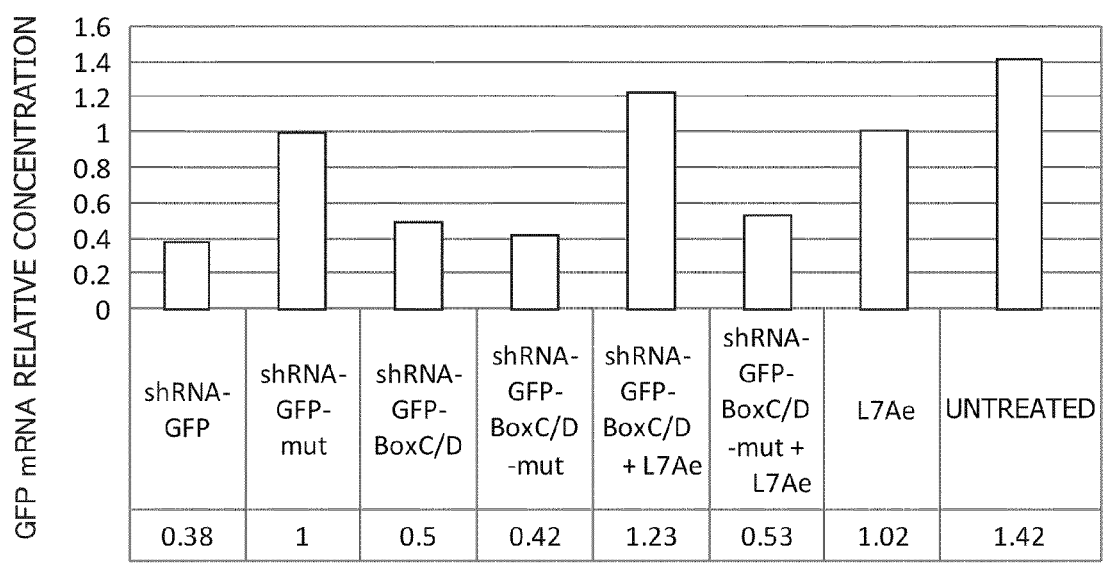
FIG. 8 is a graph showing results of RT-PCR-analyzing RNAi inhibition by L7Ae.

1.5 μg (or 0.5 μg) of the extracted RNA was used as a template to synthesize cDNA using High-Capacity cDNA Reverse Transcription Kits (Applied Biosystems Inc. (trademark)), random primers, and reverse transcriptase. Real-time PCR was performed using 1/20-diluted cDNA as a template and LightCycler 480 Taqman probe (Roche) (trademark). PCR reaction and real-time fluorescence detection were carried out using LightCycler 480 (Roche) (trademark). The reaction conditions involved an initial denaturation step at 95° C. for 5 minutes and an amplification step of 45 cycles each involving denaturation at 95° C. for 10 seconds and annealing/elongation at 60° C. for 25 seconds. Finally, the reaction solution was cooled at 50° C. for 15 seconds to terminate the measurement. The Ct value was determined by the Abs Quant/fit point method. The GFP gene of interest was amplified using 481P Fwd (5'-CAAGGAGGACGGCAACA-3') (SEQ ID NO: 36) and Rev (5'-CCTTGATGCCGTTCT-TCTGC-3') (SEQ ID NO: 37). A reference gene GAPDH was amplified using GAPDH Fwd (5'-AGCCACATCGCTCA-GACAC-3') (SEQ ID NO: 38) and GAPDH Rev (5'-GC-CAATACGACCAAATCC-3') (SEQ ID NO: 39). The amplification efficiency of GFP mRNA and GAPDH mRNA was determined using Universal probe Library probe #148 (ROCHE) and Universal probe Library probe #60 (ROCHE), respectively. The amplification product was confirmed by electrophoresis to be the single product of interest, and the results were evaluated by relative quantification. The EGFP level was normalized with GAPDH, and this normalized value was used in comparison among samples with the GFP mRNA relative level of a sample supplemented only with pENTR-shRNA-GFP mut as 1. FIG. 8 shows results of RT-PCR-analyzing RNAi inhibition by L7Ae. The difference in expression level among the samples suggested that the GFP mRNA level recovers at the time of cotransfection with pENTR-shRNA-Box C/D-GFP and pcDNA3.1-L7Ae-myc-His6 and that RNAi is inhibited in a Box C/D sequence-specific manner in the presence of L7Ae.

[Confirmation of RNAi Control of L7Ae by FACS Analysis]

On the day before transfection, HeLa-GFP cells were seeded over a 24-well plate at a concentration of $0.5 \times 10^5$ cells/well and cultured in a $CO_2$ incubator at 37° C. On the next day, the cells were cotransfected with each pENTR/H1/TO shRNA expression vector and pcDNA3.1-L7Ae-myc-His6 using Lipofectamine 2000 (Invitrogen Corp.) (trademark). To 0.8 μg each of pENTR-shRNA-Box C/D-GFP and pENTR-shRNA-Box C/D mut-GFP, 0, 0.40, or 0.80 μg of pcDNA3.1-L7Ae-myc-His6 was added, and 2 μl of Lipofectamine 2000 was added per sample. These DNA-lipid complexes were incubated at room temperature for 20 minutes and added dropwise to the cells. 4 hours later, medium replacement was performed.

Figure 9:
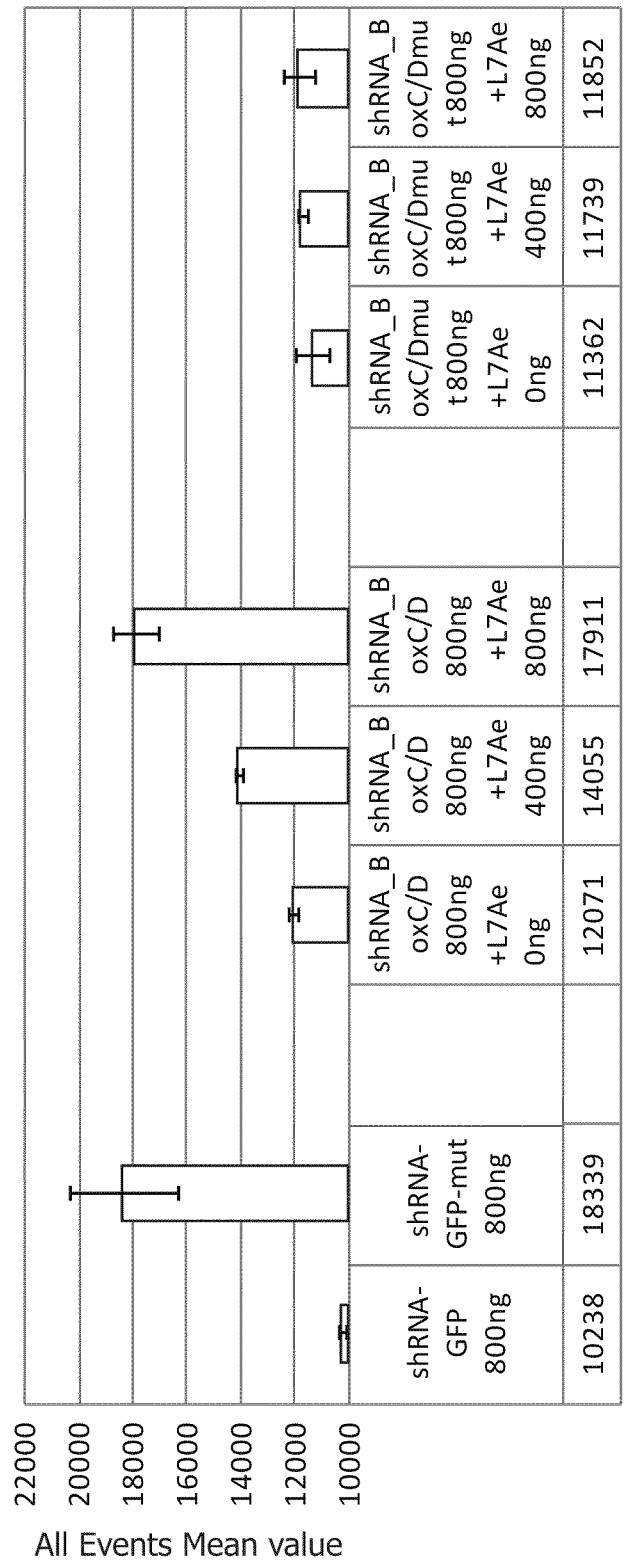
FIG. 9 is a graph showing results of FACS-analyzing RNAi inhibition by L7Ae.

24 hours after the transfection, the medium in each well was removed, and the cells were dissociated using 200 μl of Trypsin-EDTA and suspended by the addition of 200 μl of DMEM/F12. The cell suspension was transferred to a FACS tube and analyzed using FACSAria (BD). In this context, live cells were gated, and FITC was determined for 20000 cells. The analysis was conducted using a general method comprising calculating a mean value of the fluorescence intensities of all the measured cells. FIG. 9 shows the results of FACS analysis (results showing a mean value of GFP intensities of 20000 cells per sample). The results demonstrated that recovery in GFP expression is seen in a manner specific for cells cotransfected with pcDNA3.1-L7Ae-myc-His6 and pENTR-shRNA-Box C/D-GFP. This suggested that as in the results of RT-PCR analysis, RNAi is inhibited in a Box C/D sequence-specific manner in the presence of L7Ae.

EXAMPLE 2

[Design of Protein Molecule-Responsive shRNA]

shRNA-U1A-4 for EGFP knockdown (5'-GGCAUCAAG-GUGAACUUCAGGGCGAAAGCCCUGAAG-UUCACCUUGAUGCCAG-3; SEQ ID NO: 14) was designed. The shRNA-U1A-4 comprised: 5'-terminal 24 bases which were the same as those in the passenger strand of shRNA-GFP shown in FIG. 5(A) used in Example 1; a guide strand which formed a duplex therewith; and a nonhybridized loop structure GAAA. This shRNA-U1A-4 was functionally similar to shRNA-GFP and was used as a negative control. Moreover, shRNA-Box C/D-GFP (SEQ ID NO: 9) of FIG. 5(C) designed in Example 1 was used.

[In-Vitro Synthesis of shRNA]

[shRNA-U1A-4]

5.25 µL of template single-stranded DNA of shRNA-U1A-4 (100 µM, 5'-CTGGCATCAAGGTGAACT-TCAGGGCTTTCGCCCTGAAGTTCACCT-TGATGCCTAT AGTGAGTCGTATTAGC-3' SEQ ID NO: 31) and 5.25 µL of T7 sense primer (SEQ ID NO: 4) were used to perform transcription/synthesis and purification in the same way as in shRNA-Box C/D-GFP. The purification product was dissolved in 22 µL of ultrapure water. After concentration measurement, this solution was used in subsequent experiments.

[shRNA-Box C/D-GFP]

It was produced according to the in-vitro synthesis method described in Example 1.

[Expression and Purification of L7Ae Protein]

It was produced according to the L7Ae protein expression and purification using *E. coli* described in Example 1.

[Evaluation in Cultured Cell System and RNP]

[Confirmation of RNAi Inhibition of L7Ae-shRNA Complex by Observation Under Fluorescence Microscope]

On the day before transfection, HeLa-GFP cells were seeded over a 24-well plate at a concentration of 0.5×10⁵ cells/well and cultured in a CO₂ incubator at 37° C. In this context, the HeLa-GFP cell strain was HeLa cells in which GFP was stably expressed in a hygromycin-resistant manner, and was kindly provided by Dr. T. Suzuki. On the next day, the medium in the 24 wells was replaced by 500 µl of Opti-MEM (Invitrogen Corp.). At the same time, complexes of shRNA-Box C/D-GFP and the L7Ae protein were introduced into the cells by transfection using Lipofectamine 2000 (Invitrogen Corp.) (trademark). 0.6 µl of 10 µM shRNA-Box C/D-GFP, 0 µl, 0.6 µl, 1.2 µl, 2.4 µl, 4.8 µl, or 9.6 µl of 20 µM L7Ae protein, and 2 µl of 5× binding buffer were mixed, and ultrapure water was added thereto to bring the whole amount to 10 µl (for 9.6 µl of the L7Ae protein, the whole amount was brought to 12.2 µl without the addition of ultrapure water). 40 µl (for 9.6 µl of the L7Ae protein, 37.8 µl) of Opti-MEM was further added thereto and mixed, and the mixture was left standing at 4° C. for 30 minutes to form RNA-protein complexes. 48 µl of Opti-MEM and 2 µl of Lipofectamine 2000 were mixed and left standing at room temperature for 5 minutes. To this mixture, 50 µl of the RNA-protein complex solution was added and mixed, and the mixture was left standing at room temperature for 20 minutes to form RNA-protein-lipid complexes, which were in turn added dropwise to the cells. 4 hours later, the medium was replaced by 500 µl of DMEM/F12. An shRNA-free molecule (Mock) and shRNA-U1A-4 were mixed with the L7Ae protein in the same way to form RNA-protein complexes, which were in turn introduced into the cells by transfection.

Figure 10:
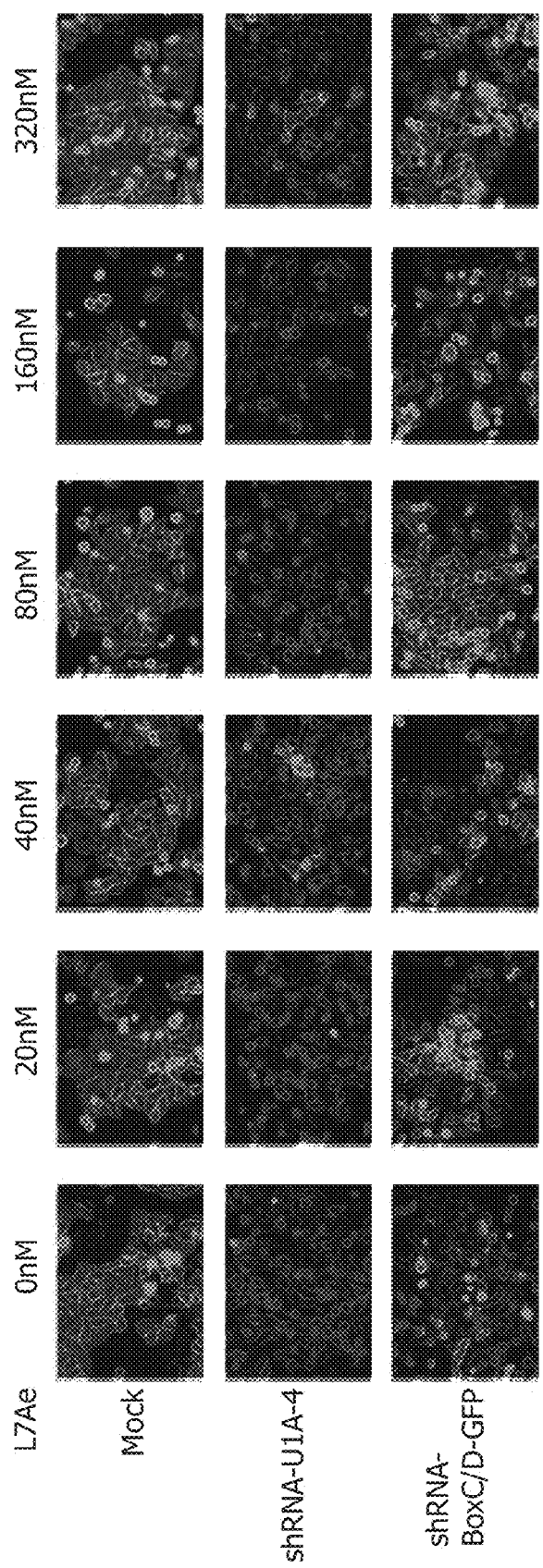
FIG. 10 is a superimposed image of fluorescence and phase-contrast images of intracellular GFP in Example2.

45 hours after the transfection, the cells were observed under a fluorescence microscope. The intracellular GFP fluorescence was photographed with settings of 20× magnification and 488 nM excitation wavelength on a fluorescence microscope (OLYMPUS) per sample. At the same time, a phase-contrast image of the cells was also taken using transmitted light. FIG. 10 shows a superimposed image of the fluorescence and phase-contrast images.

[Confirmation of RNAi Inhibition of L7Ae-shRNA Complex by FACS Analysis]

47 hours after the transfection, the medium in each well was removed, and the cells were dissociated using 200 µl of Trypsin-EDTA and suspended by the addition of 200 µl of DMEM/F12. The cell suspension was transferred to a FACS tube and analyzed using FACSAria (BD). The FACS is a method comprising irradiating, with laser light, free cells passing through a thin tube and analyzing the intensity of fluorescence emitted from the cells. In this context, live cells were gated, and FITC was determined for 10000 cells. FIG. 11 shows results of FACS-analyzing fluorescence intensity distribution. The results demonstrated that recovery in GFP expression was observed in a manner specific for the cells transfected with the complex of L7Ae and shRNA-Box C/D-GFP. This suggested that RNAi is inhibited in a Box C/D sequence-specific manner in the presence of L7Ae. For Mock, RNAi did not occur, and thus, GFP expression is seen in an L7Ae concentration-independent manner. On the other hand, for shRNA-U1A-4, RNAi was not inhibited, and thus, GFP expression was inhibited in an L7Ae concentration-independent manner.

EXAMPLE 3

[Design of Protein Molecule-Responsive shRNA]

shRNA-Box C/D-Bc1-xL (FIG. 13(B)) and shRNA-Box C/D mut-Bc1-xL (FIG. 13(C)) were designed by replacing a duplex site comprising the 5'-terminal 21 bases of shRNA-Box C/D-GFP or shRNA-Box C/D mut-GFP, by a duplex comprising a sequence of bases 365 to 385 of the Bc1-xL gene.

[Synthesis of shRNA]

[shRNA-Box C/D-Bc1-xL (FIG. 13(B) (SEQ ID NO: 43))]

5.25 µL of shRNA-Box C/D-Bc1xL template (100 µM, 5'-CTGCTTTGAACAGGTAGTGAATGAT-CACGCCCTTTCGGGTCACATTCACTACCTGT TCAAAGCTATAGTGAGTCGTATTAGC-3' (SEQ ID NO: 44)) as template DNA of shRNA and 5.25 µL of T7 sense primer (100 µM, 5'-GCTAATACGACTCACTATA-3' (SEQ ID NO: 4)) were used to perform transcription/synthesis and purification in the same way as in shRNA-Box C/D-GFP. The purification product was dissolved in 22 µL of ultrapure water. After concentration measurement, this solution was used in subsequent experiments.

[shRNA-Box C/D mut-Bc1-xL (FIG. 13(C) (SEQ ID NO: 45))]

5.25 µL of shRNA-Box C/D mut-Bc1xL template (100 µM, 5'-CTGCTTTGAACAGGTAGTGAATGAT-GACGCCCTTTCGGGCACATTCACTACCTGTT CAAAGCTATAGTGAGTCGTATTAGC-3' (SEQ ID NO: 46)) as template DNA of shRNA and 5.25 µL of T7 sense primer (100 µM, 5'-GCTAATACGACTCACTATA-3' (SEQ ID NO: 4)) were used to perform transcription/synthesis and purification in the same way as in shRNA-Box C/D-GFP. The purification product was dissolved in 22 µL of ultrapure water. After concentration measurement, this solution was used in subsequent experiments.

[shRNA-Bc1-xL (FIG. 13(A) (SEQ ID NO: 47))]

5.25 µL of shRNA-Bc1-xL template (100 µM, 5'-CT-GCTTTGAACAGGTAGTGAATGAACTC-TATGCTAGTTCATTCACTACCTGTTCAA AGCTAT-AGTGAGTCGTATTAGC-3' (SEQ ID NO: 48)) as template DNA of shRNA and 5.25 µL of T7 sense primer (100 µM, 5'-GCTAATACGACTCACTATA-3' (SEQ ID NO: 4)) were used to perform transcription/synthesis and purification in the same way as in shRNA-Box C/D-GFP. The purification product was dissolved in 22 µL of ultrapure water. After concentration measurement, this solution was used in subsequent experiments.

[Confirmation of knockdown of Bcl-xL by shRNA-Bcl-xL]

On the day before transfection, HeLa-GFP cells were seeded over a 24-well plate at a concentration of $0.5 \times 10^5$ cells/well and cultured in a CO2 incubator at 37° C. On the next day, the cells were cotransfected with Bcl-xL, expression vectors, and shRNA using Lipofectamine 2000 (Invitrogen Corp.). 0 or 0.4 μg of pBcl-xL and 10 μM shRNA-Bcl-xL were mixed and brought to 50 μl with Opti-MEM I medium (Invitrogen Corp.). Then, a mixture of 1 μl of Lipofectamine 2000 supplemented with 49 μl of Opti-MEM I medium was added per sample. These DNA-lipid complexes were incubated at room temperature for 20 minutes. After addition of 400 μl of Opti-MEM I medium, the mixture was added dropwise to the cells. 4 hours later, medium replacement was performed.

24 hours after the transfection, the medium in each well was collected. Then, the cells were dissociated using 200 μl of Trypsin-EDTA and suspended by the addition of each medium collected in the previous step. The cell suspension was subjected to centrifugal sedimentation at 500×g at 4° C. for 5 minutes and washed with 500 μl of PBS. Then, to the cell pellet, 30 μl of RIPA buffer (1×PBS, 1% NP40, 0.5% Sodium deoxycholate, 0.1% SDS, 0.3 mg/ml PMSF+2 μg/ml Aprotinin) was added, and the mixture was left standing on ice for 30 minutes. The supernatant was collected by centrifugation (4° C., 15000 g, 20 minutes). The protein concentration was determined by the Lowry method using DC-Protein Assay (Bio-Rad Laboratories, Inc.).

Bcl-xL was detected by western blotting. Proteins extracted from the cells were developed by SDS-PAGE and subjected to western blotting. A primary antibody Anti-Bcl-xL (SC-634) (Santa Cruz Biotechnology, Inc.) (1/500) and a secondary antibody Goat Anti-Rabbit IgG (H+L)-HRP conjugate (Bio-Rad Laboratories, Inc.) (1/2000) were used. Color was developed using ECL Plus (GE Healthcare) (trademark) and detected using LAS3000 (FUJI FILM). By virtue of the cotransfection of shRNA-Bcl-xL with pBcl-xL, a band showing the expression of Bcl-xL did not appear. The results demonstrated Bcl-xL knockdown by shRNA-Bcl-xL in the HeLa cells.

[Confirmation of Dicer Cleavage Inhibition by In-Vitro Dicer Cleavage Assay]

Figure 14:
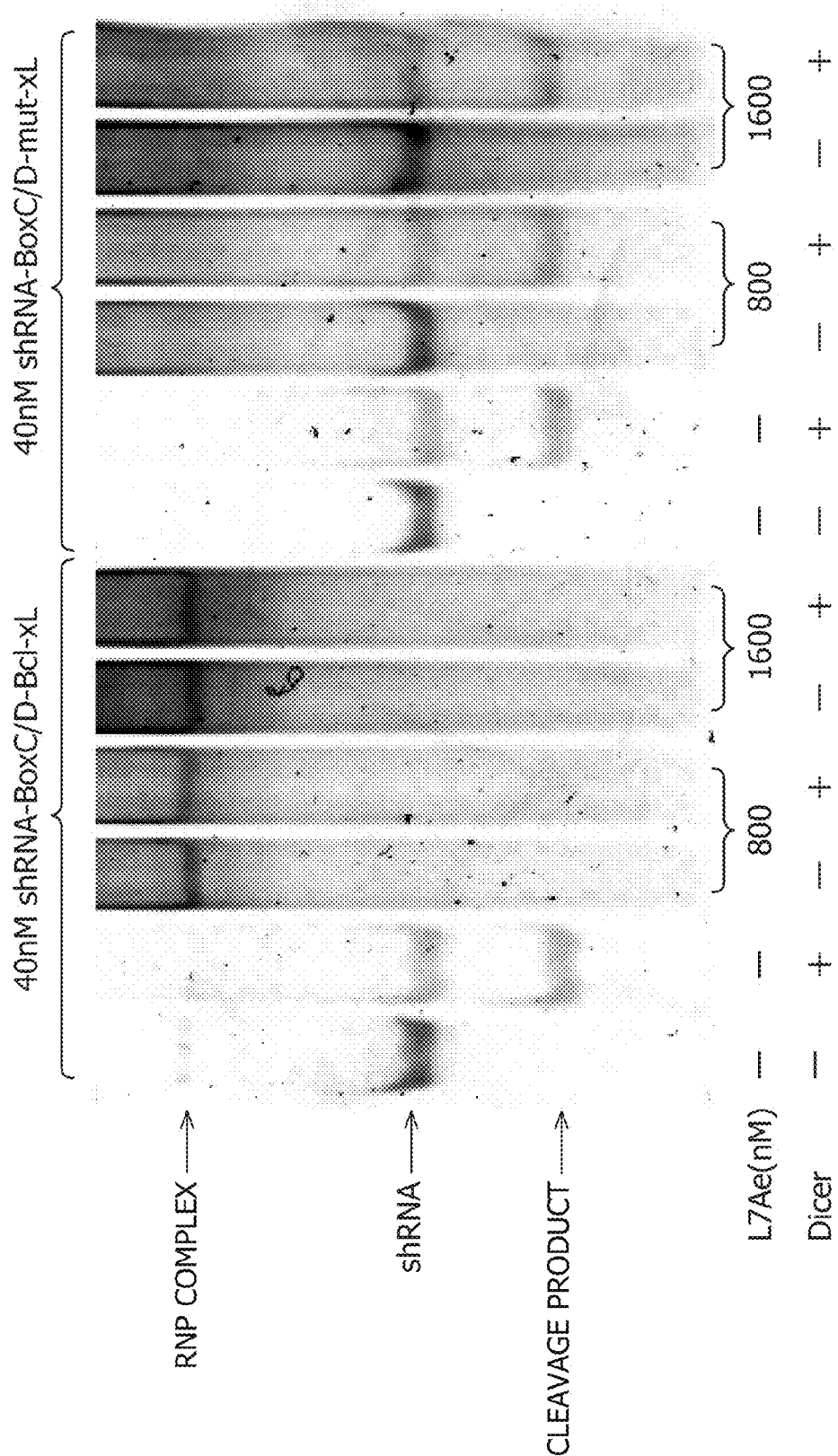
FIG. 14 shows results of the inhibition of Dicer cleavage of shRNA-Box C/D-Bc1-xL and shRNA-Box C/D mut-Bc1-xL by L7Ae using an in-vitro reconstituted Dicer system.

The inhibition of Dicer cleavage of shRNA-Box C/D-Bcl-xL and shRNA-Box C/D mut-Bcl-xL by L7Ae was confirmed as follows using GTS, Inc. Recombinant Human Dicer Enzyme Kit according to the protocol: first, 0.4 μL of 1 μM shRNA, 2 μL of 4 μM or 8 μM L7Ae, 1 μL of 10 mM ATP, 0.5 μL of 50 mM $MgCl_2$, 4 μL of Dicer Reaction Buffer (GTS, Inc.), 2 μL of 0.5 unit/μL Recombinant Dicer Enzyme, and 0.1 μL of ultrapure water were mixed and reacted at 37° C. for 14 hours. Then, 2 μL of Dicer Stop Solution was added thereto and mixed. To 8 μL of this mixed solution, 2 μL of 5× dye solution was added, and the mixture was layered on a nondenaturing 15% polyacrylamide (1/30 bisacrylamide) gel and electrophoresed at 4° C. for 50 minutes. After the electrophoresis, the gel was stained with SYBR Green, and bands were confirmed using FLA-7000 (FUJI FILM). FIG. 14 shows results of the inhibition of Dicer cleavage of shRNA-Box C/D-Bcl-xL and shRNA-Box C/D mut-Bcl-xL by L7Ae using an in-vitro reconstituted Dicer system. In FIG. 14, the mark "−" in L7Ae represents that L7Ae was not used. Likewise, the mark "+" in Dicer represents that Dicer was used, and the mark "−" represents that Dicer was not used. The results suggested that upon sequence-specific binding to L7Ae, shRNA-Box C/D-Bcl-xL is made insusceptible to cleavage by Dicer.

Construction/Synthesis of shRNA Expression Plasmid
[Synthesis of pENTR/H1/TO-shRNA-Box C/D-Bcl-xL (SEQ ID NO: 49)]

pENTR/H1/TO-shRNA-Box C/D-Bcl-xL was synthesized and purified in the same way as above using 5 μL of Box C/D Bcl-xL Top strand (200 μM, 5'-CACCGCTTTGAA-CAGGTAGTGAATGTGAC-CCGAAAGGGCGTGATCATTCACTACC TGT-TCAAAGC-3' (SEQ ID NO: 50)) as single-stranded DNA containing an shRNA-encoding sequence for insertion to pENTR/H1/TO vectors (Invitrogen Corp.) and Box C/D Bcl-xL Bottom strand (200 μM, 5'-AAAAGCTTTGAACAGG-TAGTGAATGATCACGCCCTTTCGGGTCA-CATTCACTACC TGTTCAAAGC-3' (SEQ ID NO: 51)) as single-stranded DNA containing a complementary strand thereof, and dissolved by the addition of 55 μL of ultrapure water. After plasmid vector concentration measurement, this was used in subsequent experiments.

[Synthesis of pENTR H1 TO-shRNA-Box C/D mut-Bcl-xL (SEQ ID NO: 52)]

pENTR/H1/TO-Box C/D mut-Bcl-xL was synthesized and purified in the same way as above using 5 μL of Box C/D mut Bcl-xL Top strand (200 μM, 5'-CACCGCTTTGAA-CAGGTAGTGAATGTGCCCGAAAGGGCGT-CATCATTCACTACCT GTTCAAAGC-3' (SEQ ID NO: 53)) as single-stranded DNA containing an shRNA-encoding sequence for insertion to pENTR/H1/TO vectors (Invitrogen Corp.) and Box C/D mut Bcl-xL Bottom strand (200 μM, 5'-AAAAGCTTTGAACAGGTAGTGAATGAT-GACGCCCTTTCGGGCACATTCACTACCT GTTCAAAGC-3' (SEQ ID NO: 54)) as single-stranded DNA containing a complementary strand thereof, and dissolved by the addition of 55 μL of ultrapure water. After plasmid vector concentration measurement, this was used in subsequent experiments.

[Synthesis of pENTR/H1/TO-shRNA-Bcl-xL (SEQ ID NO: 55)]

pENTR/H1/TO-shRNA-Bcl-xL was synthesized and purified in the same way as above using 5 μL of Bcl-xL Top strand (200 μM, 5'-CACCGCTTTGAACAGGTAGTGAAT-GAACTAGCATAGAGTTCATTCACTACCTGTT CAAAGC-3' (SEQ ID NO: 56)) as single-stranded DNA containing an shRNA-encoding sequence for insertion to pENTR/H1/TO vectors (Invitrogen Corp.) and Bcl-xL Bottom strand (200 μM, 5'-AAAAGCTTTGAACAGGTAGT-GAATGAACTCTATGCTAGTTCATTCACTACCTGTT CAAAGC-3' (SEQ ID NO: 57)) as single-stranded DNA containing a complementary strand thereof, and dissolved by the addition of 55 μL of ultrapure water. After plasmid vector concentration measurement, this was used in subsequent experiments.

[Experiment of RNA-Protein Complex Introduction]

To confirm the control of Bcl-xL knockdown by the binding between the L7Ae protein and shRNA-Box C/D-Bcl-xL in cultured human cancer cells, RNA-protein complexes were introduced into the cells, and the expression of Bcl-xL was detected by western blotting.

On the previous day, uterine cervix cancer-derived HeLa cells were seeded over a 24-well plate at a concentration of $1.0 \times 10^5$ cells/well and cultured in a $CO_2$ incubator at 37° C. On the next day, transfection was performed twice using Lipofectamine 2000 (Invitrogen Corp.) (trademark). To 0.4 μg of pBcl-xL or pBimEL, 1 μl of Lipofectamine 2000 was added. These DNA-lipid complexes were incubated at room temperature for 20 minutes and added dropwise to the medium for HeLa cells. 4.5 hours later, medium replacement was performed. Immediately thereafter, the second transfection was performed. 2.5 pmol (concentration in the medium: 5 nM) of shRNA-Box C/D-Bc1-xL or shRNA-Box C/D mut-Bc1-xL and 0 or 200 pmol (concentration in the medium: 400 nM) of the purified L7Ae protein were mixed to form complexes. To the complexes, 1 μl of Lipofectamine 2000 was added, and the complexes were incubated at room temperature for 20 minutes and added dropwise to the medium for HeLa cells. 5 hours later, medium replacement was performed.

22 hours after the second transfection, the medium in each well was collected. Then, the cells were dissociated using 200 μl of Trypsin-EDTA and suspended by the addition of each medium collected in the previous step. The cell suspension was subjected to centrifugal sedimentation at 500× g at 4° C. for 5 minutes and washed with 500 μl of PBS. Then, to the cell pellet, 30 μl of RIPA buffer (1×PBS, 1% NP40, 0.5% Sodium deoxycholate, 0.1% SDS, 0.3 mg/ml PMSF+2 g/ml Aprotinin) was added, and the mixture was left standing on ice for 30 minutes. The supernatant was collected by centrifugation (4° C., 15000× g, 20 minutes). The protein concentration was determined by the Lowry method using DC-Protein Assay (Bio-Rad Laboratories, Inc.).

Figure 15:
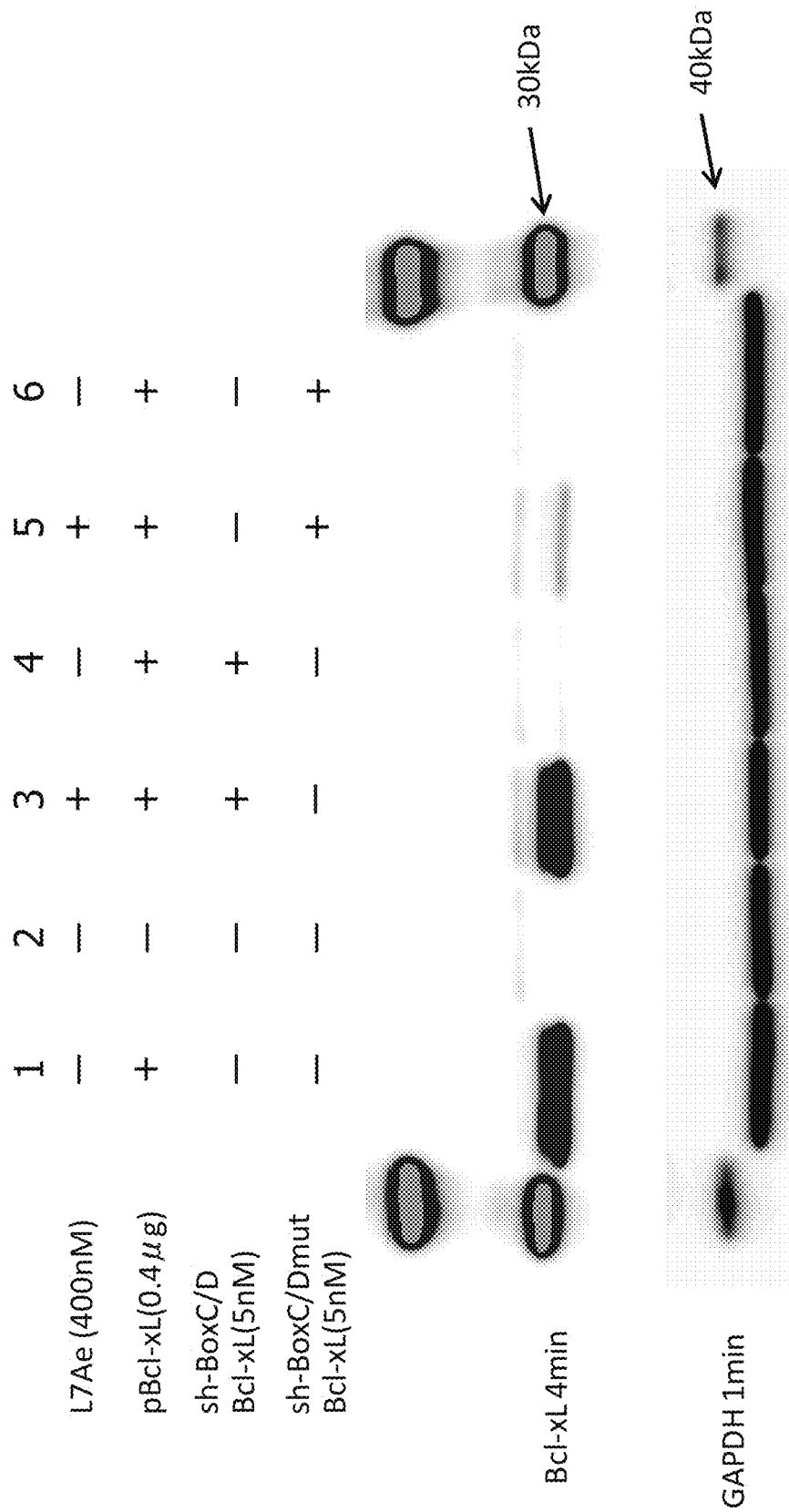
FIG. 15 shows intracellular Bc1-xL expression.
Figure 16:
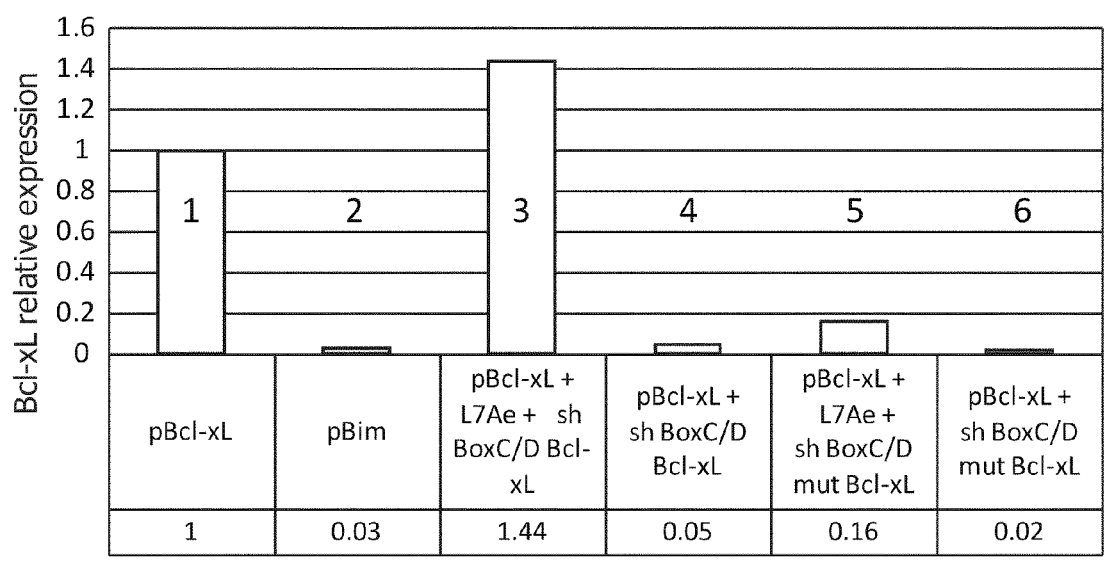
FIG. 16 shows results of adding up the intensities of detected Bc1-xL bands.

Bc1-xL or GAPDH was detected by western blotting. Proteins extracted from the cells were developed by SDS-PAGE and subjected to western blotting. A primary antibody Anti-Bc1-xL (SC-634) (Santa Cruz Biotechnology, Inc.) (1/500) and a secondary antibody Goat Anti-Rabbit IgG (H+L)-HRP conjugate (Bio-Rad Laboratories, Inc.) (1/2000) were used. Color was developed using ECL Plus (GE Healthcare) (trademark) and detected using LAS3000 (FUJI FILM). Likewise, GAPDH was subjected to western blotting using a primary antibody Anti-GAPDH (MAB374) (Chemicon International, Inc.) (1/2000) and a secondary antibody Goat Anti-Mouse IgG (H+L)-HRP conjugate (Bio-Rad Laboratories, Inc.) (1/2000). These results demonstrated that Bc1-xL knockdown was inhibited (lane 3) by the binding between the L7Ae protein and shRNA-Box C/D-Bc1-xL in the HeLa cells. Protein extraction from cells and L7Ae detection shown below were performed in the same way. FIG. 15 shows intracellular Bc1-xL expression. It was also confirmed that the protein expression level of GAPDH used as a standard control did not change. The intensities of detected Bc1-xL bands were added up. The results are shown in FIG. 16. In FIGS. 15 and 16, sh is an abbreviation of "shRNA".

[Experiment of Plasmid Introduction]

To confirm the control of Bc1-xL knockdown by the binding between the L7Ae protein and shRNA-Box C/D-Bc1-xL in cultured human cancer cells, the cells were cotransfected with plasmids for expressions of Bc1-xL, L7Ae, and shRNA, and the expression of Bc1-xL was detected by western blotting.

On the previous day, uterine cervix cancer-derived HeLa cells were seeded over a 12-well plate at a concentration of $3.0 \times 10^5$ cells/well and cultured in a $CO_2$ incubator at 37° C. On the next day, transfection was performed using Lipofectamine 2000 (Invitrogen Corp.) (trademark). 0.2 μg of pBc1-xL, 0.4 μg of pcDNA3.1-L7Ae, and 0.6 μg of pENTR/H1/TO-shRNA-Box C/D-Bc1-xL were mixed, and 2.5 μl of Lipofectamine 2000 was added thereto. These DNA-lipid complexes were incubated at room temperature for 20 minutes and added dropwise to the medium for HeLa cells. For pENTR/H1/TO-shRNA-Box C/D-mut Bc1-xL, pENTR/H1/TO-shRNA-Bc1-xL, and pENTR/H1/TO-shRNA-GFP mut (negative control), the same procedures were also performed. 0.25 μg of pcDNA-AmCyan-myc-His6 ((SEQ ID NO: 58) or 0.2 μg of pBc1-xL were introduced alone as a control plasmid into the cells. 4 hours later, medium replacement was performed.

24 hours after the transfection, the medium in each well was collected. Then, the cells were dissociated using 200 μl of Trypsin-EDTA and suspended by the addition of each medium collected in the previous step. The cell suspension was subjected to centrifugal sedimentation at 500× g at 4° C. for 5 minutes and washed with 500 μl of PBS. Then, to the cell pellet, 100 μl of RIPA buffer (1×PBS, 1% NP40, 0.5% Sodium deoxycholate, 0.1% SDS, 0.3 mg/ml PMSF+2 μg/ml Aprotinin) was added, and the mixture was left standing on ice for 30 minutes. The supernatant was collected by centrifugation (4° C., 15000 g, 20 minutes). The protein concentration was determined by the Lowry method using DC-Protein Assay (Bio-Rad Laboratories, Inc.).

Figure 17:
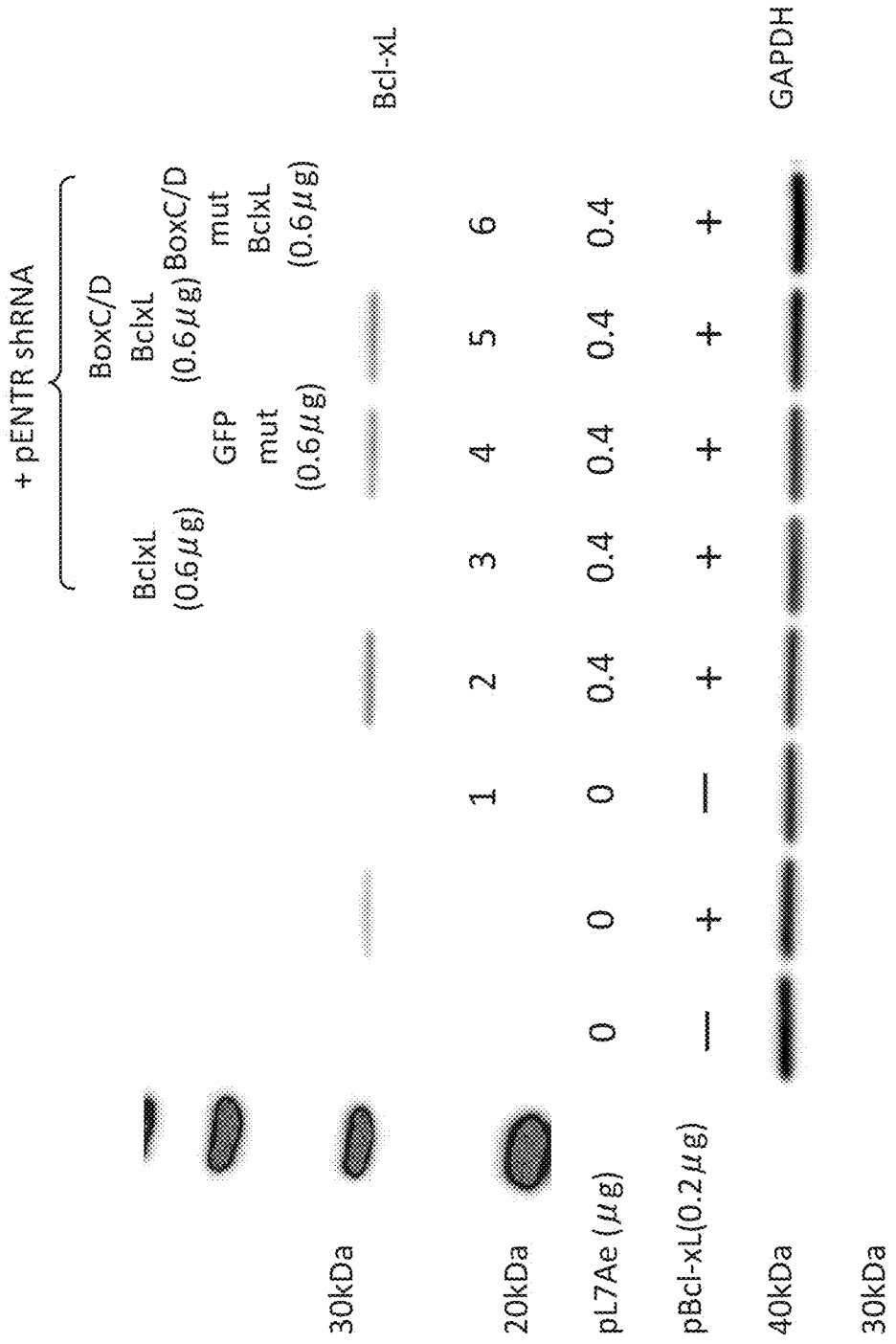
FIG. 17 shows intracellular Bc1-xL expression.
Figure 18:
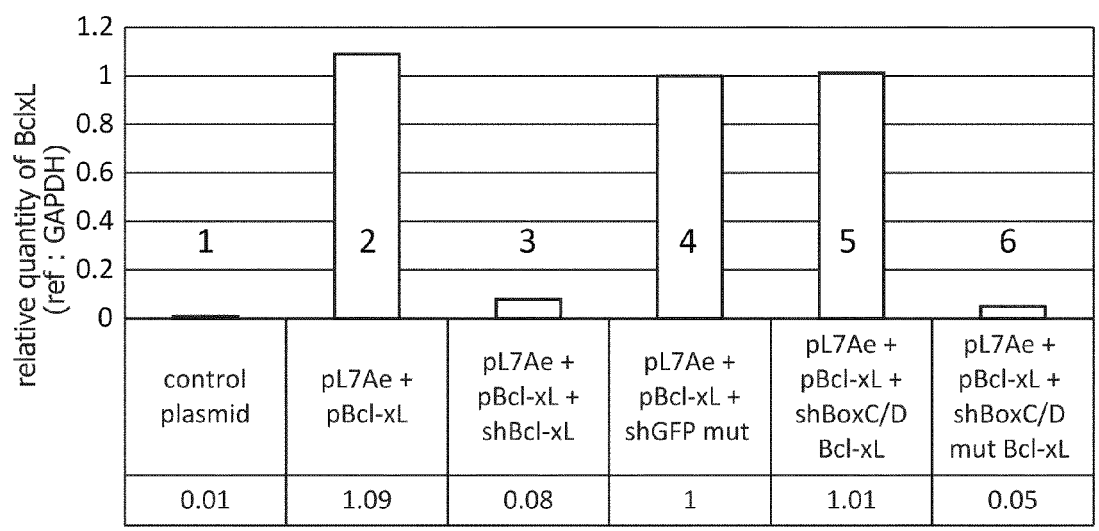
FIG. 18 shows results of adding up the intensities of detected Bc1-xL bands.

Bc1-xL or GAPDH was detected by western blotting. Proteins extracted from the cells were developed by SDS-PAGE and subjected to western blotting. A primary antibody Anti-Bc1-xL (SC-634) (Santa Cruz Biotechnology, Inc.) (1/500) and a secondary antibody Goat Anti-Rabbit IgG (H+L)-HRP conjugate (Bio-Rad Laboratories, Inc.) (1/2000) were used. Color was developed using ECL Plus (GE Healthcare) (trademark) and detected using LAS3000 (FUJI FILM). Likewise, GAPDH was subjected to western blotting using a primary antibody Anti-GAPDH (MAB374) (Chemicon International, Inc.) (1/2000) and a secondary antibody Goat Anti-Mouse IgG (H+L)-HRP conjugate (Bio-Rad Laboratories, Inc.) (1/2000). These results demonstrated that Bc1-xL knockdown was inhibited (lane 5) by the binding between the L7Ae protein and shRNA-Box C/D-Bc1-xL in the HeLa cells. FIG. 17 shows intracellular Bc1-xL expression. It was also confirmed that the protein expression level of GAPDH used as a standard control did not change. The intensities of detected Bc1-xL bands were added up. The results are shown in FIG. 18. In FIG. 18, sh in the lanes 3 to 6 is an abbreviation of "shRNA".

[Experiment of Cell Death Control by Bc1-xL Expression Level Control Responsive to L7Ae Protein]

An apoptosis-promoting protein Bim-EL and an apoptosis-suppressing protein Bc1-xL have antagonistic effect on each other, and a relatively larger amount of the protein affects the fate of cells. Thus, an experiment was conducted which involved controlling Bc1-xL expression levels using the control of Bc1-xL knockdown by the binding between the L7Ae protein and shRNA-Box C/D-Bc1-xL in cultured human cancer cells, and controlling cell death by changing the relative amount of Bc1-xL to Bim-EL.

On the previous day, uterine cervix cancer-derived HeLa cells were seeded over a 24-well plate at a concentration of $0.5 \times 10^5$ cells/well and cultured in a $CO_2$ incubator at 37° C. On the next day, transfection was performed using Lipofectamine 2000 (Invitrogen Corp.) (trademark). To 0.3 μg of pENTR/H1/TO-shRNA-Box C/D-Bc1-xL, 0.2 μg of pBc1-xL, 0.2 μg of pBimEL, and 0.2 μg of pcDNA3.1-AsRed2-L7Ae were added and mixed with a medium, and 1.25 μl of Lipofectamine 2000 was added thereto. These DNA-lipid complexes were incubated at room temperature for 20 minutes and added dropwise to the medium for HeLa cells. Approximately 4 hours later, medium replacement was performed. For pcDNA3.1 (+) myc H is A vectors (Invitrogen Corp., control vector), pENTR/H1/TO-shRNA-Box C/D-mut Bc1-xL, pENTR/H1/TO-shRNA-Bc1-xL, and pENTR/H1/TO-shRNA-GFP mut (negative control), the same procedures were also performed.

24 hours after the transfection, the medium in each well was collected. Then, the cells were dissociated using 200 μl of Trypsin-EDTA and suspended by the addition of each medium collected in the previous step. The cell suspension was subjected to centrifugal sedimentation at 500× g at 4° C. for 3 minutes and washed with 300 μl of PBS. Then, to the cell pellet, a mixed solution of 3 μl of annexin V, Pacific Blue conjugate for flow cytometry (Invitrogen Corp.) and 50 μl of annexin-binding buffer (10 mM HEPES, 140 mM NaCl, 2.5 mM $CaCl_2$, pH 7.4) was added. After tapping, the mixture was left standing at room temperature for 30 minutes for staining. Then, each sample was suspended by the addition of 200 μl of annexin-binding buffer. The cell suspension was transferred to a FACS tube and analyzed using FACSAria (BD). In this context, measurement was conducted for 30000 cells. For the analysis, first, cells emitting red fluorescence attributed to AsRed2-L7 were gated, and blue fluorescence intensity derived from Pacific Blue was measured for the cells within the gate using a filter at an excitation wavelength of 405 nm and a fluorescence wavelength of 430-470 nm. The ratio of the number of cells having this fluorescence intensity larger than the reference was measured. As the reference for determining cell death, phosphatidylserine, which is a lipid present in a manner specific for the outer membranes of dead cells, was stained with annexin V, Pacific Blue conjugate for flow cytometry (Invitrogen Corp.), and cells in which blue fluorescence intensity was larger than the upper limit of intensities of untreated cell samples stained in the same way were counted as dead cells.

As a result, the sample supplemented with the control vector (pcDNA3.1 (+) myc H is A vector) had a dead cell ratio of 8.3%, the sample supplemented with pENTR/H1/TO-shRNA-GFP mut (negative control) had a dead cell ratio of 10.1%, and the sample supplemented with pENTR/H1/TO-shRNA-Box C/D-Bc1-xL had a dead cell ratio of 13.4%. By contrast, the sample supplemented with pENTR/H1/TO-shRNA-Bc1-xL had a dead cell ratio of 34.5%, and the sample supplemented with pENTR/H1/TO-shRNA-Box C/D-mut Bc1-xL had a dead cell ratio of 42.5%. This experimental result and the Bc1-xL detection results shown in FIGS. 17 and 18 demonstrated that cells in which Bc1-xL expression level was suppressed by knockdown died approximately 3 to 4 times more than cells maintaining the expression of Bc1-xL. From the results showing that the sample supplemented with pENTR/H1/TO-shRNA-Box C/D-Bc1-xL had a dead cell ratio of 13.4%, whereas the sample supplemented with pENTR/H1/TO-shRNA-Box C/D-mut Bc1-xL had a dead cell ratio of 42.5%, it was further confirmed that cell death could be controlled suppressively by inhibiting Bc1-xL protein knockdown by L7Ae in a Box C/D sequence-specific manner.

Industrial Applicability

According to a protein-responsive shRNA and an RNAi control system using an RNP motif according to the present invention, a sensor shRNA and a protein specifically binding to it can control RNAi and are thus useful in the construction of biosensors for quantifying the expression of intracellular marker proteins without destroying cells or artificial gene circuits capable of activating the translation of proteins of interest in response to the expression level of marker proteins. For example, the present invention produces significant effect that leads to the treatment of diseases such as cancer or Alzheimer's disease by activating apoptosis-inducing proteins in response to the expression of cancer marker proteins or as a basic technique for developing protein drugs.

The invention claimed is:

1. An RNAi control system responsive to a protein expressed in a cell, the system comprising:
   a vector for expression of an shRNA comprising: a guide strand having a sequence complementary to an mRNA of a target sequence; a passenger strand which forms a duplex with the guide strand; and a linker strand which links the guide strand and the passenger strand, the linker strand comprising a Box CD sequence,
   wherein the binding of an L7Ae protein or L7Ae protein-containing fusion protein expressed in the cell to the shRNA inhibits the cleavage of the shRNA by Dicer.

2. An RNAi control method responsive to a protein expressed in a cell, the method comprising the step of:
   introducing into the cell a vector for expression of an shRNA comprising a guide strand having a sequence complementary to an mRNA of a target sequence; a passenger strand which forms a duplex with the guide strand; and a linker strand which links the guide strand and the passenger strand, the linker strand comprising a Box CD sequence,
   wherein the binding of an L7Ae protein or L7Ae protein-containing fusion protein expressed in the cell to the shRNA inhibits the cleavage of the shRNA by Dicer.

3. The RNAi control system according to claim 1, wherein the target sequence of the shRNA is Bcl-xL mRNA, and the RNAi control system controls the expression of an apoptosis regulatory protein.

4. An shRNA comprising: a guide strand having a sequence complementary to an mRNA of a target sequence; a passenger strand which forms a duplex with the guide strand; and a linker strand which links the guide strand and the passenger strand, the linker strand comprising a Box CD sequence,
   wherein in response to an L7Ae protein or L7Ae protein-containing fusion protein expressed in the cell, the cleavage of the shRNA by Dicer is inhibited to control the expression of a protein encoded by the mRNA of the target sequence.

5. The RNAi control system according to claim 1, further comprising a vector for intracellular expression of the L7Ae protein or L7Ae protein-containing fusion protein.

6. The RNAi control system according to claim 1, wherein the target sequence of the shRNA is GFP mRNA.

7. The RNAi control method according to claim 2, wherein the target sequence of the shRNA is Bcl-xL mRNA, and the RNAi control method controls the expression of an apoptosis regulatory protein.

8. The RNAi control method according to claim 2, further comprising the step of introducing a vector for intracellular expression of the L7Ae protein or L7Ae protein-containing fusion protein into the cell.

9. A method for quantifying the expression of an intracellular marker protein without destroying a cell, comprising the steps of:
   introducing to the cell the shRNA of claim 4 wherein the target sequence is a GFP mRNA; and
   measuring the fluorescence intensity of the GFP.

* * * * *